US008616211B2

(12) United States Patent
Davidson et al.

(10) Patent No.: US 8,616,211 B2
(45) Date of Patent: *Dec. 31, 2013

(54) CUSHION FOR PATIENT INTERFACE

(71) Applicant: ResMed Limited, Bella Vista (AU)

(72) Inventors: Aaron Samuel Davidson, Newport (AU); Robin Garth Hitchcock, Carlingford (AU); Matthew Eves, Carlingford (AU); David John Worboys, Belrose (AU); Susan Robyn Lynch, Epping (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/688,619

(22) Filed: Nov. 29, 2012

(65) Prior Publication Data
US 2013/0092168 A1 Apr. 18, 2013

Related U.S. Application Data

(63) Continuation of application No. 13/537,876, filed on Jun. 29, 2012, now Pat. No. 8,485,192, which is a continuation of application No. 11/793,981, filed as application No. PCT/AU2006/000032 on Jan. 12, 2006, now Pat. No. 8,220,459.

(60) Provisional application No. 60/724,303, filed on Oct. 7, 2005, provisional application No. 60/643,130, filed on Jan. 12, 2005.

(51) Int. Cl.
*A62B 18/02* (2006.01)

(52) U.S. Cl.
USPC ............ 128/206.24; 128/205.25; 128/206.12; 128/206.21; 128/206.28

(58) Field of Classification Search
USPC ............ 128/205.25, 206.21–206.26, 206.28, 128/207.13
See application file for complete search history.

(56) References Cited

U.S. PATENT DOCUMENTS

| 443,191 A | 12/1890 | Illing |
| 781,516 A | 1/1905 | Guthrie, Jr. |

(Continued)

FOREIGN PATENT DOCUMENTS

| AU | 199651130 | 10/1996 |
| AU | 2005100738 | 11/2005 |

(Continued)

OTHER PUBLICATIONS

"Ear Loop Face Mask", before Applicant's filing date.

(Continued)

*Primary Examiner* — Justine R Yu
*Assistant Examiner* — LaToya M Louis
(74) *Attorney, Agent, or Firm* — Nixon & Vanderhye P.C.

(57) ABSTRACT

A cushion for a patient interface that delivers breathable gas to a patient includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. The underlying cushion has a spring-like connection with the base wall. The underlying cushion and/or base wall define a spring constant that varies along a length of the seal.

30 Claims, 54 Drawing Sheets

(56) References Cited

U.S. PATENT DOCUMENTS

| | | |
|---|---|---|
| 812,706 A | 2/1906 | Warbasse |
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,632,449 A | 6/1927 | McKesson |
| 1,653,572 A | 12/1927 | Jackson |
| 1,710,160 A | 4/1929 | Gibbs |
| 1,926,027 A | 4/1929 | Biggs |
| 1,873,160 A | 8/1932 | Sturtevant |
| 2,011,733 A | 8/1935 | Shindel |
| 2,104,016 A | 1/1938 | Biggs |
| 2,123,353 A | 7/1938 | Catt |
| 2,130,555 A | 9/1938 | Malcom |
| 2,133,699 A | 10/1938 | Heidbrink |
| 2,166,164 A | 7/1939 | Lehmberg |
| 2,248,477 A | 7/1941 | Lombard |
| 2,254,854 A | 9/1941 | O'Connell |
| 2,317,608 A | 4/1943 | Heidbrink |
| 2,353,643 A | 7/1944 | Bulbulian |
| 2,371,965 A | 3/1945 | Lehmberg |
| 2,376,871 A | 5/1945 | Fink |
| 2,415,846 A | 2/1947 | Randall |
| 2,428,451 A | 10/1947 | Emerson |
| 2,433,565 A | 12/1947 | Korman |
| 2,438,058 A | 3/1948 | Kincheloe |
| 2,578,621 A | 12/1951 | Yant |
| 2,625,155 A | 1/1953 | Engelder |
| 2,641,253 A | 6/1953 | Engelder |
| 2,875,759 A | 12/1954 | Galleher |
| 2,706,983 A | 4/1955 | Matheson et al. |
| 2,749,910 A | 6/1956 | Faulconer, Jr. |
| RE24,193 E | 8/1956 | Emerson |
| 2,837,090 A | 6/1958 | Bloom et al. |
| 2,875,757 A | 3/1959 | Galleher, Jr. |
| 2,881,444 A | 4/1959 | Fresh et al. |
| 2,882,895 A | 4/1959 | Galeazzi |
| 2,902,033 A | 9/1959 | Galleher, Jr. |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher, Jr. |
| 3,182,659 A | 5/1965 | Blount |
| 3,189,027 A | 6/1965 | Bartlett, Jr. |
| 3,238,943 A | 3/1966 | Holley |
| 3,315,674 A | 4/1967 | Bloom et al. |
| 3,330,273 A | 7/1967 | Bennett |
| 3,330,274 A | 7/1967 | Bennett |
| 3,362,420 A | 1/1968 | Blackburn et al. |
| 3,363,833 A | 1/1968 | Laerdal |
| 3,545,436 A | 12/1970 | Holloway |
| 3,556,122 A | 1/1971 | Laerdal |
| 3,580,051 A | 5/1971 | Blevins |
| 3,670,726 A | 6/1972 | Mahon et al. |
| 3,682,171 A | 8/1972 | Dali et al. |
| 3,700,000 A | 10/1972 | Hesse |
| 3,720,235 A | 3/1973 | Schrock |
| 3,739,774 A | 6/1973 | Gregory |
| 3,754,552 A | 8/1973 | King |
| 3,796,216 A | 3/1974 | Schwarz |
| 3,799,164 A | 3/1974 | Rollins |
| D231,803 S | 6/1974 | Huddy |
| 3,861,385 A | 1/1975 | Carden |
| 3,902,486 A | 9/1975 | Guichard |
| 3,905,361 A | 9/1975 | Hewson et al. |
| 3,910,261 A | 10/1975 | Ragsdale et al. |
| 3,938,614 A | 2/1976 | Ahs |
| 3,972,321 A | 8/1976 | Proctor |
| 4,006,744 A | 2/1977 | Steer |
| 4,062,357 A | 12/1977 | Laerdal |
| 4,069,516 A | 1/1978 | Watkins, Jr. |
| 4,077,404 A | 3/1978 | Elam |
| D250,131 S | 10/1978 | Lewis et al. |
| 4,142,527 A | 3/1979 | Garcia |
| 4,153,051 A | 5/1979 | Shippert |
| 4,156,426 A | 5/1979 | Gold |
| 4,167,185 A | 9/1979 | Lewis |
| 4,226,234 A | 10/1980 | Gunderson |
| 4,239,038 A | 12/1980 | Holmes |
| 4,245,632 A | 1/1981 | Houston |
| 4,248,218 A | 2/1981 | Fischer |
| 4,263,908 A | 4/1981 | Mizerak |
| 4,264,743 A | 4/1981 | Maruyama et al. |
| 4,265,239 A | 5/1981 | Fischer, Jr. et al. |
| 4,267,845 A | 5/1981 | Robertson, Jr. et al. |
| 4,273,124 A | 6/1981 | Zimmerman |
| D262,322 S | 12/1981 | Mizerak |
| 4,304,229 A | 12/1981 | Curtin |
| 4,312,359 A | 1/1982 | Olson |
| 4,328,797 A | 5/1982 | Rollins et al. |
| 4,347,205 A | 8/1982 | Stewart |
| 4,354,488 A | 10/1982 | Bartos |
| 4,367,735 A | 1/1983 | Dali |
| 4,367,816 A | 1/1983 | Wilkes |
| 4,402,316 A | 9/1983 | Gadberry |
| 4,406,283 A | 9/1983 | Bir |
| 4,412,537 A | 11/1983 | Tiger |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,467,799 A | 8/1984 | Steinberg |
| 4,493,614 A | 1/1985 | Chu et al. |
| 4,522,639 A | 6/1985 | Ansite et al. |
| 4,548,200 A | 10/1985 | Wapner |
| 4,549,542 A | 10/1985 | Chein |
| 4,558,710 A | 12/1985 | Eichler |
| 4,572,323 A | 2/1986 | Randall |
| 4,587,967 A | 5/1986 | Chu et al. |
| 4,601,465 A | 7/1986 | Roy |
| D285,496 S | 9/1986 | Berman |
| 4,616,647 A | 10/1986 | McCreadie |
| 4,617,637 A | 10/1986 | Chu et al. |
| 4,622,964 A | 11/1986 | Flynn |
| 4,630,604 A | 12/1986 | Montesi |
| 4,641,645 A | 2/1987 | Tayebi |
| 4,641,647 A | 2/1987 | Behan |
| D289,238 S | 4/1987 | Arthur, Jr. |
| 4,655,213 A | 4/1987 | Rapoport et al. |
| 4,660,555 A | 4/1987 | Payton |
| 4,665,570 A | 5/1987 | Davis |
| 4,671,267 A | 6/1987 | Stout |
| 4,671,271 A | 6/1987 | Bishop et al. |
| 4,676,241 A | 6/1987 | Webb et al. |
| 4,677,975 A | 7/1987 | Edgar et al. |
| 4,677,977 A | 7/1987 | Wilcox |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| H397 H | 1/1988 | Stark |
| D293,613 S | 1/1988 | Wingler |
| 4,739,755 A | 4/1988 | White et al. |
| 4,753,233 A | 6/1988 | Grimes |
| 4,767,411 A | 8/1988 | Edmunds |
| 4,770,169 A | 9/1988 | Schmoegner et al. |
| 4,774,941 A | 10/1988 | Cook |
| 4,774,946 A | 10/1988 | Ackerman et al. |
| 4,782,832 A | 11/1988 | Trimble et al. |
| 4,790,829 A | 12/1988 | Bowden et al. |
| 4,799,477 A | 1/1989 | Lewis |
| 4,802,857 A | 2/1989 | Laughlin |
| 4,803,981 A | 2/1989 | Vickery |
| 4,809,692 A | 3/1989 | Nowacki et al. |
| 4,811,730 A | 3/1989 | Milano |
| 4,819,629 A | 4/1989 | Jonson |
| 4,821,713 A | 4/1989 | Bauman |
| 4,830,138 A | 5/1989 | Palmaer et al. |
| 4,838,878 A | 6/1989 | Kalt et al. |
| 4,841,953 A | 6/1989 | Dodrill |

(56) References Cited

U.S. PATENT DOCUMENTS

| | | |
|---|---|---|
| 4,848,334 A | 7/1989 | Bellm |
| 4,848,366 A | 7/1989 | Aita et al. |
| 4,899,740 A | 2/1990 | Napolitano |
| 4,905,683 A | 3/1990 | Cronjaeger |
| 4,907,584 A | 3/1990 | McGinnis |
| 4,910,806 A | 3/1990 | Baker et al. |
| 4,914,957 A | 4/1990 | Dougherty |
| 4,915,105 A | 4/1990 | Lee |
| 4,919,128 A | 4/1990 | Kopala et al. |
| 4,919,654 A | 4/1990 | Kalt |
| 4,938,210 A | 7/1990 | Shene |
| 4,938,212 A | 7/1990 | Snook et al. |
| 4,941,476 A | 7/1990 | Fisher |
| 4,944,310 A | 7/1990 | Sullivan |
| 4,945,907 A | 8/1990 | Tayebi |
| 4,947,860 A | 8/1990 | Fisher |
| D310,431 S | 9/1990 | Bellm |
| 4,960,121 A | 10/1990 | Nelson et al. |
| 4,966,590 A | 10/1990 | Kalt |
| 4,969,880 A | 11/1990 | Zamierowski |
| 4,971,051 A | 11/1990 | Toffolon |
| 4,976,698 A | 12/1990 | Stokley |
| 4,986,269 A | 1/1991 | Hakkinen |
| 4,989,596 A | 2/1991 | Macris et al. |
| 4,989,599 A | 2/1991 | Carter |
| 4,996,983 A | 3/1991 | Amrhein |
| 5,000,173 A | 3/1991 | Zalkin et al. |
| 5,003,633 A | 4/1991 | Itoh |
| 5,005,568 A | 4/1991 | Loescher et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,046,491 A | 9/1991 | Derrick |
| 5,062,421 A | 11/1991 | Burns et al. |
| 5,063,922 A | 11/1991 | Hakkinen |
| 5,069,205 A | 12/1991 | Urso |
| 5,074,297 A | 12/1991 | Venegas |
| 5,080,092 A | 1/1992 | Tenna |
| D323,908 S | 2/1992 | Holister et al. |
| 5,109,839 A | 5/1992 | Blasdell et al. |
| 5,109,840 A | 5/1992 | Daleiden |
| 5,113,857 A | 5/1992 | Dickerman et al. |
| 5,117,818 A | 6/1992 | Palfy |
| 5,121,745 A | 6/1992 | Israel |
| 5,121,746 A | 6/1992 | Sikora |
| 5,127,397 A | 7/1992 | Kohnke |
| 5,133,347 A | 7/1992 | Huennebeck |
| 5,137,017 A | 8/1992 | Salter |
| 5,138,722 A | 8/1992 | Urella et al. |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| 5,181,506 A | 1/1993 | Tardiff, Jr. et al. |
| D333,015 S | 2/1993 | Farmer et al. |
| 5,188,101 A | 2/1993 | Tumolo |
| D334,633 S | 4/1993 | Rudolph |
| 5,207,665 A | 5/1993 | Davis et al. |
| 5,220,699 A | 6/1993 | Farris |
| 5,222,478 A | 6/1993 | Scarberry et al. |
| 5,231,983 A | 8/1993 | Matson et al. |
| 5,233,978 A | 8/1993 | Callaway |
| 5,243,709 A | 9/1993 | Sheehan et al. |
| 5,243,971 A | 9/1993 | Sullivan et al. |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |
| 5,267,557 A | 12/1993 | Her-Mou |
| 5,269,296 A | 12/1993 | Landis |
| 5,271,391 A | 12/1993 | Graves |
| 5,279,289 A | 1/1994 | Kirk |
| 5,280,784 A | 1/1994 | Kohler |
| 5,299,448 A | 4/1994 | Maryyanek |
| 5,299,579 A | 4/1994 | Gedeon et al. |
| 5,299,599 A | 4/1994 | Farmer et al. |
| 5,304,146 A | 4/1994 | Johnson et al. |
| 5,311,862 A | 5/1994 | Blasdell et al. |
| 5,322,057 A | 6/1994 | Raabe et al. |
| D349,586 S | 8/1994 | Handke |
| 5,335,656 A | 8/1994 | Bowe et al. |
| 5,343,878 A | 9/1994 | Scarberry et al. |
| 5,349,949 A | 9/1994 | Schegerin |
| 5,353,789 A | 10/1994 | Schlobohm |
| 5,355,878 A | 10/1994 | Griffiths et al. |
| 5,355,893 A | 10/1994 | Mick et al. |
| 5,357,951 A | 10/1994 | Ratner |
| 5,364,367 A | 11/1994 | Banks et al. |
| 5,372,130 A | 12/1994 | Stern et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,388,571 A | 2/1995 | Roberts et al. |
| 5,391,248 A | 2/1995 | Brain |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,404,871 A | 4/1995 | Goodman et al. |
| 5,419,318 A | 5/1995 | Tayebi |
| 5,425,359 A | 6/1995 | Liou |
| 5,429,126 A | 7/1995 | Bracken |
| 5,429,683 A | 7/1995 | Le Mitouard |
| 5,431,158 A | 7/1995 | Tirotta |
| 5,437,267 A | 8/1995 | Weinstein et al. |
| 5,438,981 A | 8/1995 | Starr et al. |
| 5,441,046 A | 8/1995 | Starr et al. |
| D362,061 S | 9/1995 | McGinnis et al. |
| 5,462,528 A | 10/1995 | Roewer |
| 5,477,852 A | 12/1995 | Landis et al. |
| 5,479,920 A | 1/1996 | Piper et al. |
| 5,488,948 A | 2/1996 | Dubruille et al. |
| 5,492,116 A | 2/1996 | Scarberry et al. |
| 5,501,214 A | 3/1996 | Sabo |
| 5,503,147 A | 4/1996 | Bertheau |
| 5,509,404 A | 4/1996 | Lloyd et al. |
| 5,509,409 A | 4/1996 | Weatherholt |
| 5,513,634 A | 5/1996 | Jackson |
| 5,513,635 A | 5/1996 | Bedi |
| 5,517,986 A | 5/1996 | Starr et al. |
| 5,526,806 A | 6/1996 | Sansoni |
| 5,533,506 A | 7/1996 | Wood |
| 5,538,000 A | 7/1996 | Rudolph |
| 5,538,001 A | 7/1996 | Bridges |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,684 A | 11/1996 | Behr |
| 5,570,689 A | 11/1996 | Starr et al. |
| D377,089 S | 12/1996 | Starr et al. |
| 5,592,938 A | 1/1997 | Scarberry et al. |
| 5,608,647 A | 3/1997 | Rubsamen et al. |
| 5,623,923 A | 4/1997 | Bertheau et al. |
| 5,642,726 A | 7/1997 | Owens et al. |
| 5,642,730 A | 7/1997 | Baran |
| 5,647,355 A | 7/1997 | Starr et al. |
| 5,647,356 A | 7/1997 | Osendorf et al. |
| 5,647,357 A | 7/1997 | Barnett et al. |
| 5,649,532 A | 7/1997 | Griffiths |

(56) References Cited

U.S. PATENT DOCUMENTS

| | | |
|---|---|---|
| 5,649,533 A | 7/1997 | Oren |
| 5,653,228 A | 8/1997 | Byrd |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,660,171 A | 8/1997 | Kimm et al. |
| 5,662,101 A | 9/1997 | Ogden et al. |
| 5,666,946 A | 9/1997 | Langenback |
| 5,676,133 A | 10/1997 | Hickle et al. |
| 5,682,881 A | 11/1997 | Winthrop et al. |
| 5,685,296 A | 11/1997 | Zdrojkowski |
| 5,687,715 A | 11/1997 | Landis et al. |
| D389,238 S | 1/1998 | Kirk, III et al. |
| 5,704,345 A | 1/1998 | Berthon-Jones et al. |
| 5,707,342 A | 1/1998 | Tanaka |
| 5,715,814 A | 2/1998 | Ebers |
| 5,724,965 A | 3/1998 | Handke et al. |
| 5,735,272 A | 4/1998 | Dillon et al. |
| 5,740,799 A | 4/1998 | Nielsen |
| 5,746,201 A | 5/1998 | Kidd |
| 5,752,509 A | 5/1998 | Lachmann et al. |
| 5,752,511 A | 5/1998 | Simmons et al. |
| 5,778,872 A | 7/1998 | Fukunaga et al. |
| 5,782,774 A | 7/1998 | Shmulewitz |
| 5,794,615 A | 8/1998 | Estes |
| 5,794,619 A | 8/1998 | Edelman et al. |
| 5,807,341 A | 9/1998 | Heim |
| 5,813,423 A | 9/1998 | Kirchgeorg |
| 5,832,918 A | 11/1998 | Pantino |
| 5,842,469 A | 12/1998 | Rapp et al. |
| 5,884,624 A | 3/1999 | Barnett et al. |
| 5,887,587 A | 3/1999 | Groenke |
| 5,906,203 A | 5/1999 | Klockseth et al. |
| 5,918,598 A | 7/1999 | Belfer et al. |
| 5,921,239 A | 7/1999 | McCall et al. |
| D412,745 S | 8/1999 | Scheu |
| 5,935,136 A | 8/1999 | Hulse et al. |
| 5,937,445 A | 8/1999 | Ravo et al. |
| 5,937,851 A | 8/1999 | Serowski et al. |
| 5,954,049 A | 9/1999 | Foley et al. |
| 5,970,975 A | 10/1999 | Estes et al. |
| 5,975,079 A | 11/1999 | Hellings et al. |
| 6,003,511 A | 12/1999 | Fukunaga et al. |
| 6,006,748 A | 12/1999 | Hollis |
| 6,016,804 A | 1/2000 | Gleason et al. |
| 6,019,101 A | 2/2000 | Cotner et al. |
| 6,026,811 A | 2/2000 | Settle |
| 6,039,044 A | 3/2000 | Sullivan |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,102,040 A | 8/2000 | Tayebi et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,135,109 A | 10/2000 | Blasdell et al. |
| 6,139,787 A | 10/2000 | Harrison |
| 6,152,137 A | 11/2000 | Schwartz et al. |
| 6,155,253 A | 12/2000 | Gamberini |
| 6,192,886 B1 | 2/2001 | Rudolph |
| 6,193,914 B1 | 2/2001 | Harrison |
| 6,196,223 B1 | 3/2001 | Belfer et al. |
| 6,211,263 B1 | 4/2001 | Cinelli et al. |
| 6,213,125 B1 | 4/2001 | Reese et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Baller et al. |
| 6,328,031 B1 | 12/2001 | Tischer et al. |
| 6,328,038 B1 | 12/2001 | Kessler et al. |
| 6,340,024 B1 | 1/2002 | Brookman et al. |
| 6,341,606 B1 | 1/2002 | Bordewick et al. |
| 6,345,618 B1 | 2/2002 | Hayek |
| 6,347,631 B1 | 2/2002 | Hansen et al. |
| 6,357,440 B1 | 3/2002 | Hansen et al. |
| 6,357,441 B1 | 3/2002 | Kwok et al. |
| 6,358,279 B1 | 3/2002 | Tahi et al. |
| 6,371,110 B1 | 4/2002 | Peterson et al. |
| 6,374,826 B1 | 4/2002 | Gunaratnam et al. |
| 6,397,847 B1 | 6/2002 | Scarberry et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huzen |
| 6,425,395 B1 | 7/2002 | Brewer et al. |
| 6,427,694 B1 | 8/2002 | Hecker et al. |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau et al. |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,626,177 B1 | 9/2003 | Ziaee |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,651,663 B2 | 11/2003 | Barnett et al. |
| D484,237 S | 12/2003 | Lang et al. |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,691,708 B2 | 2/2004 | Kwok et al. |
| 6,701,926 B2 | 3/2004 | Olsen et al. |
| 6,701,927 B2 | 3/2004 | Kwok et al. |
| 6,710,099 B2 | 3/2004 | Cinelli et al. |
| 6,729,333 B2 | 5/2004 | Barnett et al. |
| 6,766,800 B2 | 7/2004 | Chu et al. |
| 6,766,817 B2 | 7/2004 | da Silva |
| 6,772,760 B2 | 8/2004 | Frater et al. |
| 6,776,162 B2 | 8/2004 | Wood |
| 6,776,163 B2 | 8/2004 | Dougill et al. |
| 6,789,543 B2 | 9/2004 | Cannon |
| 6,796,308 B2 | 9/2004 | Gunaratnam et al. |
| 6,805,117 B2 | 10/2004 | Ho et al. |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,851,429 B2 | 2/2005 | Bishop |

(56) References Cited

U.S. PATENT DOCUMENTS

| | | | |
|---|---|---|---|
| 6,860,269 B2 | 3/2005 | Kwok et al. |
| 6,860,270 B2 | 3/2005 | Sniadich |
| 6,871,649 B2 | 3/2005 | Kwok et al. |
| 6,895,965 B2 | 5/2005 | Scarberry et al. |
| 6,907,882 B2 | 6/2005 | Ging et al. |
| 6,914,091 B2 | 7/2005 | Donald et al. |
| 6,918,404 B2 | 7/2005 | Dias da Silva |
| 6,926,004 B2 | 8/2005 | Schumacher |
| 6,938,620 B2 | 9/2005 | Payne, Jr. |
| 6,959,710 B2 | 11/2005 | Barnett et al. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,000,614 B2 | 2/2006 | Lang et al. |
| 7,007,696 B2 | 3/2006 | Palkon et al. |
| 7,011,090 B2 | 3/2006 | Drew et al. |
| 7,018,362 B2 | 3/2006 | Bierman et al. |
| 7,040,321 B2 | 5/2006 | Gobel |
| 7,052,127 B2 | 5/2006 | Harrison |
| 7,066,586 B2 | 6/2006 | da Silva |
| 7,069,932 B2 | 7/2006 | Eaton et al. |
| 7,076,282 B2 | 7/2006 | Munro et al. |
| 7,076,822 B2 | 7/2006 | Pearce |
| 7,080,645 B2 | 7/2006 | Genger et al. |
| 7,093,599 B2 | 8/2006 | Chen |
| 7,100,610 B2 | 9/2006 | Biener et al. |
| 7,101,359 B2 | 9/2006 | Kline et al. |
| 7,107,989 B2 | 9/2006 | Frater et al. |
| 7,114,497 B2 | 10/2006 | Aylsworth et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et |
| 7,237,551 B2 | 7/2007 | Ho et al. |
| 7,243,723 B2 | 7/2007 | Surjaatmadja et al. |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,308,895 B2 | 12/2007 | Wixey et al. |
| 7,318,437 B2 | 1/2008 | Gunaratnam et al. |
| 7,318,439 B2 | 1/2008 | Raje et al. |
| 7,341,060 B2 | 3/2008 | Ging et al. |
| 7,353,826 B2 | 4/2008 | Sleeper et al. |
| 7,441,618 B2 | 10/2008 | Sorg |
| 7,470,256 B2 | 12/2008 | Lampropoulos et al. |
| 7,481,220 B2 | 1/2009 | Meyer et al. |
| 7,520,869 B2 | 4/2009 | Lampropoulos et al. |
| 7,523,754 B2 | 4/2009 | Lithgow et al. |
| 7,562,658 B2 | 7/2009 | Madaus et al. |
| 7,614,401 B2 | 11/2009 | Thompson |
| 7,621,274 B2 | 11/2009 | Sprinkle et al. |
| 7,624,735 B2 | 12/2009 | Ho et al. |
| 7,631,644 B2 | 12/2009 | Ho et al. |
| 7,640,934 B2 | 1/2010 | Zollinger et al. |
| 7,658,189 B2 | 2/2010 | Davidson et al. |
| 7,699,808 B2 | 4/2010 | Marrs et al. |
| 7,703,457 B2 | 4/2010 | Barnett et al. |
| 7,708,017 B2 | 5/2010 | Davidson |
| 7,743,767 B2 | 6/2010 | Ging et al. |
| 7,775,209 B2 | 8/2010 | Biener et al. |
| 7,779,832 B1 | 8/2010 | Ho |
| 7,798,144 B2 | 9/2010 | Kwok et al. |
| 7,814,911 B2 | 10/2010 | Bordewick et al. |
| 7,827,990 B1 | 11/2010 | Melidis et al. |
| 7,856,980 B2 | 12/2010 | Lang et al. |
| 7,900,631 B2 | 3/2011 | Persson |
| 7,931,024 B2 | 4/2011 | Ho et al. |
| 7,942,148 B2 | 5/2011 | Davidson |
| 7,958,893 B2 | 6/2011 | Lithgow et al. |
| 7,971,590 B2 | 7/2011 | Frater et al. |
| 7,997,267 B2 | 8/2011 | Ging et al. |
| 8,042,541 B2 | 10/2011 | Amarasinghe et al. |
| 8,042,542 B2 | 10/2011 | Ging et al. |
| 8,051,850 B2 | 11/2011 | Kwok et al. |
| 8,091,553 B2 | 1/2012 | Bordewick et al. |
| 8,136,524 B2 | 3/2012 | Ging et al. |
| 8,136,525 B2 | 3/2012 | Lubke et al. |
| 8,186,352 B2 | 5/2012 | Gunaratnam et al. |
| 8,210,180 B2 | 7/2012 | Gunaratnam |
| 8,220,459 B2 | 7/2012 | Davidson et al. |
| 8,297,283 B2 | 10/2012 | Hitchcock et al. |
| 8,397,728 B2 | 3/2013 | D'Souza |
| 2001/0020474 A1 | 9/2001 | Hecker et al. |
| 2002/0020416 A1 | 2/2002 | Namey |
| 2002/0029780 A1 | 3/2002 | Frater et al. |
| 2002/0046755 A1 | 4/2002 | DeVoss |
| 2002/0066452 A1 | 6/2002 | Kessler et al. |
| 2002/0069872 A1 | 6/2002 | Gradon et al. |
| 2002/0124849 A1 | 9/2002 | Billette de Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2003/0019495 A1 | 1/2003 | Palkon et al. |
| 2003/0089373 A1 | 5/2003 | Gradon et al. |
| 2003/0168063 A1 | 9/2003 | Gambone et al. |
| 2003/0196655 A1 * | 10/2003 | Ging et al. ............... 128/201.22 |
| 2003/0196656 A1 | 10/2003 | Moore et al. |
| 2003/0196658 A1 | 10/2003 | Ging et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0112385 A1 | 6/2004 | Drew et al. |
| 2004/0118406 A1 | 6/2004 | Lithgow et al. |
| 2004/0127856 A1 | 7/2004 | Johnson |
| 2004/0182398 A1 | 9/2004 | Sprinkle et al. |
| 2004/0211428 A1 | 10/2004 | Jones |
| 2004/0221850 A1 * | 11/2004 | Ging et al. ............... 128/206.27 |
| 2004/0226566 A1 | 11/2004 | Gunaratnam et al. |
| 2005/0005940 A1 | 1/2005 | Gunaratnam |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2005/0257792 A1 | 11/2005 | Wixey et al. |
| 2006/0118117 A1 | 6/2006 | Berthon-Jones et al. |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0207599 A1 | 9/2006 | Busch et al. |
| 2006/0213520 A1 | 9/2006 | Frater et al. |
| 2007/0125384 A1 | 6/2007 | Zollinger et al. |
| 2007/0215161 A1 | 9/2007 | Frater et al. |
| 2007/0221226 A1 | 9/2007 | Hansen |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110464 A1 | 5/2008 | Davidson et al. |
| 2008/0110469 A1 | 5/2008 | Weinberg |
| 2008/0178886 A1 | 7/2008 | Lieberman et al. |
| 2008/0200880 A1 | 8/2008 | Kyvik et al. |
| 2008/0257354 A1 | 10/2008 | Davidson et al. |
| 2008/0302365 A1 | 12/2008 | Cohen |
| 2009/0044808 A1 | 2/2009 | Guney et al. |
| 2009/0139526 A1 | 6/2009 | Melidis et al. |
| 2009/0173343 A1 | 7/2009 | Omura et al. |
| 2009/0217929 A1 | 9/2009 | Kwok et al. |
| 2009/0223518 A1 | 9/2009 | Kwok et al. |
| 2010/0000534 A1 | 1/2010 | Kooij et al. |
| 2010/0000543 A1 | 1/2010 | Berthon-Jones |
| 2010/0018534 A1 | 1/2010 | Veliss et al. |

(56) References Cited

U.S. PATENT DOCUMENTS

| | | |
|---|---|---|
| 2010/0089401 A1 | 4/2010 | Lang et al. |
| 2010/0132717 A1 | 6/2010 | Davidson et al. |
| 2010/0192955 A1 | 8/2010 | Biener et al. |
| 2010/0282265 A1 | 11/2010 | Melidis et al. |
| 2010/0319700 A1 | 12/2010 | Ng et al. |
| 2011/0056497 A1 | 3/2011 | Scheiner et al. |
| 2011/0220110 A1 | 9/2011 | Frater et al. |
| 2011/0220114 A1 | 9/2011 | Lithgow et al. |
| 2012/0174928 A1 | 7/2012 | Raje et al. |
| 2012/0266886 A1 | 10/2012 | Davidson et al. |
| 2013/0037033 A1 | 2/2013 | Hitchcock et al. |

FOREIGN PATENT DOCUMENTS

| | | |
|---|---|---|
| CN | 1735439 | 2/2006 |
| DE | 185 017 | 5/1907 |
| DE | 30 11 900 | 10/1980 |
| DE | 146 688 | 1/1981 |
| DE | 31 49 449 | 10/1982 |
| DE | 37 19 009 | 12/1988 |
| DE | 39 27 038 | 2/1991 |
| DE | 42 33 448 | 4/1993 |
| DE | 196 03 949 | 8/1997 |
| DE | 297 23 101 | 7/1998 |
| DE | 197 03 526 | 8/1998 |
| DE | 199 44 242 | 3/2001 |
| DE | 100 02 571 | 7/2001 |
| DE | 199 62 515 | 7/2001 |
| DE | 102 13 905 | 10/2002 |
| DE | 10 2004 055 433 | 11/2004 |
| DE | 103 31 837 | 1/2005 |
| DE | 20 2004 018 108 | 2/2005 |
| DE | 103 38 169 | 3/2005 |
| EP | 0 288 937 | 11/1988 |
| EP | 0 334 555 | 9/1989 |
| EP | 0 427 474 | 5/1991 |
| EP | 0 466 960 | 1/1992 |
| EP | 0 303 090 B1 | 4/1992 |
| EP | 0 658 356 | 6/1995 |
| EP | 0 747 078 | 12/1996 |
| EP | 0 776 679 | 6/1997 |
| EP | 0 853 962 | 7/1998 |
| EP | 1 099 452 | 5/2001 |
| EP | 1 118 346 A2 | 7/2001 |
| EP | 1 205 205 | 5/2002 |
| EP | 1 258 266 | 11/2002 |
| EP | 1 334 742 | 8/2003 |
| EP | 1 356 841 A2 | 10/2003 |
| EP | 1 356 843 | 10/2003 |
| EP | 1 360 971 | 11/2003 |
| EP | 1 481 702 | 12/2004 |
| EP | 2 471 566 | 7/2012 |
| EP | 2 471 567 | 7/2012 |
| FR | 2 720 280 | 12/1995 |
| FR | 2 823 122 | 10/2002 |
| GB | 532 214 | 1/1941 |
| GB | 649 689 | 1/1951 |
| GB | 2 176 404 | 12/1986 |
| GB | 2 368 533 | 5/2002 |
| GB | 2 385 533 | 5/2003 |
| JP | S51-142793 | 11/1976 |
| JP | H03-007173 | 1/1991 |
| JP | H11-000397 | 1/1999 |
| JP | H11-104256 | 4/1999 |
| JP | 2000-515784 | 11/2000 |
| JP | 2003-175106 | 6/2003 |
| JP | 2003-535657 | 12/2003 |
| JP | 2004-000570 | 1/2004 |
| JP | 2005-337371 | 12/2005 |
| JP | 2005-537906 | 12/2005 |
| JP | 3802872 | 7/2006 |
| WO | WO 82/03548 | 10/1982 |
| WO | WO 87/01950 | 4/1987 |
| WO | WO 92/20392 | 11/1992 |
| WO | WO 92/20395 | 11/1992 |
| WO | WO 96/28207 | 9/1996 |
| WO | WO 98/03145 | 1/1998 |
| WO | WO 98/04310 | 2/1998 |
| WO | WO 98/12965 | 4/1998 |
| WO | WO 98/23305 | 6/1998 |
| WO | WO 98/34665 | 8/1998 |
| WO | WO 98/48878 | 11/1998 |
| WO | WO 99/16327 | 4/1999 |
| WO | WO 99/25410 | 5/1999 |
| WO | WO 99/43375 | 9/1999 |
| WO | WO 99/61088 | 12/1999 |
| WO | WO 00/20072 | 4/2000 |
| WO | WO 00/38772 | 7/2000 |
| WO | WO 00/50121 | 8/2000 |
| WO | WO 00/69521 | 11/2000 |
| WO | WO 00/72905 | 12/2000 |
| WO | WO 00/74758 | 12/2000 |
| WO | WO 00/76568 | 12/2000 |
| WO | WO 00/78384 | 12/2000 |
| WO | WO 01/62326 | 8/2001 |
| WO | WO 01/95965 | 12/2001 |
| WO | WO 01/97892 | 12/2001 |
| WO | WO 01/97893 | 12/2001 |
| WO | WO 02/38221 | 5/2002 |
| WO | WO 02/45784 | 6/2002 |
| WO | WO 03/090827 | 11/2003 |
| WO | WO 03/105921 | 12/2003 |
| WO | WO 2004/007010 | 1/2004 |
| WO | WO 2004/022146 | 3/2004 |
| WO | WO 2004/022147 | 3/2004 |
| WO | WO 2004/041342 | 5/2004 |
| WO | WO 2004/073778 | 9/2004 |
| WO | WO 2004/078230 | 9/2004 |
| WO | WO 2004/096332 | 11/2004 |
| WO | WO 2005/018523 | 3/2005 |
| WO | WO 2005/021075 | 3/2005 |
| WO | WO 2005/028010 | 3/2005 |
| WO | WO 2005/053781 | 6/2005 |
| WO | WO 2005/063328 | 7/2005 |
| WO | WO 2005/086943 | 9/2005 |
| WO | WO 2005/094928 | 10/2005 |
| WO | WO 2005/099801 | 10/2005 |
| WO | WO 2005/110220 | 11/2005 |
| WO | WO 2005/118040 | 12/2005 |
| WO | WO 2005/123166 | 12/2005 |
| WO | WO 2006/014630 | 2/2006 |
| WO | WO 2006/052653 | 5/2006 |
| WO | WO 2006/069345 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/102707 | 10/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/045008 | 4/2007 |
| WO | WO 2007/048174 | 5/2007 |
| WO | WO 2007/053878 | 5/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

Adam J. Singer MD et al. "The Cyanoacrylate Topical Skin Adhesives," American Journal of Emergency Medicine, vol. 26, 2008, pp. 490-496.

Australian Appln. No. 2005253641—Examiner's First Report, dated Apr. 20, 2010.

(56) References Cited

OTHER PUBLICATIONS

Australian Appln. No. 2005253641—Examiner's Report, dated Aug. 18, 2011.
Australian Appln. No. 2006206040—Examination Report, dated Jun. 27, 2012.
Chinese Appln. No. 200580020203.6—Office Action (w/English translation), dated Jun. 1, 2010.
Chinese Appln. No. 200580020203.6—Office Action (w/English translation), dated Jul. 6, 2011.
Chinese Appln. No. 200580020203.6—Office Action (w/English translation), dated Dec. 23, 2011.
Chinese Appln. No. 200580020203.6—Office Action (w/English translation), dated Apr. 18, 2012.
Chinese Appln. No. 200680002169.4—Third Office Action (w/English translation), dated Nov. 11, 2010.
Chinese Appln. No. 200680002169.4—Office Action (w/English translation), dated Mar. 23, 2010.
Chinese Appln. No. 200810109270.0—Office Action (w/English translation), dated Oct. 19, 2011.
Chinese Appln. No. 200810109270.0—Office Action (w/English translation), dated Jun. 27, 2012.
Chinese Appln. No. 201010000226.3—Office Action (w/English translation), dated Apr. 26, 2012.
ComfortLite™, Respironics, http://comfortlite.respironics.com, before Applicant's filing date.
ComfortLite™ 2, Respironics, http://comfortlite2.respironics.com, before Applicant's filing date.
European Appln. No. EP 01944732.5—Office Action, dated Nov. 27, 2009.
European Appln. No. EP 03793493.2—Supplementary Search Report, dated Dec. 2, 2009.
European Appln. No. EP 03793493.2—Office Action, dated Mar. 18, 2011.
European Appln. No. EP 03810331.3—Supplementary Search Report, dated Dec. 18, 2009.
European Appln. No. EP 04802133.1—Supplementary Search Report, dated Sep. 8, 2009.
European Appln. No. EP 04802133.1—Office Action, dated Dec. 22, 2009.
European Appln. No. EP 05746824.1—Supplementary Search Report, dated Dec. 17, 2009.
European Appln. No. EP 05749447.8—Supplementary Search Report, dated Dec. 8, 2009.
European Appln. No. EP 06704287.9—Supplementary Search Report, dated Oct. 6, 2009.
European Appln. No. EP 06704287.9—Office Action, dated Jul. 18, 2011.
European Appln. No. EP 07784697.0—Search Report, dated Jul. 27, 2009.
European Appln. No. EP 07845378.4—Search Report, dated Dec. 1, 2009.
European Appln. No. EP 08154854.7—Extended Search Report, dated Nov. 27, 2008.
European Appln. No. EP 08154854.7—Examination Report, dated Jul. 1, 2011.
European Appln. No. EP 08161249.1—Extended Search Report, dated Mar. 19, 2009.
European Appln .No. EP 09003544.5—Search Report, dated Jun. 2, 2009.
European Appln. No. EP 09161984.1—Extended Search Report, dated Sep. 3, 2009.
European Appln. No. EP 11174401.7—Search Report, dated Oct. 20, 2011.
European Appln. No. EP 11174407.4—Extended Search Report, dated Oct. 20, 2011.
European Appln. No. EP 12154923.2—Extended Search Report, dated Jun. 1, 2012.
European Appln. No. EP 12154926.6—Extended Search Report, dated Jun. 6, 2012.
Fisher and Paykel Col.—Product Family—http://www.fphcare.com/osa/products.asp/, before Applicant's filing date.
Hans Rudolph, Inc.—Mask Products—http://www.rudolphkc.com/products.php?category=MASKS, before Applicant's filing date.
"If You Hate CPAP! You Need CPAP Pro®," www.cpappro.com, before Applicant's filing date.
Japanese Appln. No. 2005-337371—Reasons for Rejection (w/English translation), dated Feb. 22, 2011.
Japanese Appln. No. 2005-337371—Final Office Action (w/English translation), dated Jan. 31, 2012.
Japanese Appln. No. 2007-515732—Office Action (w/English translation), dated Aug. 24, 2010.
Japanese Appln. No. 2007-515732—Office Action (w/English translation), dated Aug. 16, 2011.
Japanese Appln. No. 2007-515732—Office Action (w/English translation), dated Jun. 12, 2012.
Japanese Appln. No. 2007-550636—Office Action (w/English translation), dated Mar. 18, 2011.
Japanese Appln. No. 2007-550636—Office Action (w/English translation), dated Mar. 21, 2012.
Japanese Appln. No. 2007-550636—Notice of Allowance (w/English translation), dated Jul. 10, 2012.
Japanese Appln. No. 2009-140433—Office Action (w/English translation), dated Aug. 20, 2011.
Japanese Appln. No. 2009-140433—Notice of Allowance, dated Sep. 4, 2012.
Japanese Appln. No. 2010-195597—Office Action (w/English translation), dated Jun. 12, 2012.
Japanese Appln. No. 2010-214485—Office Action (w/English translation), dated Jun. 12, 2012.
Japanese Appln. No. 2011-038110—Office Action (w/English translation), dated Aug. 14, 2012.
JP 11-000397A Machine Translation, provided by the Japanese Patent Office, Jan. 6, 2009, full document.
Joel W. Beam, "Tissue Adhesives for Simple Traumatic Lacerations," Journal of Athletic Training, 2008, vol. 43, No. 2, pp. 222-224.
Laurent Brochard, "Pressure Support Ventilation," Chapter 9, Part IV—Conventional Methods of Ventilator Support, pp. 239-257, 1994.
McPherson et al., "Respiratory Therapy Equipment," Chapter 8, Third Edition, Introduction to Ventilators, pp. 230-253, 1985.
Merriam-Webster Online Dictionary definition of moveable from the 14th century, before Applicant's filing date.
New Zealand Appln. No. 597552—Examination Report, dated Jan. 19, 2012.
New Zealand Appln. No. 587820—Examination Report, dated Sep. 13, 2010.
New Zealand Appln. No. 587344—Examination Report, dated Jan. 19, 2012.
New Zealand Appln. No. 587344—Examination Report, dated Aug. 3, 2012.
New Zealand Appln. No. 539836—Examination Report, dated Aug. 25, 2005.
New Zealand Appln. No. 2003275762—Examiner's Report No. 3, dated Nov. 18, 2009.
PCT/AU2003/001163—International Search Report, dated Nov. 4, 2003.
PCT/AU2003/001471—International Search Report, dated Feb. 12, 2004.
PCT/AU2004/001832—International Search Report, dated Mar. 24, 2005.
PCT/AU2004/001832—International Preliminary Report on Patentability, dated Jul. 3, 2006.
PCT/AU2005/000803—International Search Report, dated Jun. 30, 2005.
PCT/AU2005/000850—International Search Report, dated Aug. 12, 2005.
PCT/AU2005/000850—International Preliminary Report on Patentability, dated Dec. 20, 2006.
PCT/AU2006/000032—International Preliminary Report on Patentability, dated Jul. 17, 2007.
PCT/AU2006/000032—International Search Report, dated May 15, 2006.

(56) References Cited

OTHER PUBLICATIONS

PCT/AU2006/000770—International Search Report, dated Aug. 3, 2006.
PCT/AU2007/001051—International Search Report, dated Nov. 5, 2007.
PCT/AU2007/001052—International Search Report, dated Oct. 9, 2007.
PCT/AU2007/001456—International Search Report, dated Dec. 12, 2007.
PCT/AU2007/001936—International Search Report, dated Mar. 4, 2008.
PCT/AU2009/000240—International Search Report, dated May 21, 2009.
PCT/AU2009/000262—International Search Report, dated Jun. 9, 2009.
PCT/AU2009/001144—International Search Report, dated Dec. 8, 2009.
ResMed Co.—Mask Products—http://resmed.com/portal/site/ResMedUS/index.jsp? , before Applicant's filing date.
Respironics Co.—Mask Family—http://masksfamily.respironics.com/, before Applicant's filing date.
Respironics Contour mask with Comfort Flap (released 1993).
Respironics Contour Deluxe mask (released 2000).
Respironics ComfortFull FF mask (released 2003).
SNAPP Nasal Interface, Tiara Medical Systems, Inc.—http://tiaramed.com/asp_shops/shopdisplayproducts.asp?id=109&cat=SNAPP%2A+Nasal+Interface, before Applicant's filing date.
Subbu Venkatraman et al., "Review Skin Adhesives and Skin Adhesion 1. Transdermal Drug Delivery Systems," Biomaterials, vol. 19, 1998, pp. 1119-1136.
Tiara Medical Systems, Inc., "Advantage HUSH Nasal Mask,"?, Tiara Medical Systems, Inc., before Applicant's filing date.
Unsolicited email from Elson Silva, PhD, dated Mar. 28, 2008, "Requesting IDS of US 6,766,817 for patents on fluids moving on porosity by Unsaturated Hydraulic Flow," (email provided in both HTML and plain text format).
U.S. Appl. No. 60/424,686, filed Nov. 8, 2002 (expired).
U.S. Appl. No. 60/483,622, filed Jul. 1, 2003 (expired).
U.S. Appl. No. 60/533,214, filed Dec. 31, 2003 (expired).
U.S. Appl. No. 60/634,802, filed Dec. 10, 2004 (expired).
U.S. Appl. No. 60/643,121, filed Jan. 12, 2005 (expired).
U.S. Appl. No. 60/645,672, filed Jan. 21, 2005 (expired).
U.S. Appl. No. 60/795,615, filed Apr. 28, 2006 (expired).
U.S. Appl. No. 60/833,841, filed Jul. 28, 2006 (expired).
U.S. Appl. No. 60/835,442, filed Aug. 4, 2006 (expired).
U.S. Appl. No. 60/852,649, filed Oct. 19, 2006 (expired).
U.S. Appl. No. 60/874,968, filed Dec. 15, 2006 (expired).
U.S. Appl. No. 60/907,856, filed Apr. 19, 2007 (expired).
U.S. Appl. No. 60/924,241, filed May 4, 2007 (expired).
U.S. Appl. No. 60/929,393, filed Jun. 25, 2007 (expired).
U.S. Appl. No. 60/935,179, filed Jul. 30, 2007 (expired).
U.S. Appl. No. 60/935,336, filed Aug. 8, 2007 (expired).
U.S. Appl. No. 60/996,160, filed Nov. 5, 2007 (expired).
U.S. Appl. No. 61/006,409, filed Jan. 11, 2008 (expired).
U.S. Appl. No. 61/064,818, filed Mar. 28, 2008 (expired).
U.S. Appl. No. 61/071,512, filed May 2, 2008 (expired).
U.S. Appl. No. 61/213,326, filed May 29, 2009 (expired).
U.S. Appl. No. 61/222,711, filed Jul. 2, 2009 (expired).
U.S. Appl. No. 61/263,175, filed Nov. 20, 2009 (expired).
U.S. Appl. No. 61/272,162, filed Aug. 25, 2009 (expired).
U.S. Appl. No. 61/272,250, filed Sep. 4, 2009 (expired).
Webster's New World Dictionary, Third College Edition 1988, definition for engaged and flexible, before Applicant's filing date.
Webster's Third New International Dictionary, 1993, Dictionary definition for adjustable, bendable, and mild steel, before Applicant's filing date.
U.S. Appl. No. 13/676,736, filed Nov. 14, 2012.
U.S. Appl. No. 13/676,869, filed Nov. 14, 2012.
U.S. Appl. No. 13/676,925, filed Nov. 14, 2012.
U.S. Appl. No. 13/687,680, filed Nov. 28, 2012.
U.S. Appl. No. 13/688,575, filed Nov. 29, 2012.
U.S. Appl. No. 13/688,890, filed Nov. 29, 2012.
U.S. Appl. No. 13/688,875, filed Nov. 29, 2012.
U.S. Appl. No. 13/688,931, filed Nov. 29, 2012.
U.S. Appl. No. 13/689,211, filed Nov. 29, 2012.
U.S. Appl. No. 13/689,094, filed Nov. 29, 2012.
U.S. Appl. No. 13/689,210, filed Nov. 29, 2012.
Office Action mailed Jan. 15, 2013 issued in corresponding JP Patent Application No. 2011-185789 (and English translation thereof).
Office Action issued in a related U.S. Appl. No. 12/081,696, dated Feb. 28, 2013.
Office Action issued in a corresponding U.S. Appl. No. 13/537,876, dated Feb. 27, 2013.
Office Action issued in a corresponding U.S. Appl. No. 13/676,736, dated Mar. 26, 2013.
Office Action issued in a corresponding U.S. Appl. No. 13/676,869, dated Mar. 26, 2013.
Office Action issued in a corresponding U.S. Appl. No. 13/676,925, dated Mar. 26, 2013.
Office Action issued in a corresponding U.S. Appl. No. 13/687,680, dated Mar. 26, 2013.
Office Action issued in a corresponding U.S. Appl. No. 13/688,575, dated Apr. 3, 2013.
Office Action issued in a corresponding U.S. Appl. No. 13/688,890, dated Apr. 3, 2013.
Office Action issued in a corresponding U.S. Appl. No. 13/688,875, dated Apr. 2, 2013.
Office Action issued in a corresponding U.S. Appl. No. 13/688,931, dated Mar. 29, 2013.
Office Action issued in a corresponding U.S. Appl. No. 13/689,211, dated Apr. 1, 2013.
Office Action issued in a corresponding U.S. Appl. No. 13/689,094, dated Mar. 29, 2013.
Office Action issued in a corresponding U.S. Appl. No. 13/689,210, dated Apr. 8, 2013.
Office Action issued in a related Chinese Appln. No. 200810109270.0 (Mar. 28, 2013) with English Translation thereof.
U.S. Appl. No. 13/745,077, filed Jan. 22, 2013.
U.S. Appl. No. 13/747,701, filed Jan. 23, 2013.
U.S. Appl. No. 13/747,772, filed Jan. 23, 2013.
U.S. Appl. No. 13/834,189, filed Mar. 15, 2013.
Communication pursuant to Article 94(3) EPC issued in a corresponding European Patent Application No. 12 154 923.2-1662 on Jun. 21, 2013.
First Examination Report issued in a corresponding New Zealand Patent Application No. 612757 on Jul. 11, 2013.
Non-final Office Action issued in related U.S. Appl. No. 12/081,696, dated Sep. 12, 2013.

\* cited by examiner

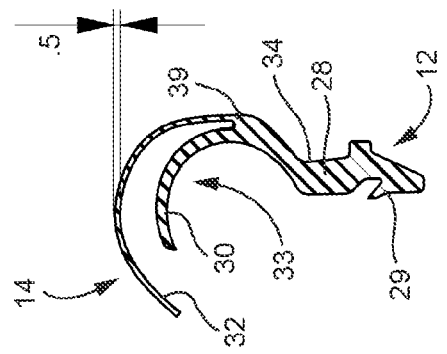
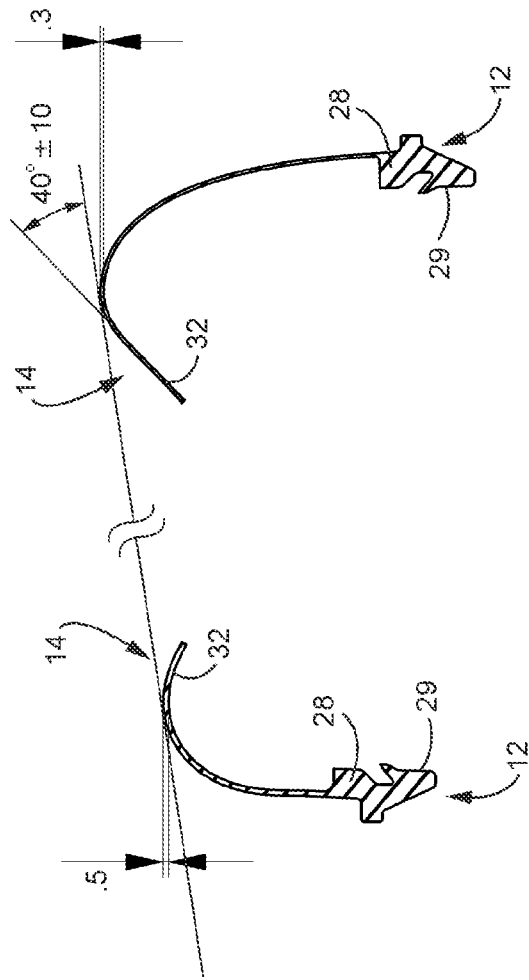
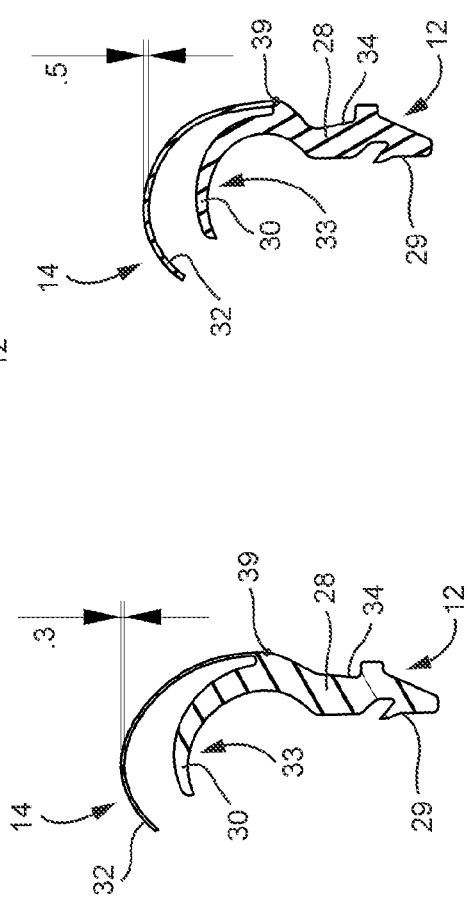

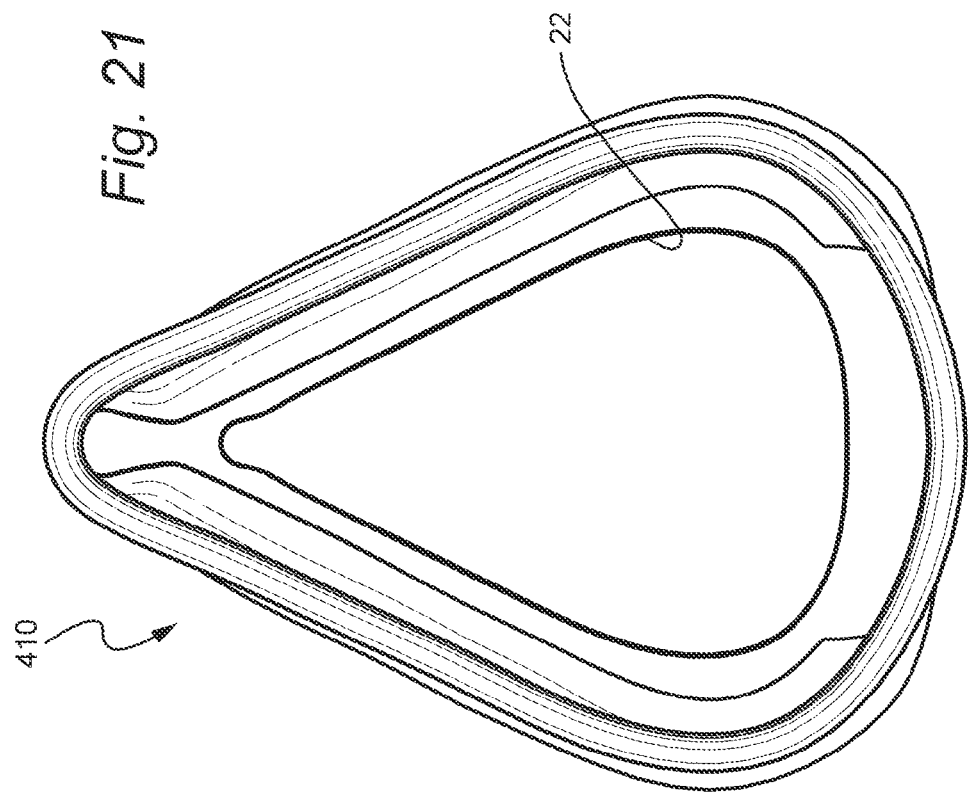
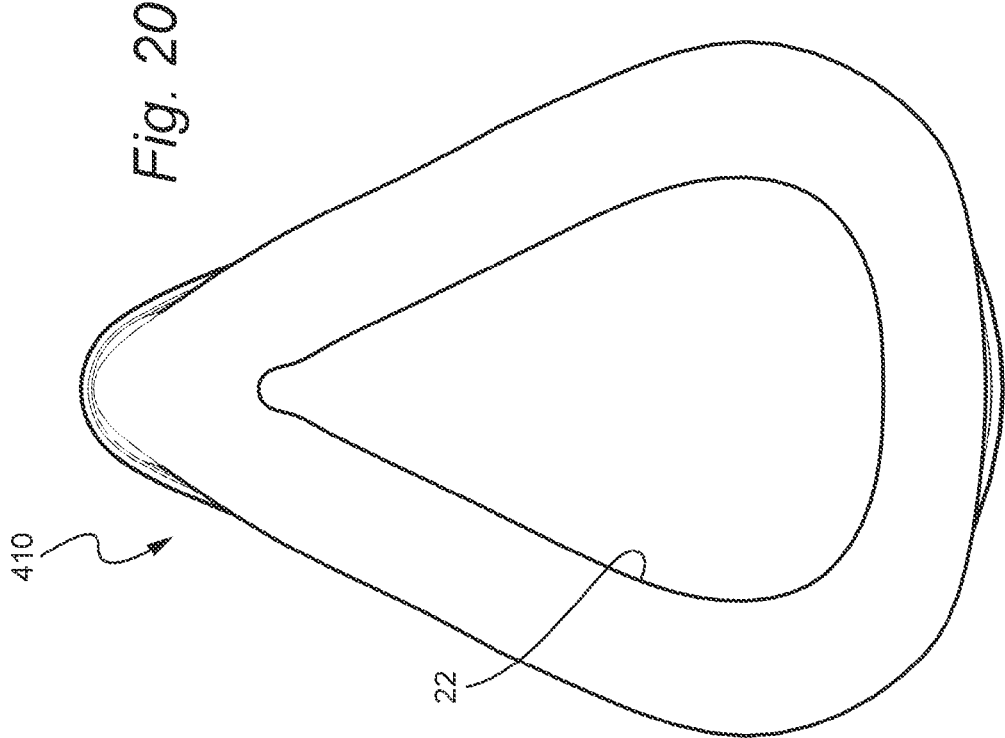

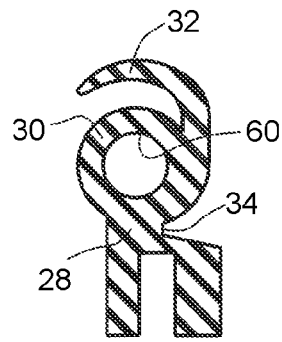
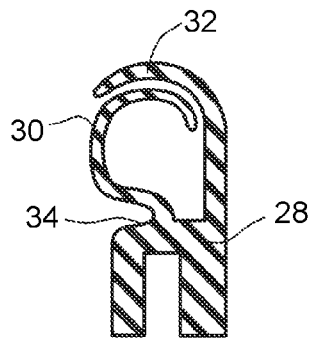
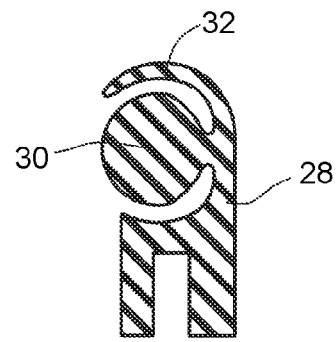
Fig. 30A    Fig. 30B    Fig. 30C
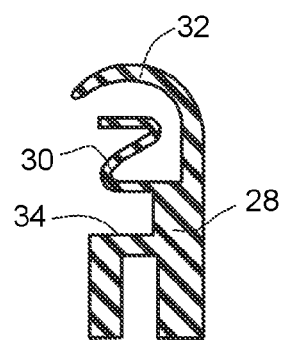
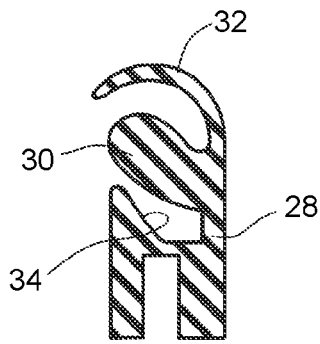
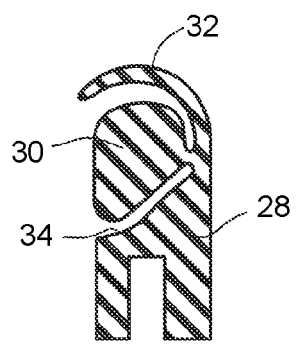
Fig. 30D    Fig. 30E    Fig. 30F
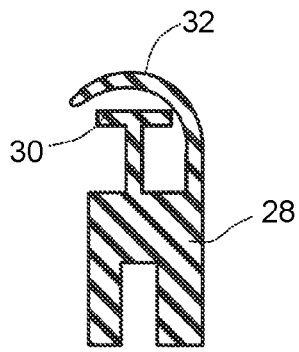
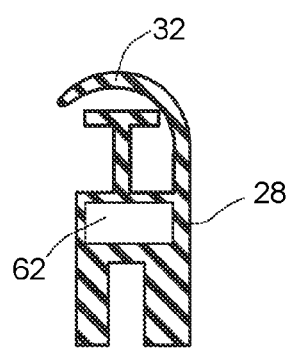
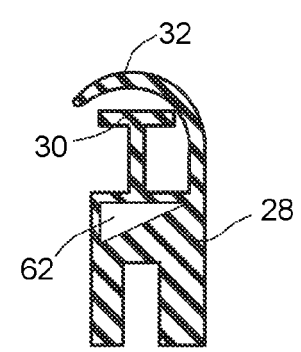
Fig. 30G    Fig. 30H    Fig. 30I a to c = 27.44 mm
a to b = 22.84 mm a to c = 21.9 mm
a to b = 15.1 mm

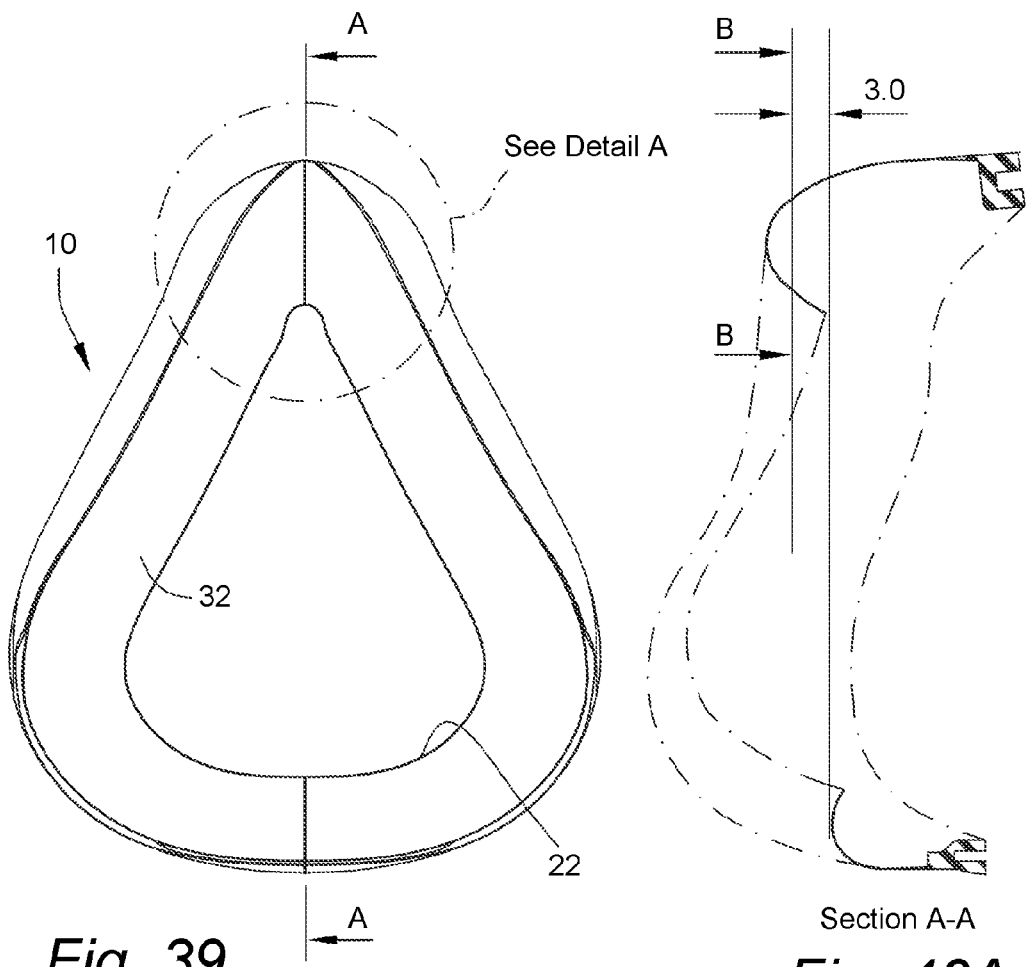
Fig. 39
Fig. 40A
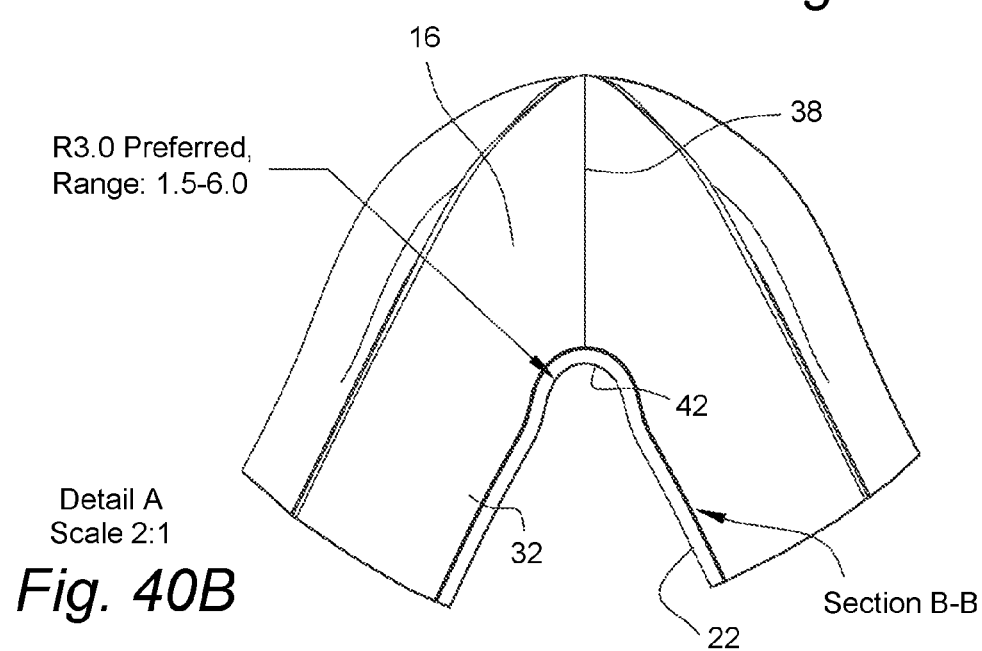
R3.0 Preferred, Range: 1.5-6.0
Detail A
Scale 2:1
Fig. 40B

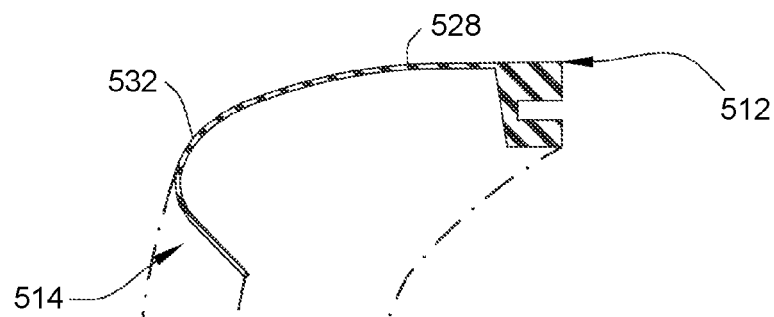
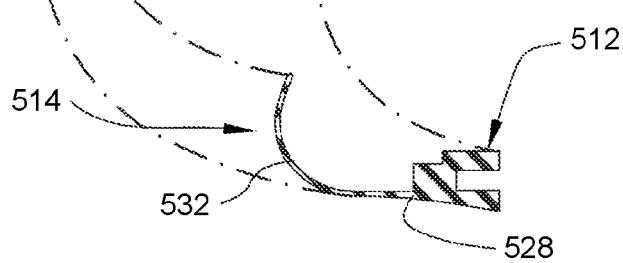
Section C-C
*Fig. 60*
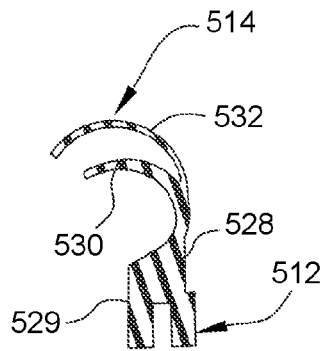
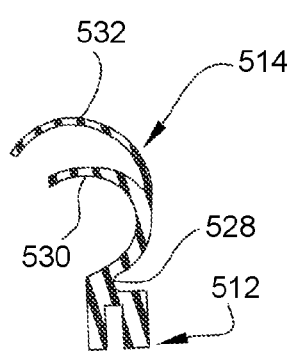
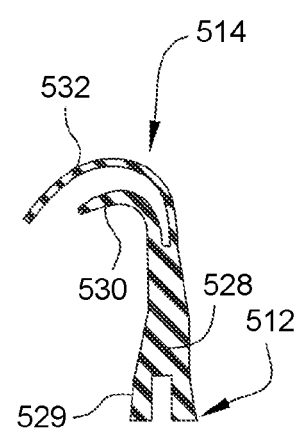
Section D-D
*Fig. 61*
Section F-F
*Fig. 62*
Section E-E
*Fig. 63*

Section C-C

Section A-A

Section B-B

Section C-C

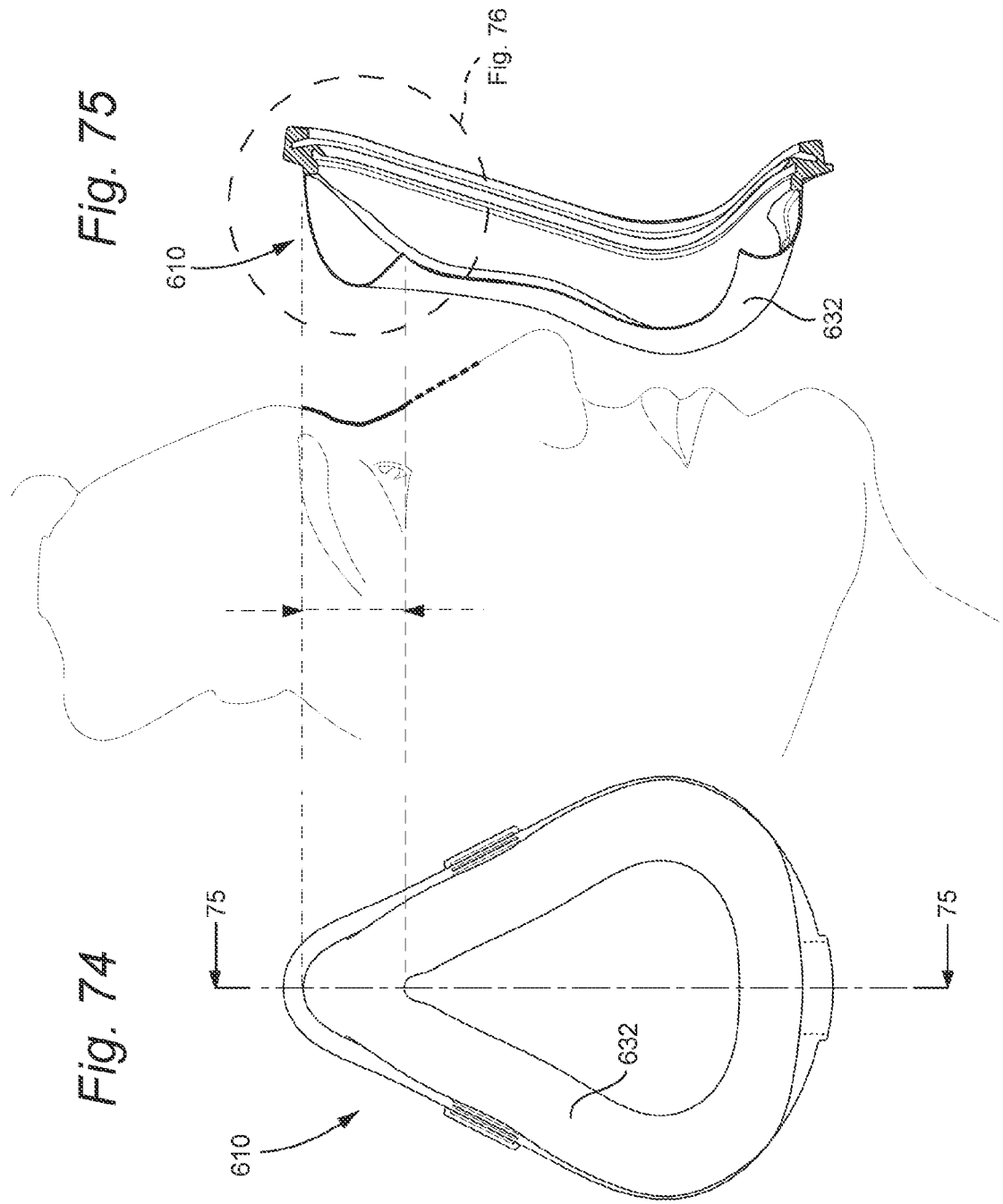

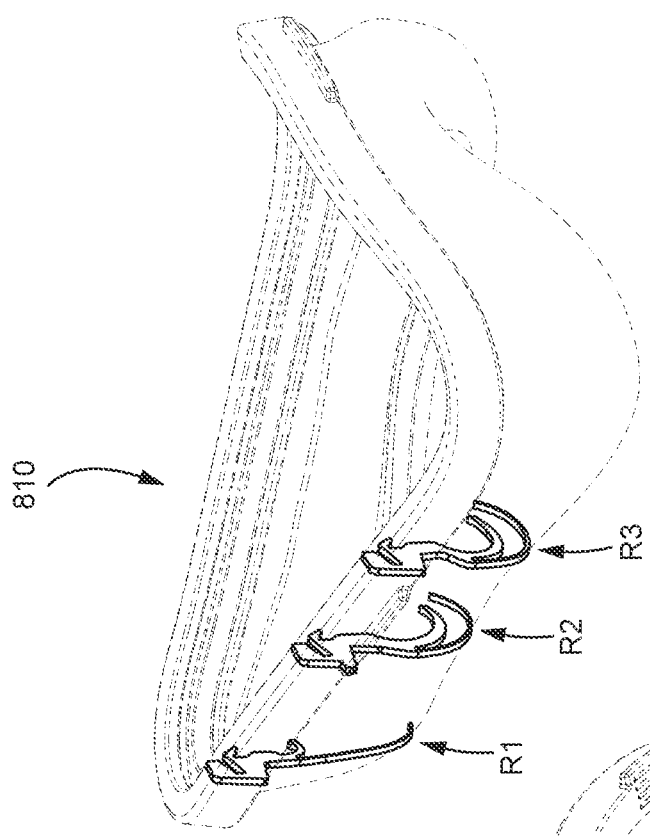
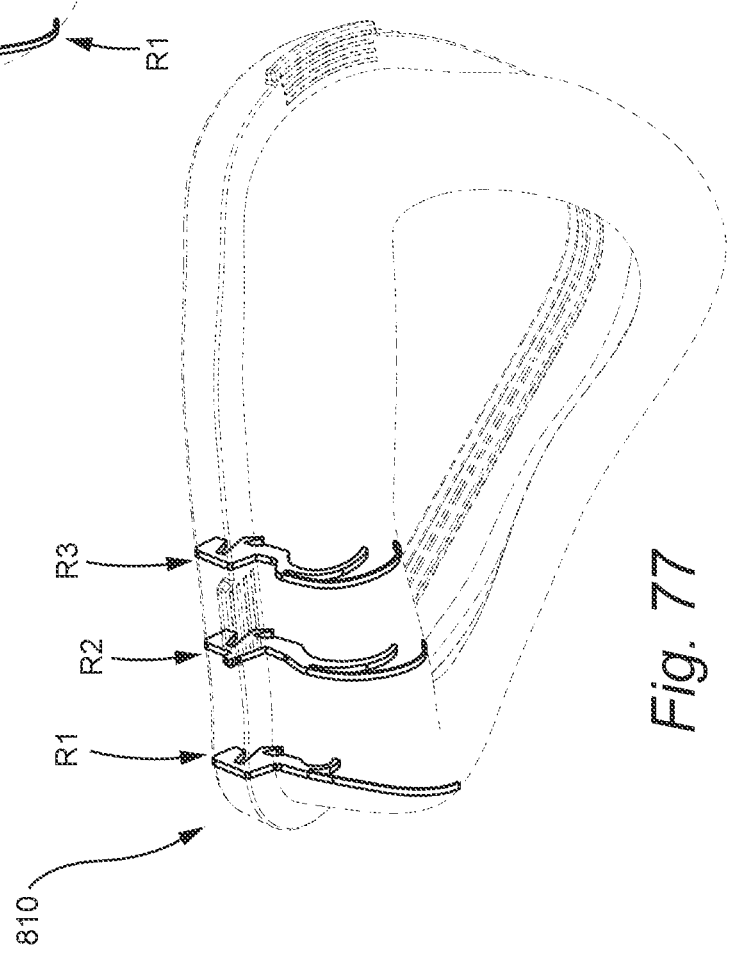

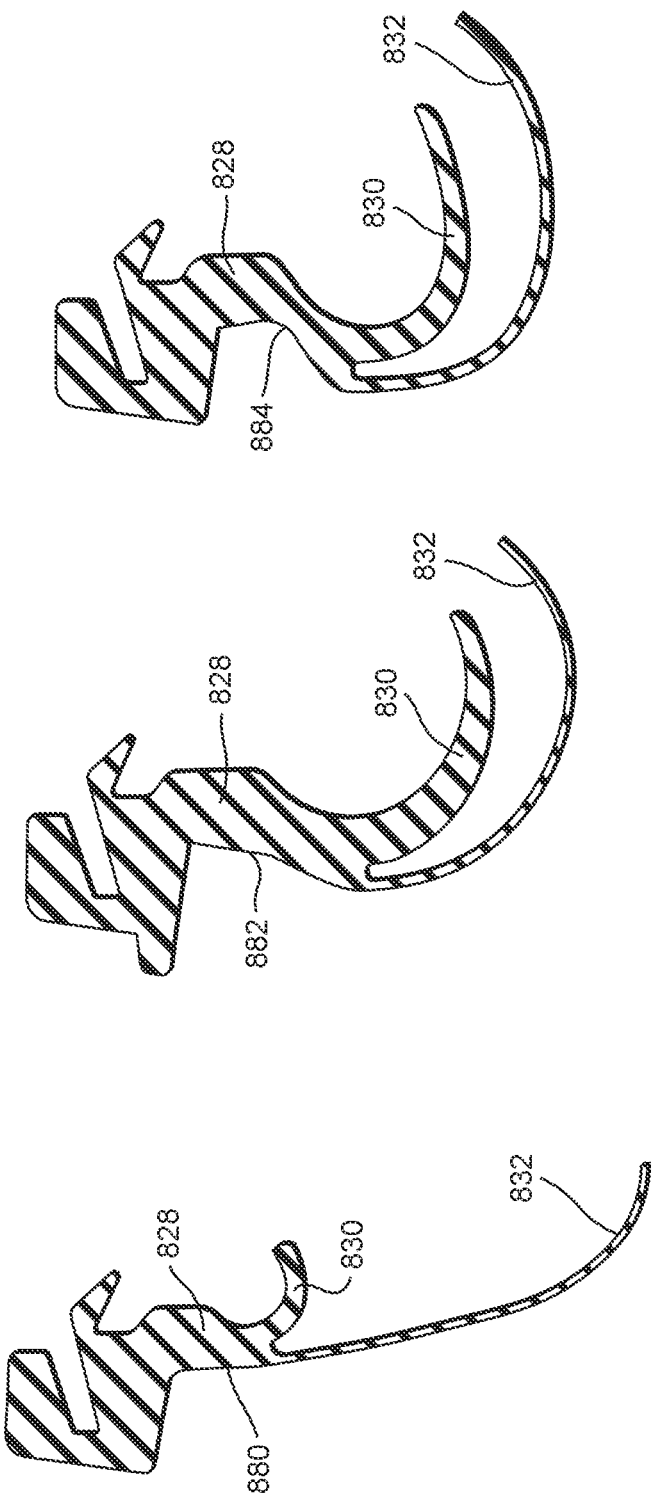

SECTION A-A

SECTION B-B

CUSHION FOR PATIENT INTERFACE

CROSS-REFERENCE TO APPLICATIONS

This application is a continuation of U.S. Ser. No. 13/537,876, filed Jun. 29, 2012, pending, which is a continuation of U.S. Ser. No. 11/793,981, filed Jun. 25, 2007, now U.S. Pat. No. 8,220,459, which is the U.S. national phase of international application PCT/AU2006/000032, filed Jan. 12, 2006, which designated the U.S. and claims the benefit of U.S. Provisional Application Nos. 60/643,130, filed Jan. 12, 2005, and 60/724,303, filed Oct. 7, 2005. Each of the applications mentioned above is incorporated herein by reference in its entirety.

FIELD OF THE INVENTION

The present invention relates to a cushion for a patient interface, the patient interface being used in the treatment, e.g., of Sleep Disordered Breathing (SDB) with Non-Invasive Positive Pressure Ventilation (NPPV).

BACKGROUND OF THE INVENTION

The use of NPPV for treatment of SDB such as Obstructive Sleep Apnea (OSA) was pioneered by Sullivan (see U.S. Pat. No. 4,944,310). Apparatus for the treatment of SDB involves a blower which delivers a supply of air at positive pressure to a patient interface via a conduit. The patient interface may take several forms, such as a nasal mask assembly and a nasal and mouth mask assembly. Patients typically wear a mask assembly while sleeping to receive the NPPV therapy.

Mask assemblies typically comprise a rigid shell or frame and a soft face-contacting cushion. The cushion spaces the frame away from the patient's face. The frame and cushion define a cavity which receives the nose or nose and mouth. The frame and cushion are held in position on the patient's face by a headgear assembly. The headgear assembly typically comprises an arrangement of straps which pass along both sides of the patient's face to the back or crown of the patient's head.

U.S. Pat. No. 5,243,971 (Sullivan and Bruderer) describes a nasal mask assembly for Continuous Positive Airway Pressure (CPAP) having a ballooning/molding seal that conforms with the patient's nose and facial contours. The mask assembly has a face-contacting portion mounted to a shell which is sized and shaped to overfit the nose region of the patient. The face-contacting portion is in the form of a distendable membrane which is molded from an elastic plastic material. The distendable membrane and the shell together define a chamber. Pressurized gas admitted to the chamber causes the membrane to distend outwardly from the patient's face. The contents of this patent are hereby incorporated by reference.

U.S. Pat. No. 6,112,746 (Kwok et al.) describes a nasal mask assembly and a mask cushion therefor. The contents of this patent are hereby incorporated by reference. The cushion comprises a substantially triangularly-shaped frame from which extends a membrane. The frame has an edge by which the cushion is affixed to a mask body. The membrane has an aperture into which the patient's nose is received. The membrane is spaced away from the rim of the frame, and its outer surface is of substantially the same shape as the rim.

The cushion of a patient interface can play a key role in the comfort and effectiveness of therapy. There is considerable variation in facial size and shape which can mean that a mask designed for one type of face may not be suitable for another. For example, an Asian-type nose tends to have a lower nasal bridge whereas a Caucasian-type nose has a higher nasal bridge. Using the wrong cushion can lead to excessive leak and discomfort. While creating customized cushions for every patient may solve some fitting issues, customized masks are very expensive. Thus, manufacturers seek to develop cushions which provide a comfortable and effective seal for a range of facial sizes and shapes.

SUMMARY OF THE INVENTION

One aspect of the invention is to provide a patient interface having a cushion that provides more comfort to the patient while maintaining an effective seal.

Another aspect of the invention is to provide a comfortable cushion for a patient interface which fits a wide range of facial shapes and sizes.

Another aspect of the invention relates to a cushion including an underlying cushion and a membrane, wherein the underlying cushion and the membrane have a substantially flat portion in a nasal region of the cushion.

Another aspect of the invention relates to a cushion including a base wall, an underlying cushion and a membrane, wherein the base wall and underlying cushion have a cross-sectional configuration that provides a variable spring constant around the perimeter of the cushion.

Another aspect of the invention relates to a patient interface wherein the base wall and the frame connection of the cushion are internally offset with respect to the most external cushion point, e.g., external membrane surface.

Another aspect of the invention relates to a cushion including a base wall and underlying cushion that are inclined or angled in a side of nose region of the cushion.

Another aspect of the invention relates to a cushion having a substantially constant mouth width irrespective of its face height.

Another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane includes nasal bridge, cheek, and chin regions adapted to form a continuous seal on nasal bridge, cheek, and chin regions of the patient's face, respectively. The nasal bridge region and adjacent two cheek regions define an intersection or apex. The membrane in the nasal bridge region has a height at the apex or intersection that is greater than a height in an adjacent portion of the cheek region.

Another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. The underlying cushion has a spring-like connection with the base wall. The underlying cushion and/or base wall define a spring constant that varies along a length of the seal.

Another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. One of the membrane and the underlying cushion includes an external surface that defines an outer width of the cushion, and the base wall is internally offset with respect to the external surface.

Yet another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane includes at least nasal bridge and side of nose regions adapted to form a continuous seal on nasal bridge and side of nose regions of the patient's face, respectively. The base wall and the underlying cushion in the side of nose region are inclined or angled with respect to a bottom of the frame.

Yet another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane includes nasal bridge, side of nose, upper cheek, lower cheek and chin regions adapted to form a continuous seal on nasal bridge, side of nose, upper cheek, lower cheek, and chin regions of the patient's face, respectively. An inner edge of the membrane defines an aperture that receives the patient's nose and mouth. A lower portion of the aperture that receives the patient's mouth has a mouth width that remains substantially constant irrespective of a face height of the cushion.

Yet another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. At least a portion of the underlying cushion and/or base wall has a lower portion including a spring configuration that defines displacement of the cushion with respect to a force applied from the frame.

Still another aspect of the invention relates to a method of designing a series of mask assemblies. The method includes providing a first cushion adapted to fit a larger range of patients and providing a second cushion adapted to fit a smaller range of patients. Each of the first and second cushions includes an aperture that receives at least the patient's mouth. The aperture of the first and second cushions have the same width.

Still another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane includes at least a nasal bridge region adapted to form a continuous seal on a nasal bridge region of the patient's face. The membrane forms an elongated ridge in the nasal bridge region. The elongated ridge has sloping sides that meet to form an elongated crest. Each of the sloping sides is angled from a crest centerline in the range of 30-60° and the crest has a radius of curvature in the range of 1.0-5.0 mm.

Still another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane includes at least a nasal bridge region adapted to form a continuous seal on a nasal bridge region of the patient's face. The nasal bridge region of the membrane includes a contoured portion that curves inwardly towards a cavity of the cushion along a radius to terminate at an inner edge of the membrane. The contoured portion has a free end that is angled with respect to a face contacting plane of the cushion in the range of 30-50°.

Still another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. The underlying cushion and/or base wall has a question-mark or sickle shape.

Still another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. The underlying cushion has an arcuate configuration including an arc length greater than 16 mm.

Still another aspect of the invention relates to a cushion for a patient interface that delivers breathable gas to a patient. The cushion includes a base wall structured to be connected to a frame, an underlying support cushion extending away from the base wall towards the patient's face in use, and a membrane provided to substantially cover at least a portion of the underlying cushion. The membrane is adapted to form a continuous seal on the patient's face. The membrane includes a thickness that varies along a length of the seal.

Still another aspect of the invention relates to a cushion for a patient interface that delivers breathable gas to a patient. The cushion includes a base wall structured to be connected to a frame and a membrane adapted to form a continuous seal on the patient's face. At least a portion of the base wall includes a tapered portion that tapers towards the membrane.

Still another aspect of the invention relates to a mask system including a set of at least two cushions arranged to suit different face sizes, wherein the at least two cushions have substantially the same width.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 10-14 are cross-sectional views through the cushion shown in FIG. 5;

FIGS. 20-21 illustrates still another size of the cushion shown in FIGS. 1-9;

FIGS. 39-40B are front and cross-sectional views of an embodiment of the cushion shown in FIGS. 1-9, and showing exemplary dimensions of an embodiment according to the present invention;

FIGS. 59-63 are cross-sectional views through the cushion shown in FIG. 54;

FIGS. 72-76 illustrate a cushion for a patient interface according to another embodiment of the present invention;

FIGS. 77-83 illustrate a cushion for a patient interface according to another embodiment of the present invention;

DETAILED DESCRIPTION OF ILLUSTRATED EMBODIMENTS

FIGS. 1-14 illustrate a cushion 10 constructed according to an embodiment of the present invention. The cushion 10 is adapted to be removably or permanently connected (e.g., via mechanical and/or adhesive fastening) to a frame of a patient interface structured to deliver breathable gas to a patient. In an embodiment, the cushion 10 may be co-molded to a frame of a patient interface. In another embodiment, the cushion may form part of a frame with an outer support structure, e.g., ResMed's Hospital Nasal Mask. The cushion 10 provides a seal with the patient's face during use.

In the illustrated embodiment, the cushion 10 forms a part of a full-face mask. Specifically, the cushion 10 provides a seal around the patient's nose and mouth to enable the delivery of breathable gas to the patient's nose and mouth. However, aspects of the present invention may be applicable to other breathing arrangements, e.g., a nasal mask, a mouth mask, etc. The cushion 10 may be used with a gusset as described in U.S. patent application Ser. No. 10/655,622, incorporated herein by reference in its entirety.

The cushion 10 is structured to provide a more comfortable fit for a wide range of facial shapes and sizes. Also, the cushion 10 is structured to provide a better seal and reduce the risk of leakage as discussed below.

As illustrated in FIGS. 1-14, the cushion 10 includes a non-face-contacting portion 12 structured to be connected to a frame of the patient interface, e.g., via a friction-fit, a tongue-and-groove arrangement, etc., and a face-contacting portion 14 structured to engage the patient's face.

Figure 1:
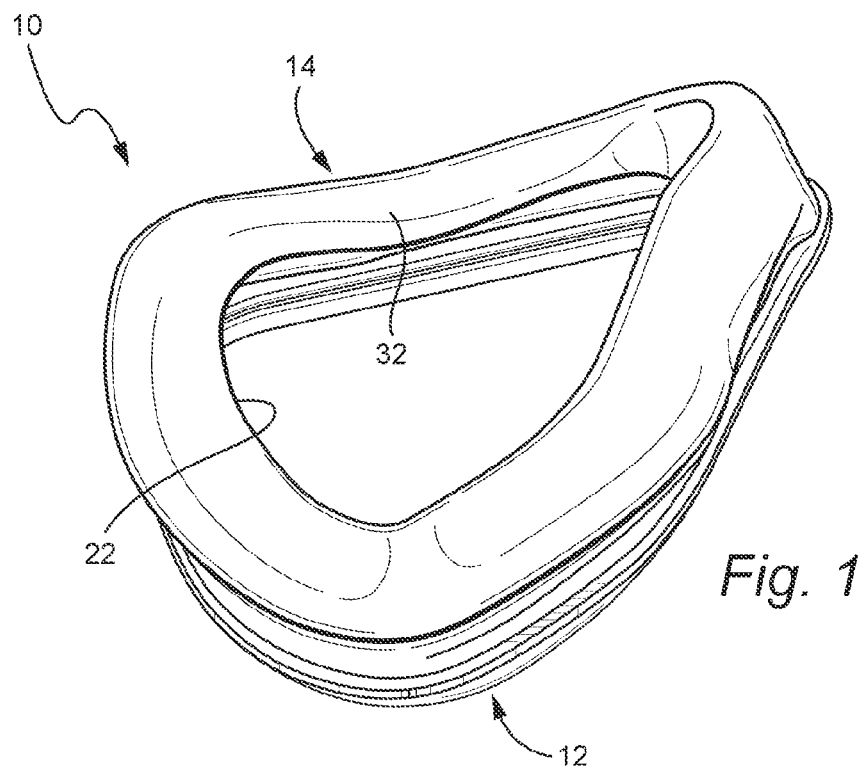
FIGS. 1-9 illustrate a cushion for a patient interface constructed according to an embodiment of the present invention and showing exemplary dimensions of an embodiment.
Figure 2:
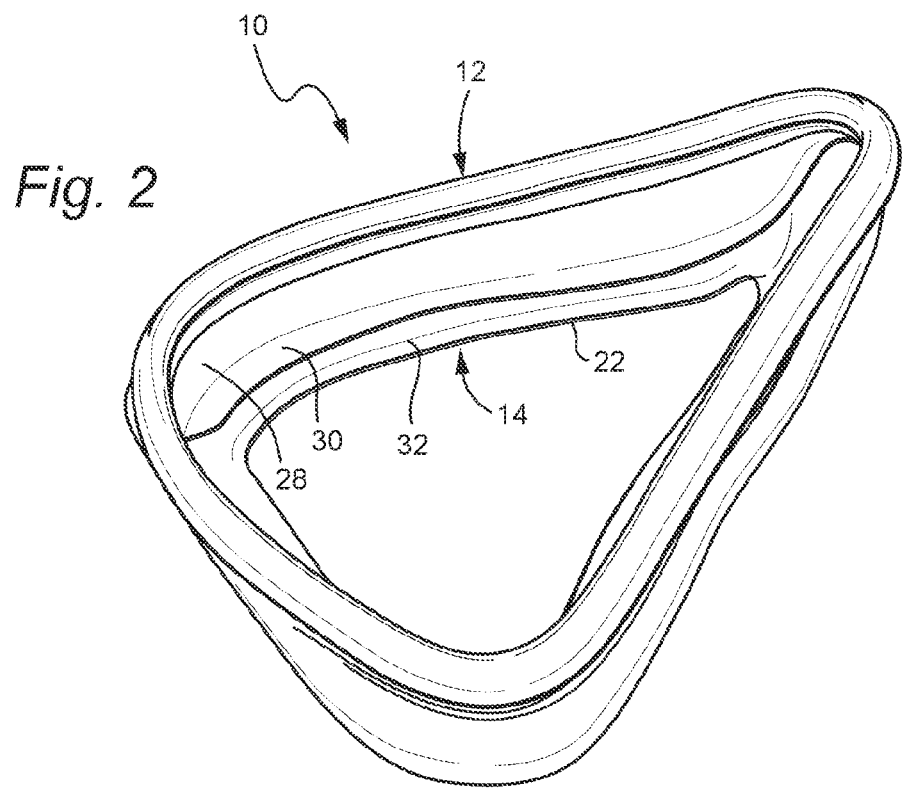
Figure 3:
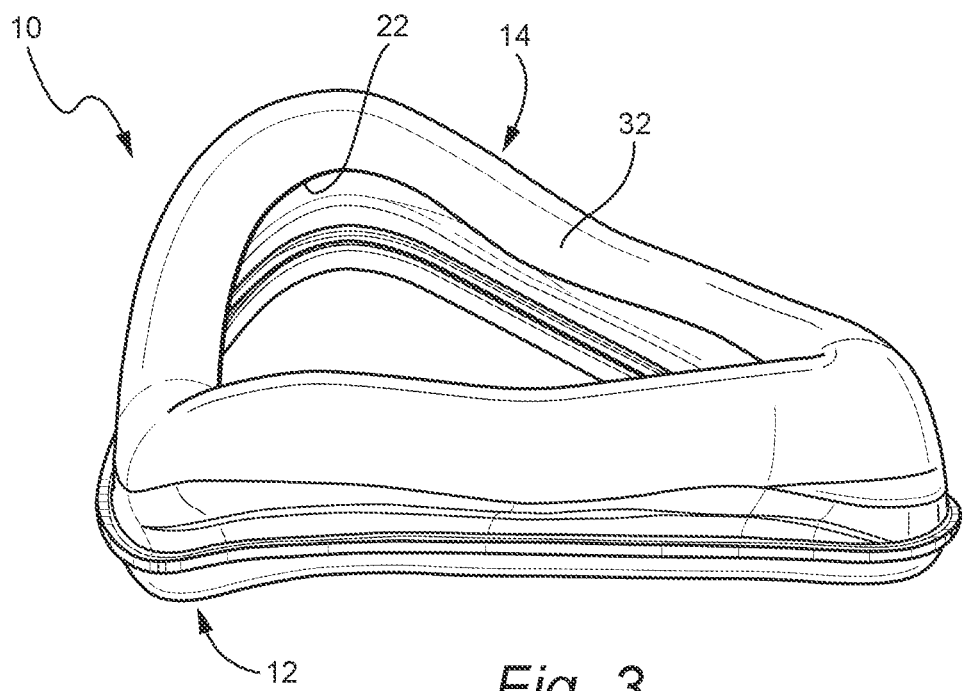
Figure 4:
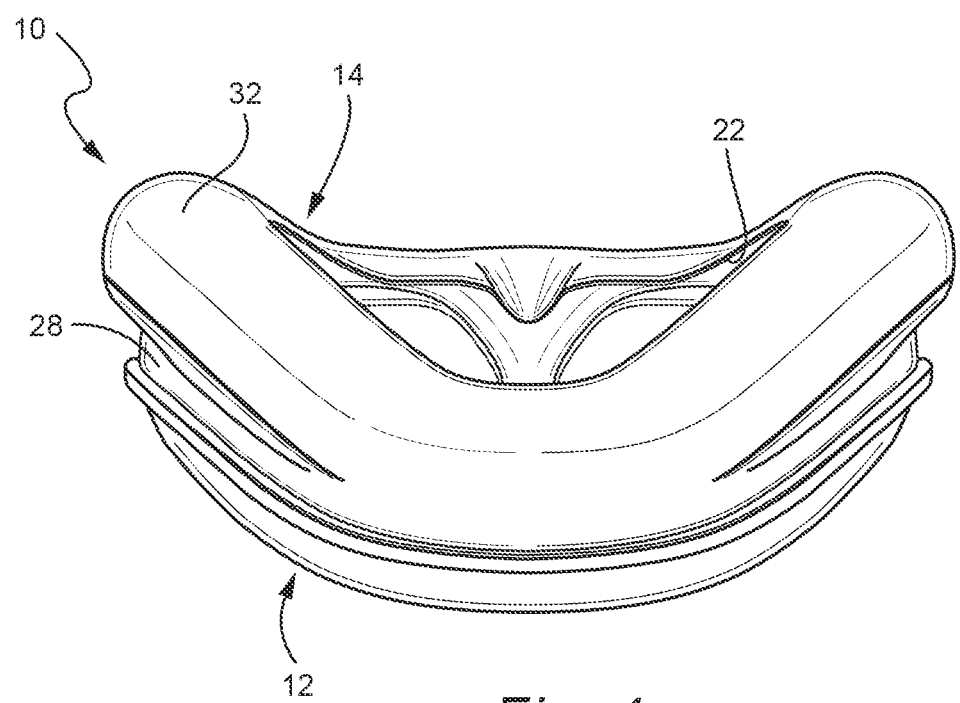
Figure 5:
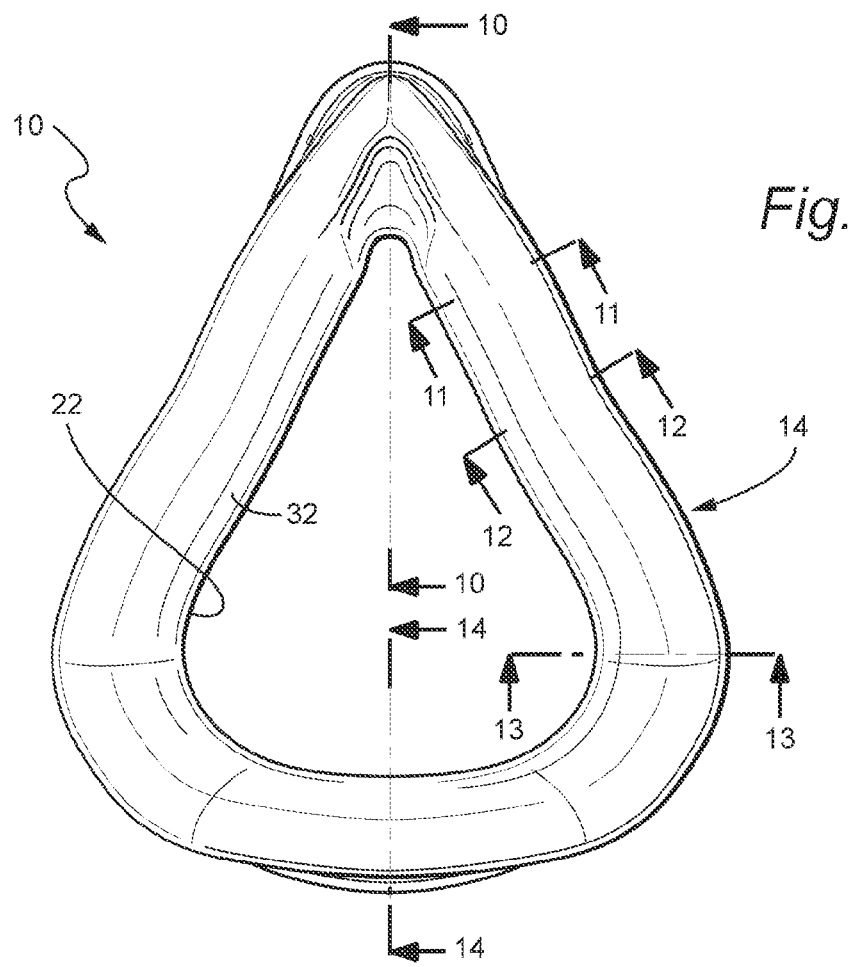
Figure 6:
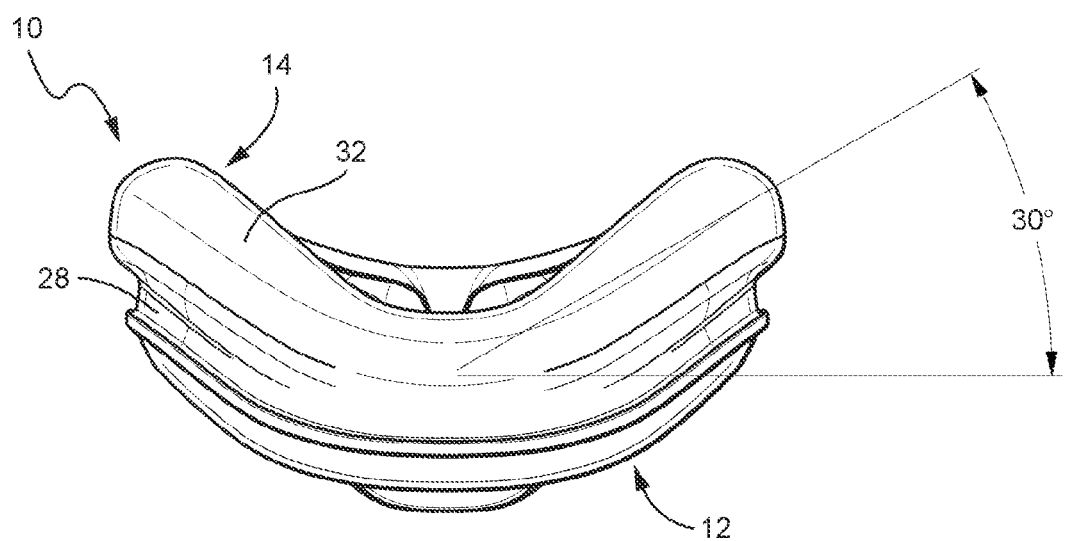
Figure 7:
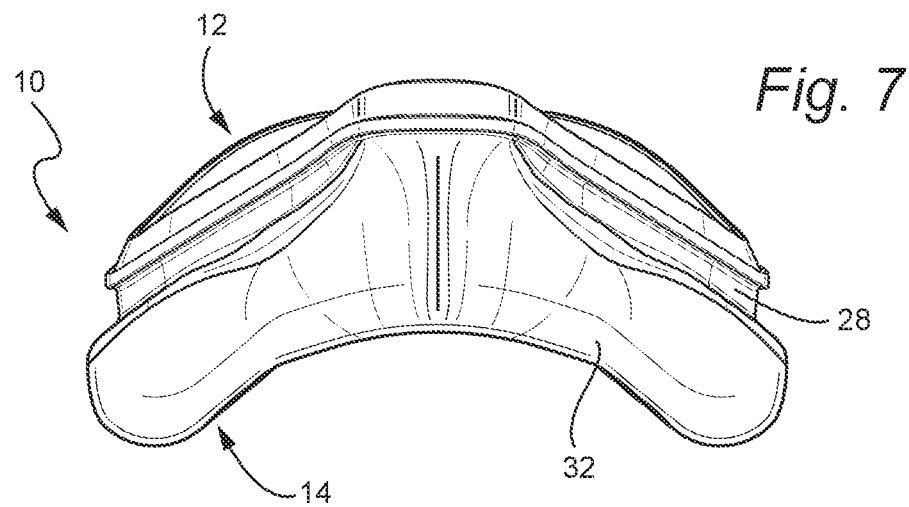
Figure 8:
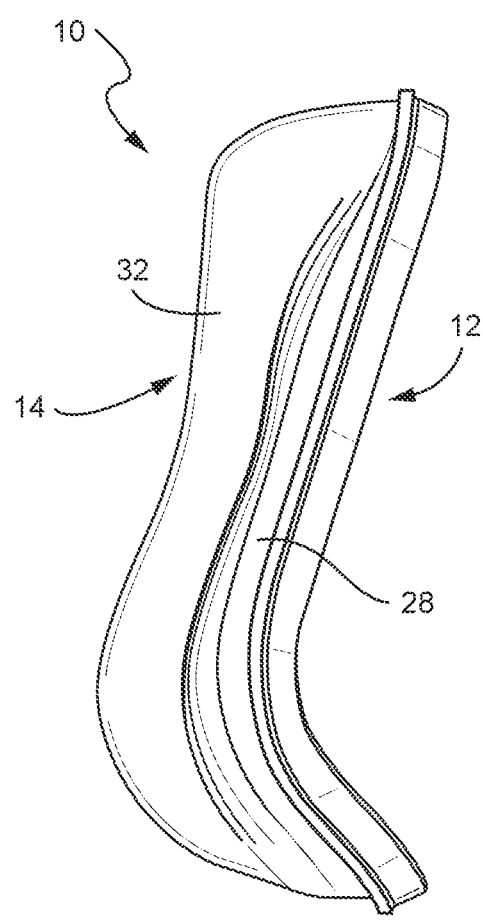
Figure 9:
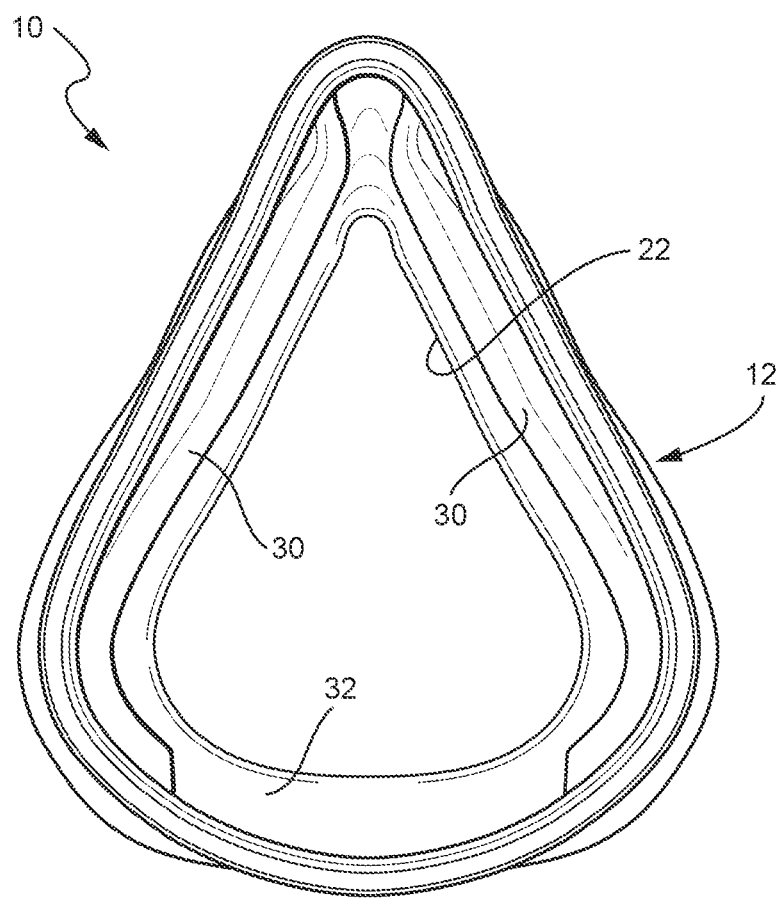
Figure 15:
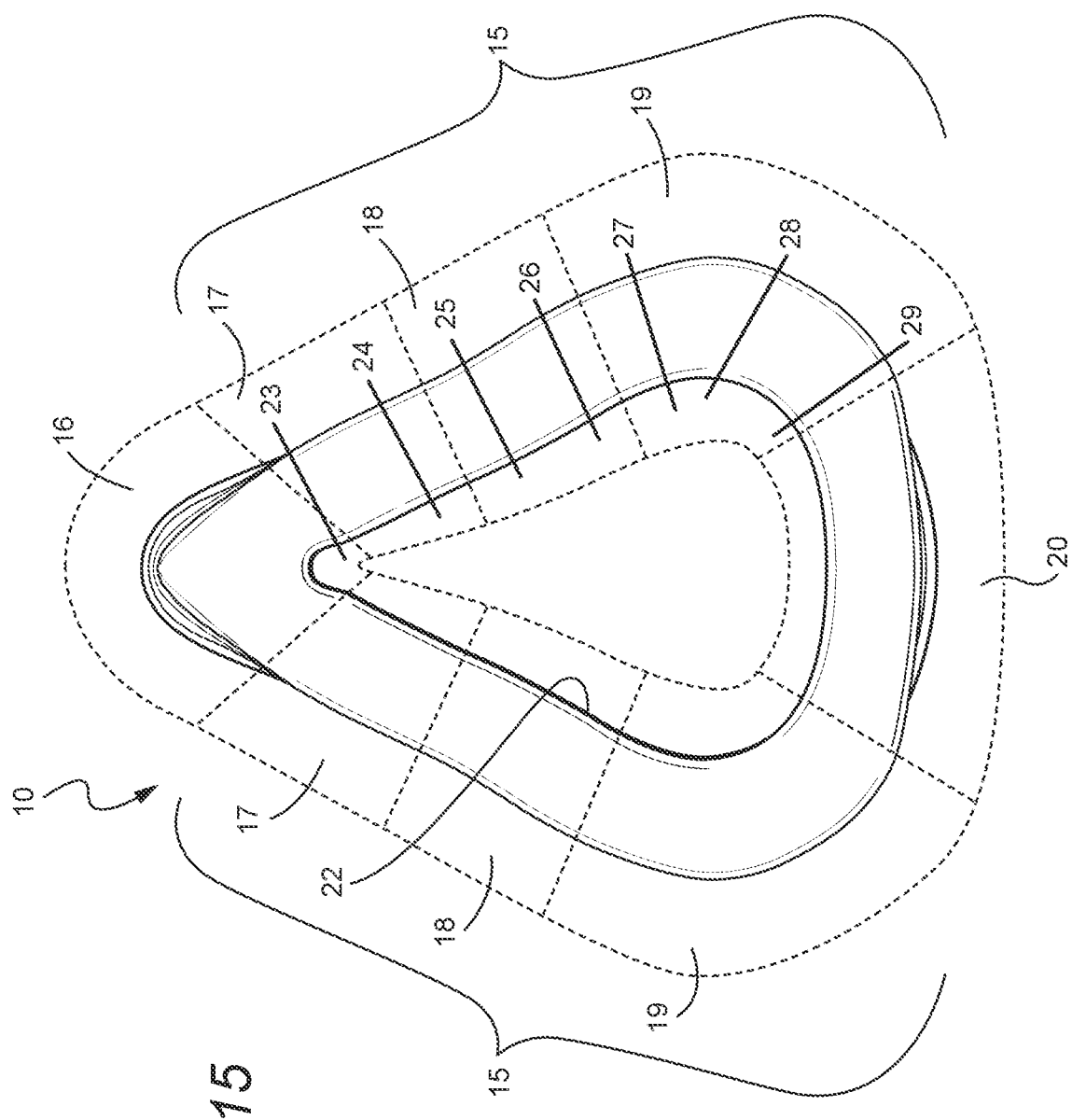
FIG. 15 is a front view of the cushion shown in FIGS. 1-9 that illustrates various regions of the cushion.
Figure 17:
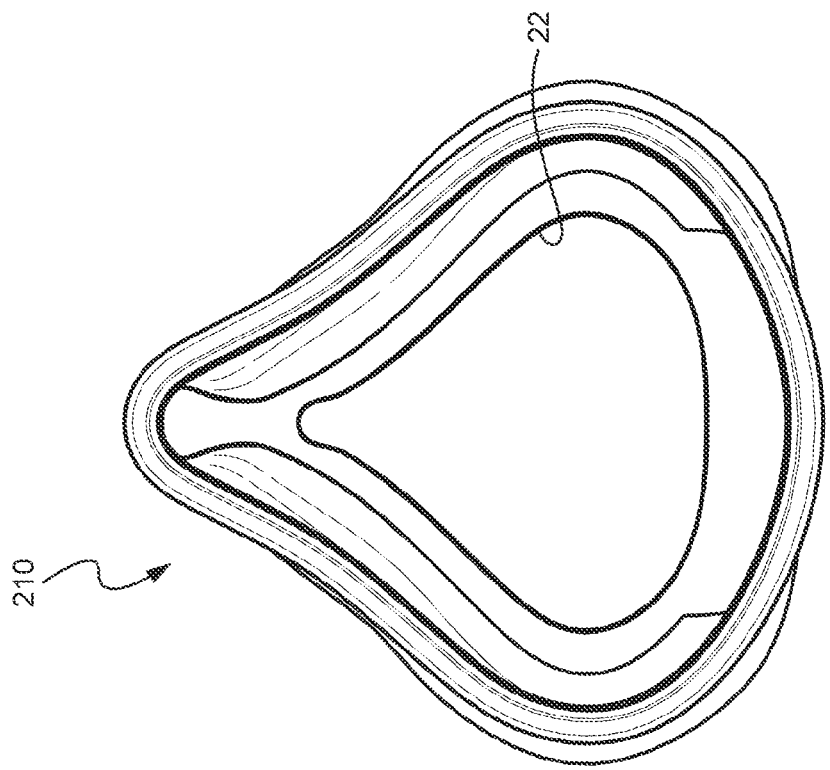
FIGS. 16-17 illustrates another size of the cushion shown in FIGS. 1-9.
Figure 16:
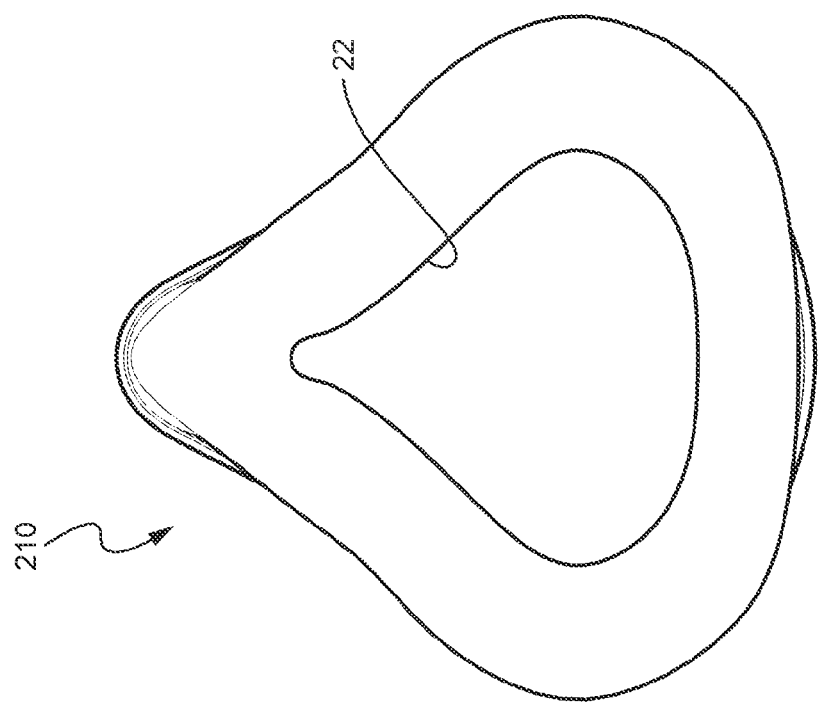
Figure 19:
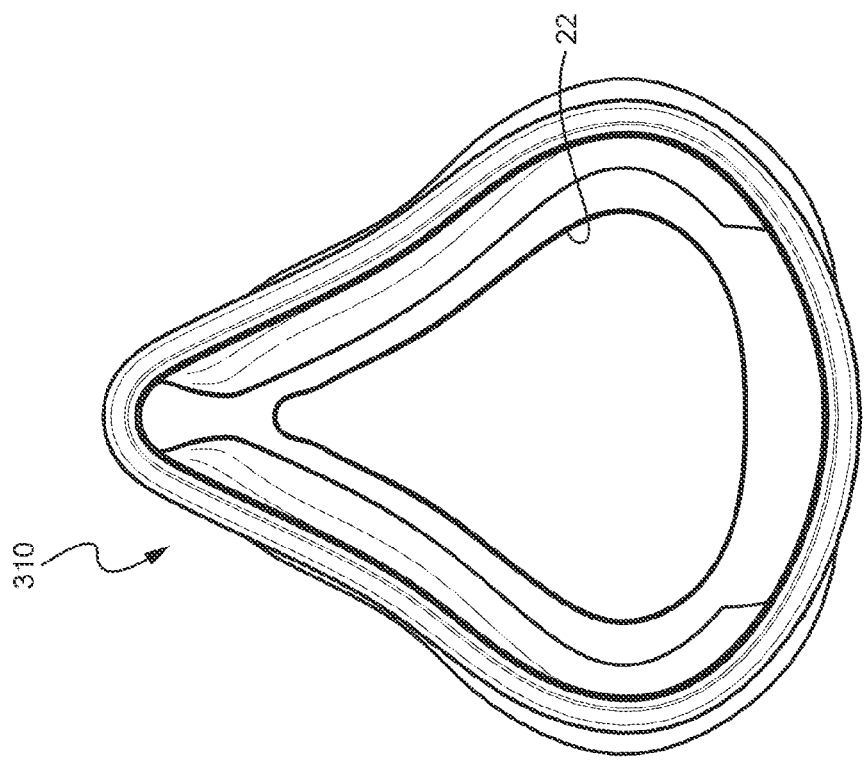
FIGS. 18-19 illustrates yet another size of the cushion shown in FIGS. 1-9.
Figure 18:
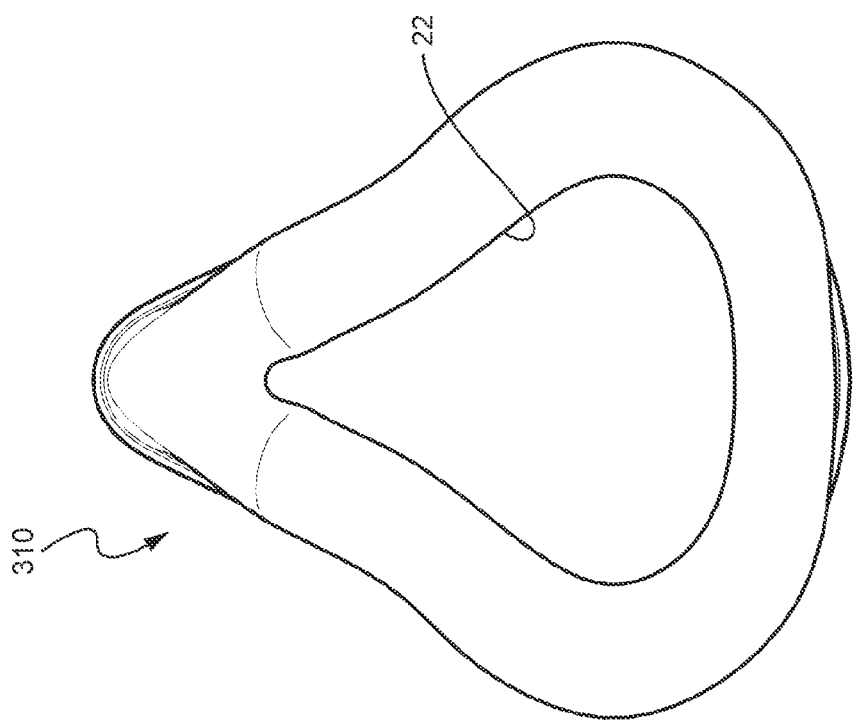
Figure 23:
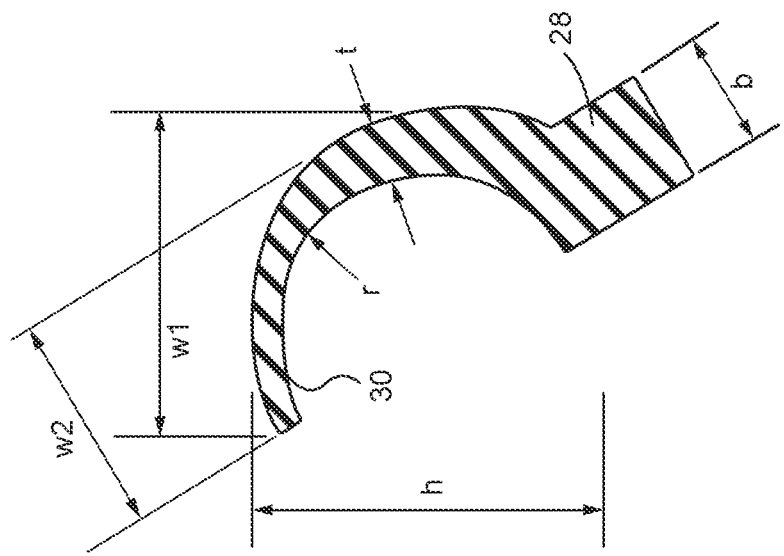
FIGS. 23-29 are cross-sectional views through the cushion shown in FIG. 15 and showing exemplary parameters of an embodiment, the cross-sectional views illustrating the underlying cushion only.

As best shown in FIGS. 5 and 15, the face-contacting portion 14 of the cushion 10 preferably has a generally triangular shape and is structured to continuously contact nasal bridge, side of nose, upper cheek, lower cheek, and chin regions of the patient. However, the face-contacting portion 14 may have other suitable shapes, e.g., a generally trapezoidal shape. In the illustrated embodiment, as best shown in FIG. 15, the cushion 10 includes a nasal bridge region 16 to provide a seal along the patient's nasal bridge, a pair of cheek regions 15 to provide a seal along the patient's nose, cheek, and mouth, and a chin region 20 to provide a seal along the patient's chin. The pair of cheek regions 15 may be further defined as a pair of side of nose regions 17 to provide a seal along the sides of the patient's nose, a pair of upper cheek regions 18 to provide a seal along upper cheeks of the patient, and a pair of lower cheek regions 19 to provide a seal along the patient's lower cheeks and the sides of the patient's mouth.

Width of Cushion in Lower Cheek Regions and Ratio of Face Width to Height Across Mask Sizes The cushion 10 may be provided in various sizes in order to accommodate various facial sizes. For example, FIGS. 16-21 illustrate embodiments of the cushion 10 in three other sizes. In an embodiment, the cushion 210 shown in FIGS. 16-17 may represent a extra small size, the cushion 310 shown in FIGS. 18-19 may represent a small size, the cushion 10 shown in FIGS. 1-14 may represent a medium size, and the cushion 410 shown in FIGS. 20-21 may represent a large size. As illustrated, the mouth width of the cushions 10, 210, 310, 410 are substantially constant irrespective of their face height.

Specifically, the cushion 10 defines an aperture 22 that receives the patient's mouth. In a preferred embodiment, the lower portion of the aperture 22 has a constant width for all cushion sizes, e.g., 60 mm. However, the width of the lower portion of the aperture 22 may be almost constant, e.g., in a range of 5 mm, for all cushion sizes. For example, the width of the lower portion of the aperture 22 of the cushion 10 may be 60 mm±5. In contrast, the width of the lower portion of the aperture 722 of a known cushion 700 commercially sold under the name of UltraMirage® Full Face by ResMed Ltd. is 60 mm for a large size, 54 mm for a medium size, and 52 mm for a small size. The UltraMirage® cushion 700 is shown in FIGS. 46-53.

Anthropometric data has indicated that mouth widths for patients with relatively small faces are not necessarily narrower than mouth widths for patients with relatively large faces. Hence, all faces generally have the same mouth width. Thus, the aperture 22 in the cushion 10 is made sufficiently wide to accommodate a wide range of patients and remains constant or almost constant, e.g., a range of 5 mm, regardless of the change in face height of a mask to fit larger faces. This can be seen in the substantially constant cushion geometry around the lower cheek and chin regions of the different cushion sizes, and thus the varying width to height ratios of the different cushion sizes. For example, the lower portion of the aperture 22 of each of the cushions 10, 210, 310, 410 has substantially the same width.

Base Wall, Underlying Cushions, and Membrane

As best shown in FIGS. 9 and 10-14, the face-contacting portion 14 of the cushion 10 includes a base wall 28, a pair of underlying support cushions 30 extending away from the base wall 28, and a membrane 32 provided to substantially cover at least a portion of the underlying cushions 30 and provide a sealing structure for the face contacting portion 14. The base wall 28 and underlying cushions 30 provide a support structure for the membrane 32.

As illustrated, the underlying cushions 30 are preferably provided on lateral sides of the base wall 28 only, e.g., in the side of nose, upper cheek, and lower cheek regions 17, 18, 19, although the underlying cushions 30 could be joined and substantially surround the patient's nose and also the lower lip or chin region. The underlying cushions 30 add rigidity to the membrane 32 at the sides of the patient's mouth and cheeks. While it is preferable that the membrane 32 be thinner than the underlying cushions 30, they could have the same thickness or the membrane could be thicker than the underlying cushion. Also, the elimination of an underlying cushion in the chin region 20 allows the cushion 10 to more deeply engage with the patient's face in this region without subjecting the patient's chin region 20 to excessive pressure. That is, there is no underlying cushion to restrain the movement of the membrane 32 in this region, which may improve the seal in this region and adjacent regions. Additionally, the elimination of an underlying cushion in the chin region 20 enables the cushion 10 to accommodate more facial shapes and provides more flexibility and allows for movement or opening of the mouth.

In the illustrated embodiment, the face-contacting portion 14 of the cushion has a double-walled construction, i.e., membrane 32 and underlying cushion 30, in the side of nose, upper cheek, and lower cheek regions 17, 18, 19, and a single-walled construction, i.e., membrane 32, in the nasal bridge and chin regions 16, 20 as shown in FIGS. 10-14. The single wall construction at the top and bottom of the cushion 10 helps to accommodate high landmarks, e.g., pointed chin, by allowing the center of the cushion 10 to flex. This flexibility accommodates more patients with the same cushion. However, the cushion 10 may have any other suitable construction, e.g., single walled, double walled, triple walled or more walled construction, in any suitable region of the cushion 10, e.g., cheek, chin, nasal bridge. For example, the underlying cushion 30 may extend around the entire perimeter of the cushion 10. Also, the underlying cushion 30 could be completely removed.

As shown in FIGS. 10-14, the membrane thickness may vary in the different regions of the cushion 10. As illustrated, the membrane in the nasal bridge region 16 and upper cheek region 18 is 0.3 mm thick which transitions to 0.5 mm thickness in the upper cheek region 18 and maintains this thickness in the lower cheek and chin regions 19, 20. This arrangement provides greater compliance/stretch across the nasal bridge by providing a thinner membrane. This stretch is not required at the lower regions and here the thicker membrane is less likely to vibrate on the patient face in use.

Internally Offset Base Wall and Frame Connection

Figures 48, 49, 50:
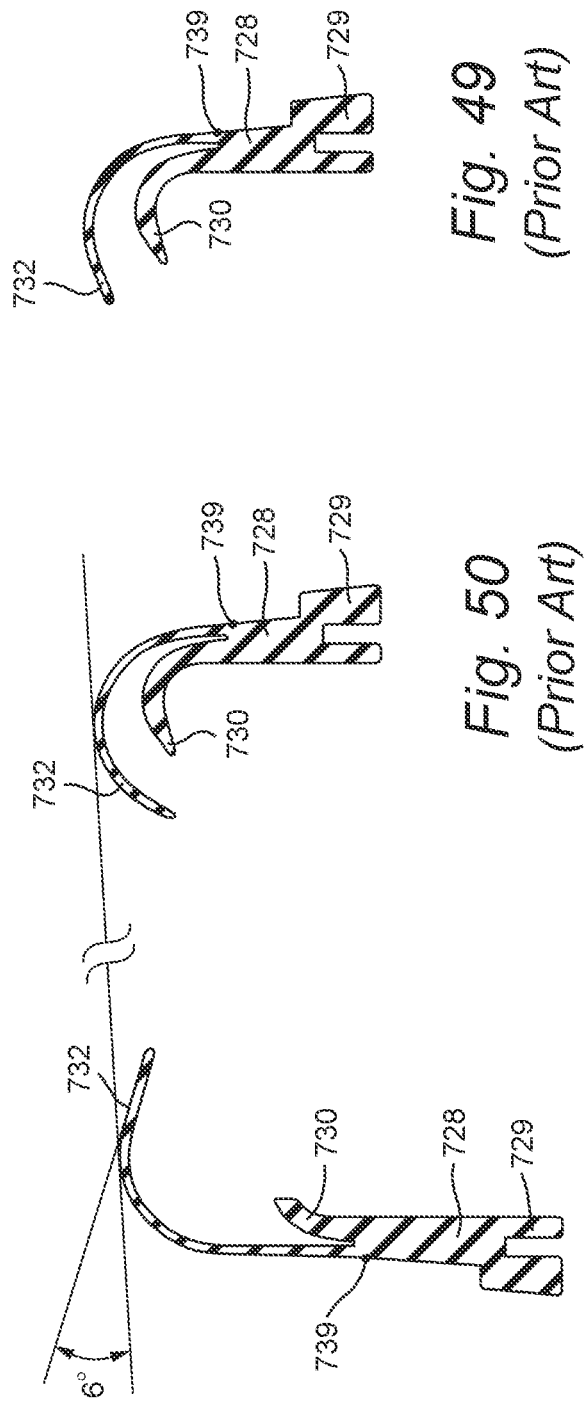
Figure 53:
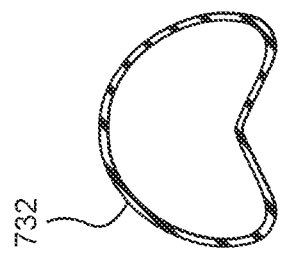

Another aspect of the invention relates to the size and configuration of the base wall 28, underlying cushion 30, and membrane 32 of the cushion 10. FIGS. 48-50 illustrate the base wall 728, underlying cushion 730, and membrane 732 of the UltraMirage® cushion 700. As illustrated, the cushion 10 has a different cross-sectional profile than the UltraMirage® cushion 700.

For example, as best shown in FIGS. 11-13, the base wall 28 and the frame connection 29 are internally offset with respect to the most external cushion point 39, e.g., external surface of membrane or underlying cushion. In contrast, the base wall 728 and frame connection 729 of the UltraMirage® cushion 700 are not offset with respect to the most external cushion point 739 (see FIGS. 48-50). As a result of this inward movement, the base width of the cushion 10 is narrowed, e.g., by about 5 mm or 2.5 mm per base, which provides a less obtrusive cushion and saves material which means less weight and cost. Also, the narrower cushion 10 provides less free length for the cushion 10 to bulge outwardly in use, thus helping to minimize or eliminate leakage.

As illustrated, a lower portion of the underlying cushion 30 has a more arcuate, e.g., semi-circular, question-mark, sickle-shape, configuration that defines a space 34 below a lower portion of the underlying cushion 30 and adjacent the base wall 28.

In the illustrated embodiment, the widest or most external cushion point is the external surface of the underlying cushion 30 and the base wall 28 and frame attachment 29 are offset internally with respect to this. Thus, by the design of the cushion 10 and in particular the underlying cushion curvature, the frame is attached at a narrower point and thus the frame itself is narrower. This arrangement has significant advantages in terms of the frame weight, perceived bulk, and size. This arrangement may also minimize the dead space within the mask which will help to reduce $CO_2$ rebreathing.

Moreover, the space 34 below the underlying cushion 30 allows a greater range of movement of the underlying cushion 30 to add more flexibility to the underlying cushion 30 and hence the membrane 32 in use. Specifically, the space 34 below the underlying cushion 30 enables more displacement of the underlying cushion 30 using substantially the same space restraints as the UltraMirage® cushion 700, for example. Additionally, the space 34 allows more displacement of the underlying cushion 30 before bottoming out, therefore reducing discomfort. Thus, this arrangement provides a more gradual force, improves comfort, and allows a wider range of patients to achieve seal.

Variable Spring Constant

As illustrated, the underlying cushion 30 has a spring-like connection with the base wall 28 such that the underlying cushion 30 can move with respect to the base wall 28. That is, the underlying cushion 30 is movable into the space 34 (the underlying cushion 30 is also movable into the space 33). Thus, a spring force is provided when a frame force is applied and the underlying cushion 30 is resiliently moved back into its initial position when the frame force is released. The underlying cushion 30 and/or base wall 28 may have any suitable spring constant, and the spring constant may be varied anywhere along its length, e.g., by tapering and/or varying the thickness of the base wall 28, varying the thickness of intermediate and/or lower portions of the underlying cushion 30. Also, the spring-like connection may extend along the whole underlying cushion 30 or the spring-like connection may be localized in certain regions such as the cheekbone region.

Thus, a spring characteristic is molded with the base wall 28 and underlying cushion 30 of the cushion 10 which allows a continuously variable spring constant to be incorporated into the base wall 28 and underlying cushion 30, e.g., the wall stiffness can be varied at each cushion region to suit the sealing requirements in each region which may vary due to the underlying facial structure of the patient.

Figure 22:
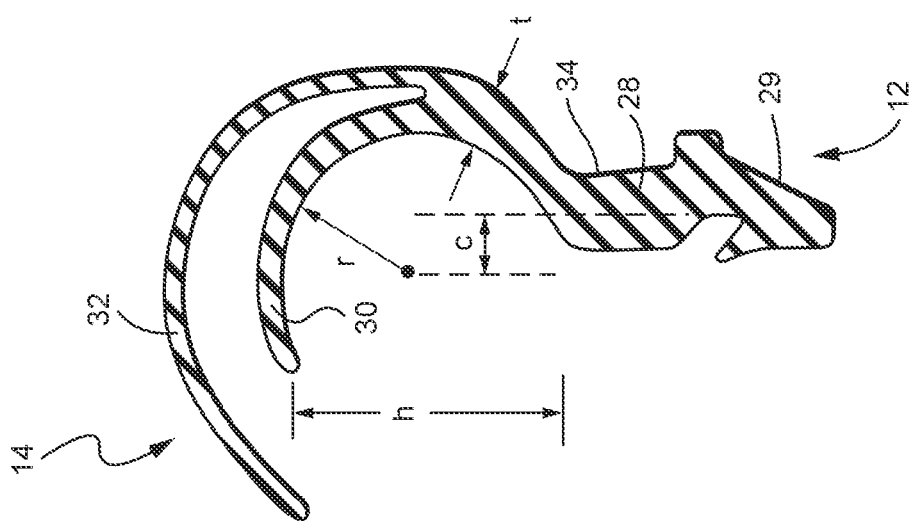
FIG. 22 is a cross-sectional view through the cushion shown in FIGS. 1-9 that illustrates parameters that can modify a spring characteristic of the underlying cushion.
Figure 25:
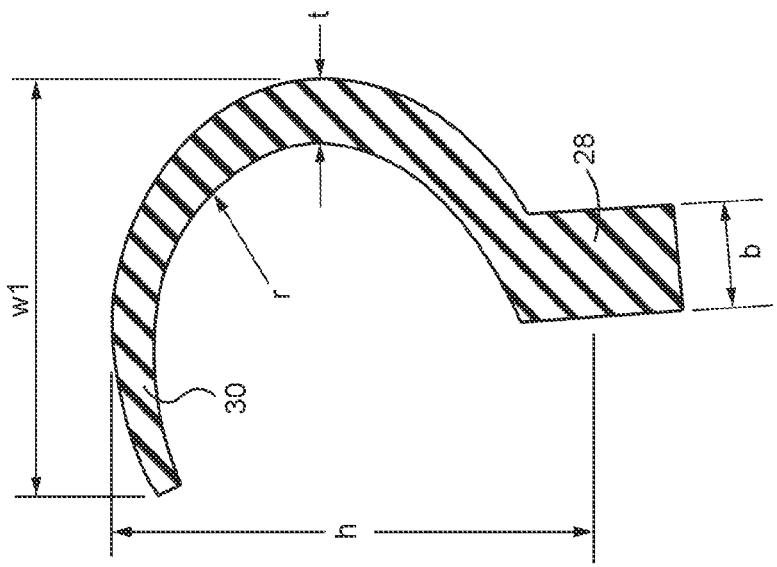

The spring characteristics of the base wall 28 and underlying cushion 30 may be modified by varying a number of characteristics shown in FIG. 22. For example, the spring characteristics may be modified by varying the underlying cushion height h, the thickness t, the radius r, and the underlying cushion offset c. It is to be understood that these parameters are merely exemplary, and other parameters may be varied to modify the spring characteristics of the base wall 28 and underlying cushion 30.

FIGS. 23-29 illustrate parameters of an embodiment of the underlying cushion 30 and base wall 28 to achieve desired spring characteristics. As illustrated, the underlying cushion 30 and base wall 28 is configured to provide a variable spring constant around the perimeter of the cushion 10. That is, the spring constant of the underlying cushion 30 and base wall 28 differs along the side of nose, upper cheek, and lower cheek regions 17, 18, 19. Although specific parameters of the cushion 10 are shown in FIGS. 23-29, it is to be understood that these parameters are merely exemplary and other parameters are possible depending on application.

In the nasal bridge region 16 (e.g., see FIG. 10), no underlying cushion 30 is provided in order to provide high flexibility and the ability to conform to a variety of facial shapes. However, in an embodiment, there may be an underlying cushion 30 with a very soft spring characteristic in this region.

In the side of nose regions 17 (see FIGS. 23-24), an underlying cushion 30 and base wall 28 with a fairly stiff spring characteristic is provided in order to provide lateral stability to squeeze the side of the patient's nose and keep the membrane 32 in contact with the underlying cushion 30. As illustrated, this arrangement is achieved by a relatively thick underlying cushion, short height, and tight radius. In an embodiment of the section shown in FIG. 23, h may be 12 mm, r may be 5 mm, t may be 2-3 mm, b may be 4 mm, w1 may be 11.5 mm, and w2 may be 8 mm. In an embodiment of the section shown in FIG. 24, h may be 14 mm, r may be 6-7 mm, t may be 2.5 mm, b may be 4 mm, w1 may be 11.5 mm, w2 may be 9.5 mm, and α may be 22°. It is to be understood that these dimensions and ranges are merely exemplary and other dimensions and ranges are possible depending on application.

Figure 24:
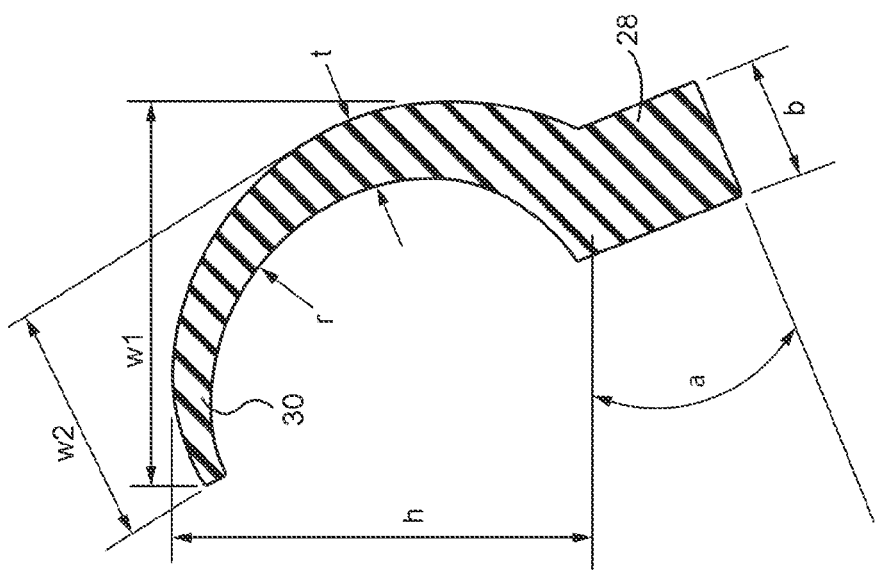
Figure 27:
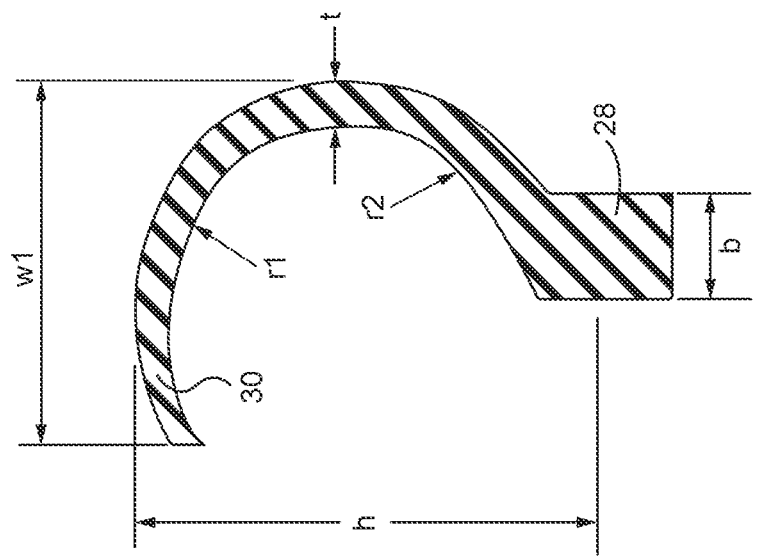
Figure 26:
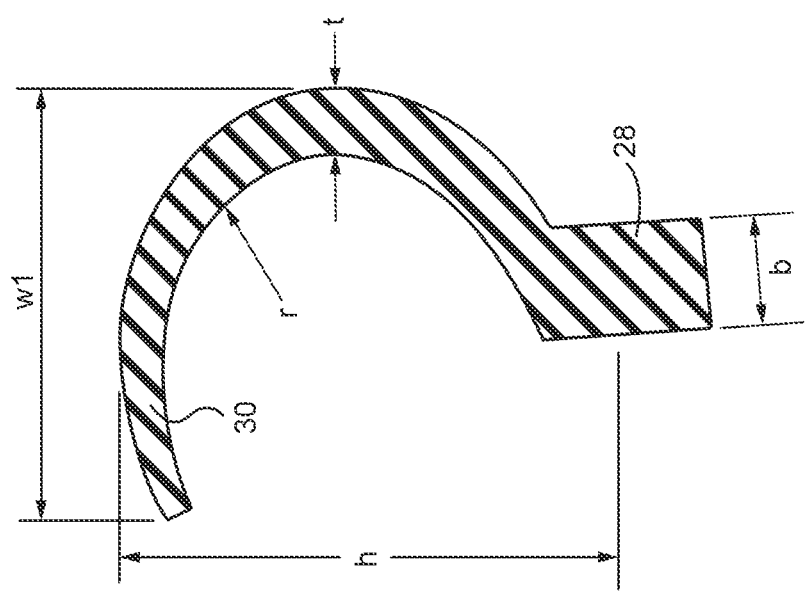
Figure 29:
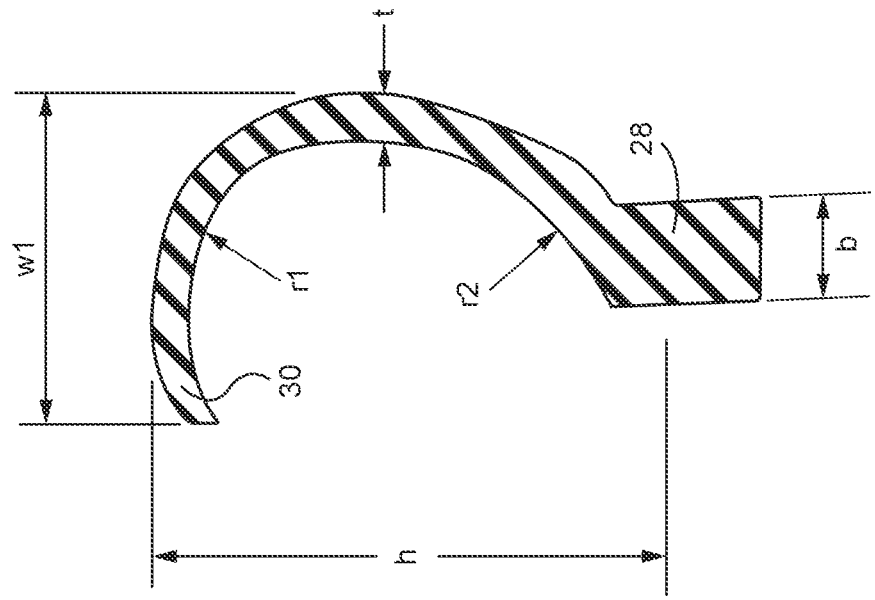
Figure 28:
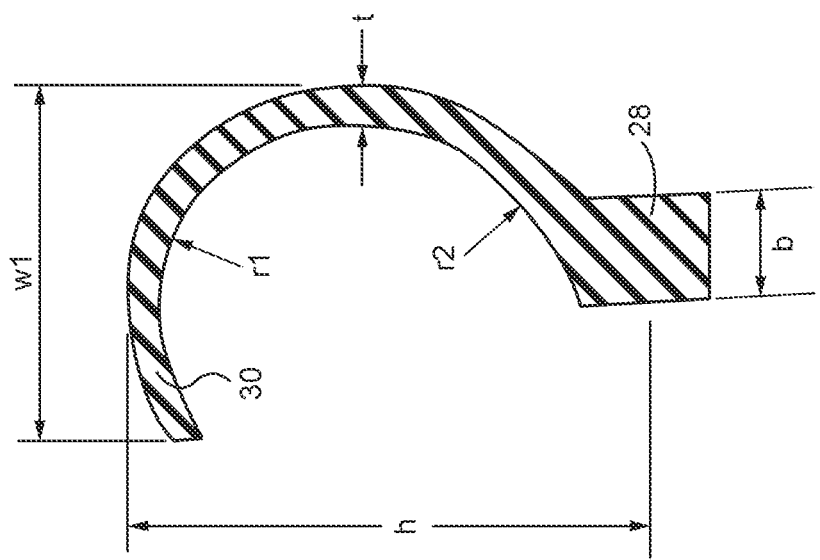

Also, as best shown in FIG. 24, the base wall 28 and underlying cushion 30 in the side of nose regions 17 have been rotated by about 22 degrees with respect to the bottom of the frame. That is, the base wall 28 and underlying cushion 30 are inclined or angled in the side of nose regions 17 of the cushion 10. This arrangement further increases the lateral stability and allows the force on the membrane to be applied perpendicular to the skin surface at the side of the patient's nose. This further helps to keep the membrane 32 in contact with the patient's skin and prevent any air leaks. In further embodiments, this angle may vary from 15 to 30 degrees.

In the upper cheek regions 18 (see FIGS. 25-26), the underlying cushion 30 and base wall 28 have a stiffness that is less than that provided in the side of nose regions 17 but stiffer than that provided in the lower cheek regions 19 due to the geometry of the underlying cushion, this is provided to suit the firmer bone structure of the upper cheeks. In an embodiment of the section shown in FIG. 25, h may be 12-15 mm, preferably 13.5 mm, r may be 5 mm, t may be 2 mm, b may be 3 mm, and w1 may be 11.5 mm. In an embodiment of the section shown in FIG. 26, h may be 12-15 mm, preferably 13.5 mm, r may be 5 mm, t may be 2 mm, b may be 3 mm, and w1 may be 11.5 mm. It is to be understood that these dimensions and ranges are merely exemplary and other dimensions and ranges are possible depending on application.

In the lower cheek regions 19 (see FIGS. 27-29), the underlying cushion 30 and base wall 28 has a relatively low spring constant. That is, the underlying cushion 30 in the lower cheek regions 19 is fairly soft since the fleshy cheek region of the patient deforms readily to form a seal with the cushion at relatively low forces. As illustrated, this arrangement is achieved by a greater height h, larger radii r, and a thinner underlying cushion wall. In an embodiment of the section shown in FIG. 27, h may be 14 mm, r1 may be 5 mm, r2 may be 7 mm, t may be 1.5-2 mm, b may be 3.5 mm, and w1 may be 11.5 mm. In an embodiment of the section shown in FIG. 28, h may be 16.5 mm, r1 may be 6-7 mm, r2 may be 8 mm, t may be 1.5 mm, b may be 3.5 mm, and w1 may be 11.5 mm. In an embodiment of the section shown in FIG. 29, h may be 17.5 mm, r1 may be 6-7 mm, r2 may be 9-10 mm, t may be 1.5 mm, b may be 3.5 mm, and w1 may be 11.5 mm. It is to be understood that these dimensions and ranges are merely exemplary and other dimensions and ranges are possible depending on application.

In the chin region 20 (see FIG. 14), no underlying cushion 30 is provided, although a very flexible spring region may be used. The chin region 20 provides an unconstrained membrane region that allows for lateral movement, mouth opening or movement, and a range of facial shapes.

Thus, the cushion 10 may be configured to provide different vertical and/or lateral stiffness in different regions of the cushion. For example, the side of nose regions 16, 17 are laterally stiffer than the other regions in order to provide more lateral stability at the patient's nose.

Alternative Embodiments of Base Wall and Underlying Cushion

Figure 30J:
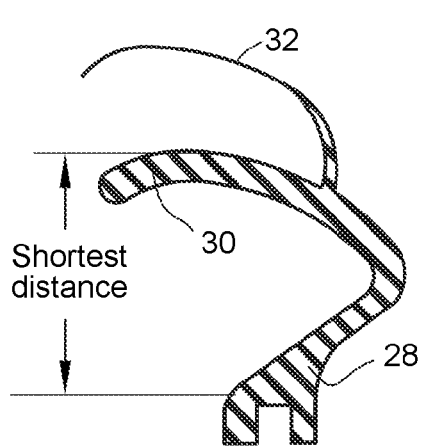
FIGS. 30A-30N are cross-sectional views illustrating alternative embodiments of a cushion according to the present invention.
Figure 30K:
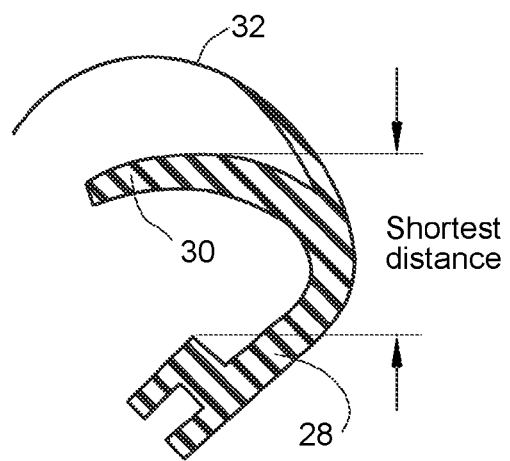
Figure 30N:
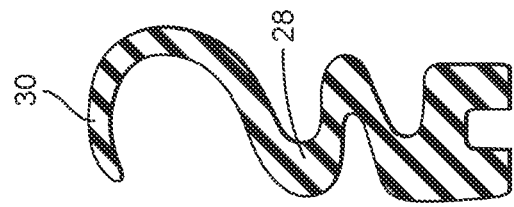
Figure 30M:
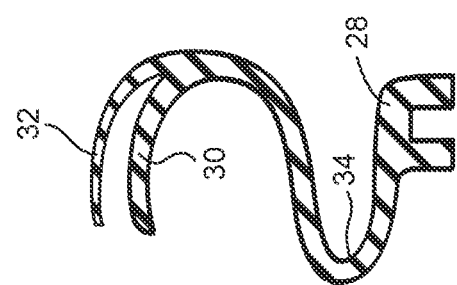
Figure 30L:
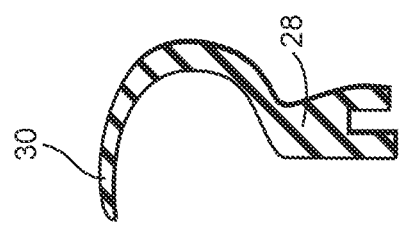

FIGS. 30A-30N illustrate alternative embodiments of the base wall 28 and the underlying cushion 30. Each of these embodiments provides an arrangement that allows flexibility of the underlying cushion 30 in use. In FIG. 30A, the underlying cushion 30 defines an enclosed space 60 that may optionally be filled with pressurized air, foam, gel, or elastomeric material and adapted to dampen movement of the underlying cushion 30 in use. In FIG. 30B, the space 34 below the underlying cushion 30 is within the interior of the breathing cavity. Also, the underlying cushion 30 has an arcuate shape that curves away from the interior of the breathing cavity towards the base wall 28. However, the underlying cushion 30 may have any other suitable shape. For example, the underlying cushion 30 in FIG. 30C has a bulbous shape, which may be solid or hollow. In FIG. 30D, the underlying cushion 30 has a general Z-shape. In FIGS. 30E and 30F, the underlying cushion 30 has a bulbous shape (which may be solid or hollow), and the space 34 below the underlying cushion 30 has a ramped configuration. In FIGS. 30C, 30E, and 30F, the bulbous shape may optionally be filled with pressurized air, foam gel, or elastomeric material and adapted to dampen movement of the underlying cushion 30 in use. In FIG. 30E the ramped configuration of the space 34 is adapted to direct the underlying cushion 30 downwardly into the base wall 28 in use, and in FIG. 30F the ramped configuration of the space 34 is adapted to direct the underlying cushion 30 inwardly towards the breathing cavity in use. In FIGS. 30G, 30H, and 30I, the underlying cushion 30 has a general T-shape. Also, in FIGS. 30H and 30I, the base wall 28 defines an enclosed space 62 below the T-shaped underlying cushion 30. The enclosed space 62 may be optionally filled with pressurized air, foam, gel, or elastomeric material and adapted to dampen movement of the underlying cushion 30 in use. Moreover, the spring constant may be varied by varying the pressure within the enclosed space 62. Additionally, the lower surface of the space 62 may have a ramped configuration (as shown in FIG. 30H) adapted to direct the underlying cushion 30 inwardly towards the breathing cavity in use. The lower surface of the enclosed space 60 in FIG. 30A may also have a ramped configuration for directing the underlying cushion 30 in use. In FIGS. 30J and 30K, the underlying cushion 30 has an elongated section length for soft spring characteristics. FIG. 30L illustrates a single wall construction with an underlying cushion 30 and no membrane. In FIG. 30M, the space 34 below the underlying cushion 30 is greatly increased. In FIG. 30N, a spring construction is provided below the base wall 28.

Displacement Provided by Underlying Cushion

Figure 31:
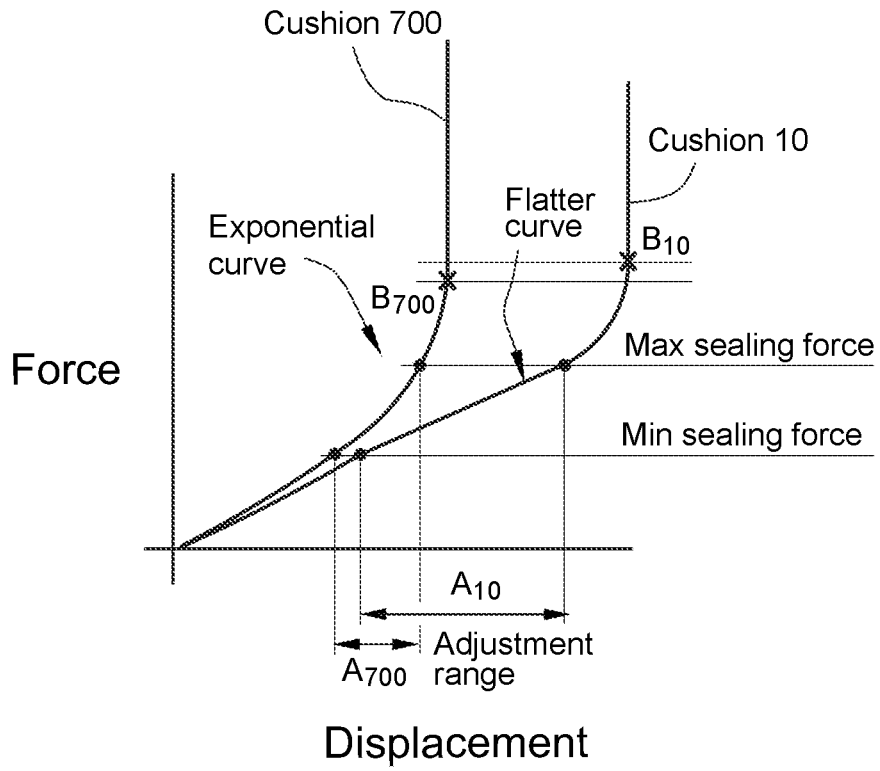
FIG. 31-32 are graphs illustrating the general relationship between Force and Displacement for embodiments of the cushion shown in FIGS. 1-9 and a known cushion commercially sold under the name of UltraMirage® Full Face by ResMed Ltd.

The space 34 allows more displacement of the underlying cushion 30 for a predetermined amount of force when compared to the UltraMirage® cushion 700. That is, the underlying cushion 30 provides more movement for a given force. For example, FIG. 31 illustrates the general relationship between Force and Displacement for the cushion 10 and the UltraMirage® cushion 700. As illustrated, the curve for the cushion 10 is flatter than the exponential-type curve of the UltraMirage® cushion 700. Thus, the underlying cushion 30 is less stiff and more compliant when compared to the UltraMirage® cushion 700. It is noted that the space 34 could be filled with a gel, silicone or other structure to vary the spring characteristic that it provides.

Further, as illustrated in FIG. 31, the point $B_{10}$ at which the cushion 10 is fully compressed or bottomed-out is at a greater displacement than the point $B_{700}$ at which the UltraMirage® cushion 700 is bottomed-out. Moreover, the bottom-out point $B_{10}$ occurs at a greater force than the bottom-out point $B_{700}$. Thus, the cushion 10 increases the force required to bottom-out, and provides a wider range of adjustment. Additionally, FIG. 31 illustrates an example of maximum and minimum comfortable sealing forces, which provides an example force range necessary to achieve seal. As illustrated, the range of displacement $A_{10}$ within this force range for the cushion 10 is substantially larger than the range of displacement $A_{700}$ within this force range for the UltraMirage® cushion 700. Thus, the cushion 10 allows a wide range of adjustment or displacement to achieve seal, and ensures that the sealing force is substantially less than the bottom-out force so that the cushion does not have to bottom-out to seal.

Figure 32:
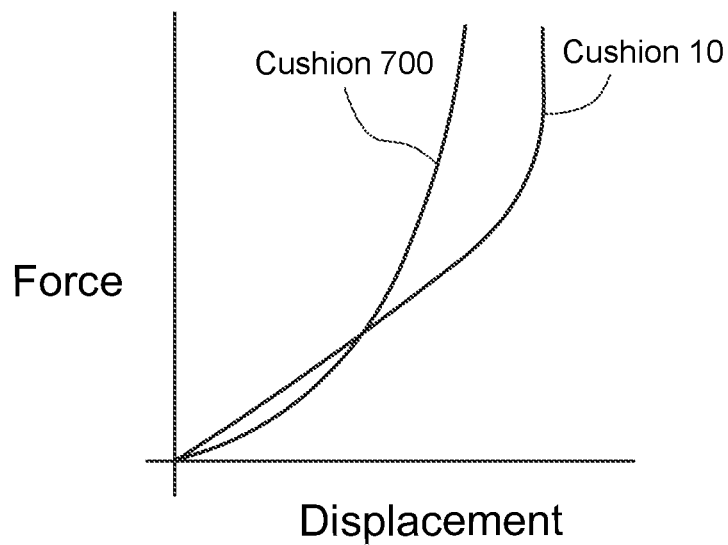

FIG. 32 illustrates another embodiment of the relationship between Force and Displacement for the cushion 10 and the UltraMirage® cushion 700. In this embodiment, the linear portion of the curve for cushion 10 has a greater slope than the linear portion of the curve for cushion 10 in FIG. 31. The difference in slope may be attributed to a difference in spring constants of respective underlying cushions 30. Thus, the cushion represented in FIG. 31 provides more displacement for a given force than the cushion represented in FIG. 32. Also, the curve for the cushion 10 in FIG. 32 intersects with the curve for the UltraMirage® cushion 700, such that the force of cushion 10 is higher at lower displacement, to ensure a seal, and lower at higher displacement, to maintain comfort for a longer range of displacement.

Figure 33:
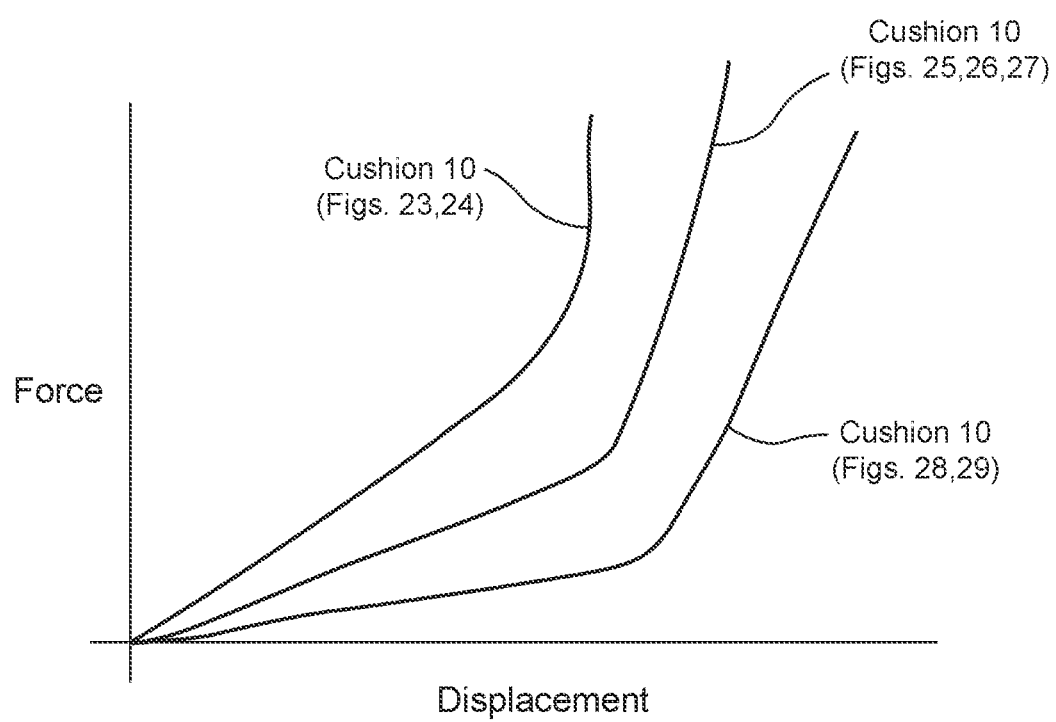
FIG. 33 is a graph illustrating the general relationship between Force and Displacement for various cross-sections of the cushion shown in FIGS. 23-29.

FIG. 33 illustrates another embodiment of the relationship between Force and Displacement for the cushion 10. In this embodiment, typical curves for the different regions of the cushion 10 are shown. Specifically, one curve represents the cross-sections of FIGS. 23-24 in the side of nose region 17, another curve represents the cross-sections of FIGS. 25-27 in upper cheek and lower cheek regions 18, 19, and yet another curve represents the cross-sections of FIGS. 28-29 in the lower cheek region 19. As illustrated, the cushion 10 is softer or less stiff in the lower regions of the cushion 10.

Extended Spring Length of Underlying Cushion

Figure 34A:
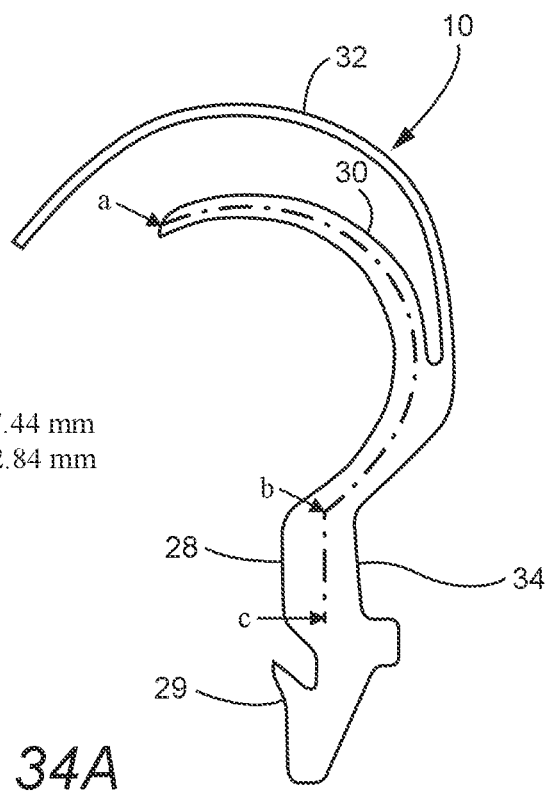
FIG. 34A illustrates a spring length for the cushion shown in FIGS. 1-9, and showing exemplary dimensions of an embodiment according to the present invention.
Figure 34B:
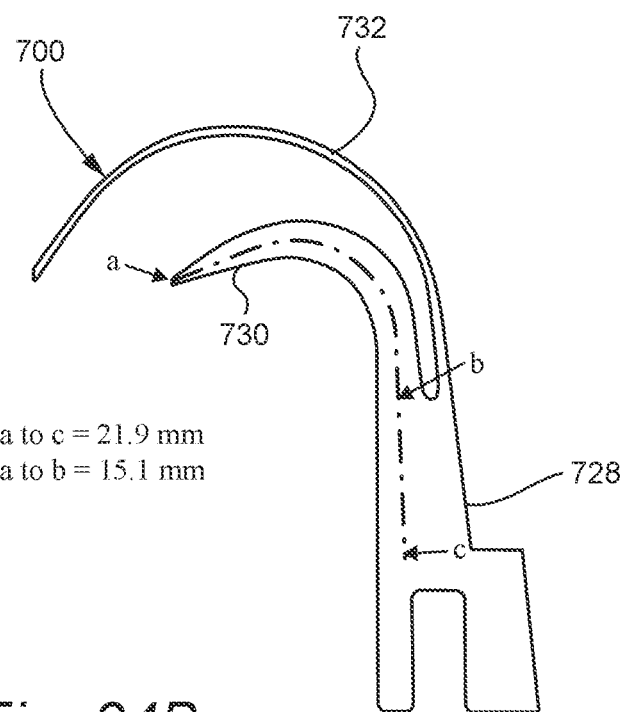
FIG. 34B illustrates a spring length for a known cushion commercially sold under the name of UltraMirage® Full Face by ResMed Ltd., and showing exemplary dimensions of the UltraMirage® Full Face.

FIGS. 34A and 34B illustrate the extended length of the flexible underlying cushion 30 which is used to provide a softer spring characteristic in selected regions of the cushion 10 when compared with a typical prior art cushion, e.g., the UltraMirage® cushion 700. The length a to b can deform, thus providing a spring characteristic. As illustrated, the length a to b of the cushion 10 (FIG. 34A) is considerably longer when compared to the UltraMirage® cushion 700 (FIG. 34B) due to the curvature of the underlying cushion 30. In the illustrated embodiment, the length a to b of the cushion 10 is 22.84. However, in an embodiment, the length a to b of the cushion 10 may be in the range of 16-30, preferably 20-25, most preferably 22-24. In another embodiment, the length a to b of the cushion 10 may be in the range of 16-20. The length b to c is fairly rigid and does not deform to provide a spring characteristic. The added length in the cushion 10 has been achieved by the arcuate shape of the underlying cushion 30 and the space 34 is a result of this shape. This added length adds flexibility and a greater range of movement to the cushion 10. FIGS. 30J and 30K illustrate other embodiments for achieving a longer section length.

Configuration of Membrane in Nasal Bridge Region

The membrane 32 is structured to form an effective seal around nasal bridge, side of nose, upper cheek, lower cheek, and chin regions 16, 17, 18, 19, 20 of a patient. Another aspect of the invention relates to the configuration of the membrane 32 in the nasal bridge region 16 of the cushion 10, which has been structured to improve sealing and comfort in this region.

Figure 36:
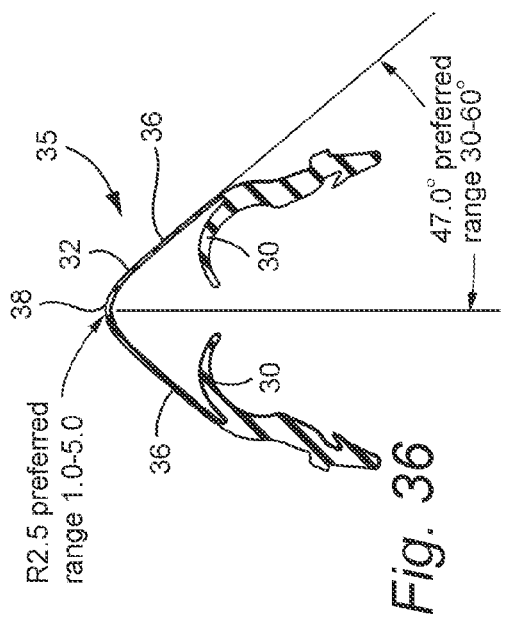
FIGS. 36-37 are cross-sectional views through the cushion shown in FIG. 35.
Figure 68:
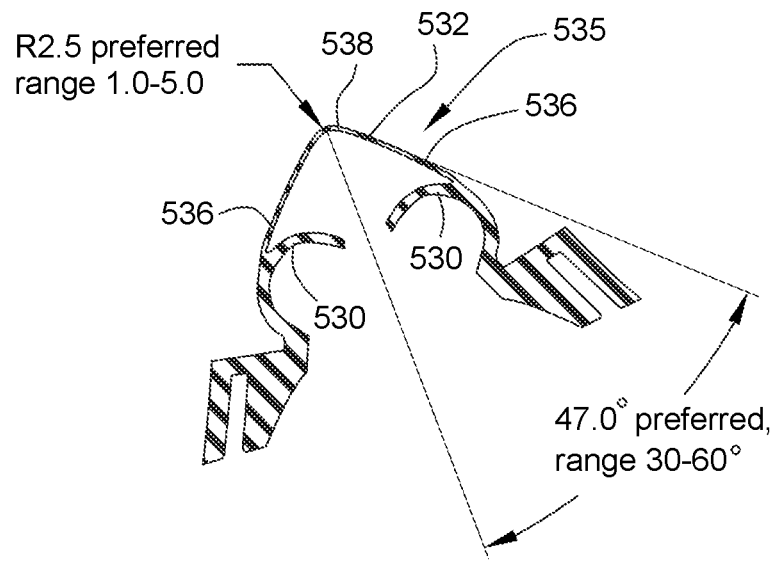

Specifically, as shown in a preferred embodiment in FIG. 36 and in an alternative embodiment in FIG. 68, the membrane 32 forms an elongated ridge 35 in the nasal bridge region 16 wherein sloping sides 36 meet to form an elongated crest 38. Each of the sloping sides 36 is angled from the crest centerline in the range of 30-60°, preferably about 47°. The crest 38 has a radius of curvature in the range of 1.0-5.0 mm, preferably about 2.5 mm. As illustrated, the underlying cushion 30 has been eliminated from beneath the membrane 32 in the nasal bridge region 16, which allows the membrane 32 in this region to freely move between the underlying cushions 30 provided in the side of nose regions 17. As discussed in greater detail below, this membrane configuration allows the creation of a steeply inverted section upon engagement with the patient's nose, which improves fit, comfort, and seal in the nasal bridge region 16. In contrast, the UltraMirage® cushion 700 is relatively flat in this region (see FIG. 52).

Figure 37:
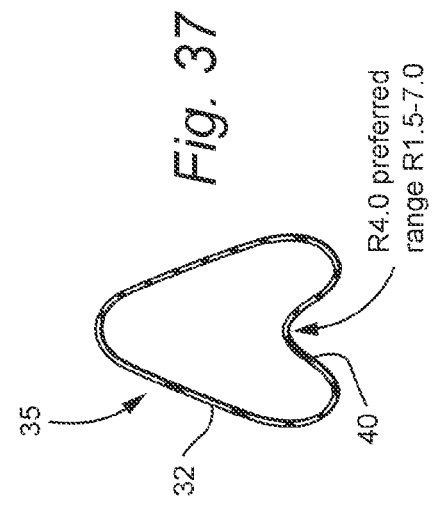
Figure 69:
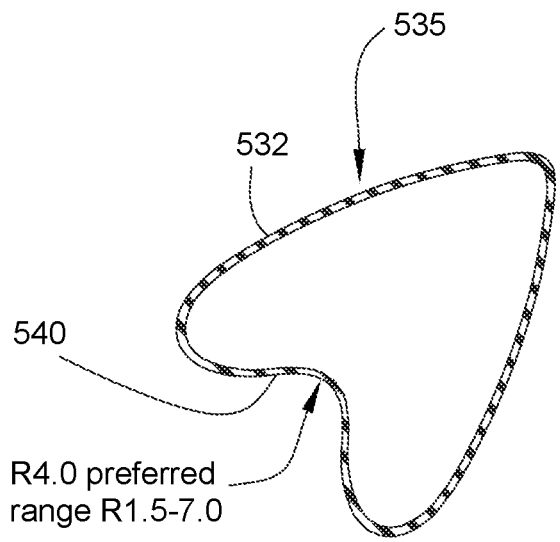

As shown in a preferred embodiment in FIG. 37 and in an alternative embodiment in FIG. 69, the forward end 40 of the elongated ridge 35 has an arcuate configuration. The forward end 40 is structured to engage the patient's nasal bridge region and has a radius of curvature in the range of 1.5-7.0 mm, preferably about 4.0 mm.

Sharp Cross-Sectional Profile of Nasal Bridge Region

As shown in FIG. 10, the membrane 32 in the nasal bridge region 16 has a sharper cross-sectional profile than the corresponding portion of the UltraMirage® cushion 700 (see FIG. 48). Specifically, the membrane 32 provides a large contoured portion that curves inwardly towards the cavity of the cushion along a radius to terminate at an inner edge of the membrane 32. This arrangement more closely follows the contour or curvature of the patient's nasal bridge region. In the illustrated embodiment, the membrane 32 is angled with respect to a face contacting plane of the cushion, e.g., in the range of 30-50°. In contrast, the corresponding angle of the UltraMirage® cushion 700 is about 6°. This arrangement provides more comfort and a better fit for the patient.

Flat Portion in Nasal Bridge Region

Figure 38:
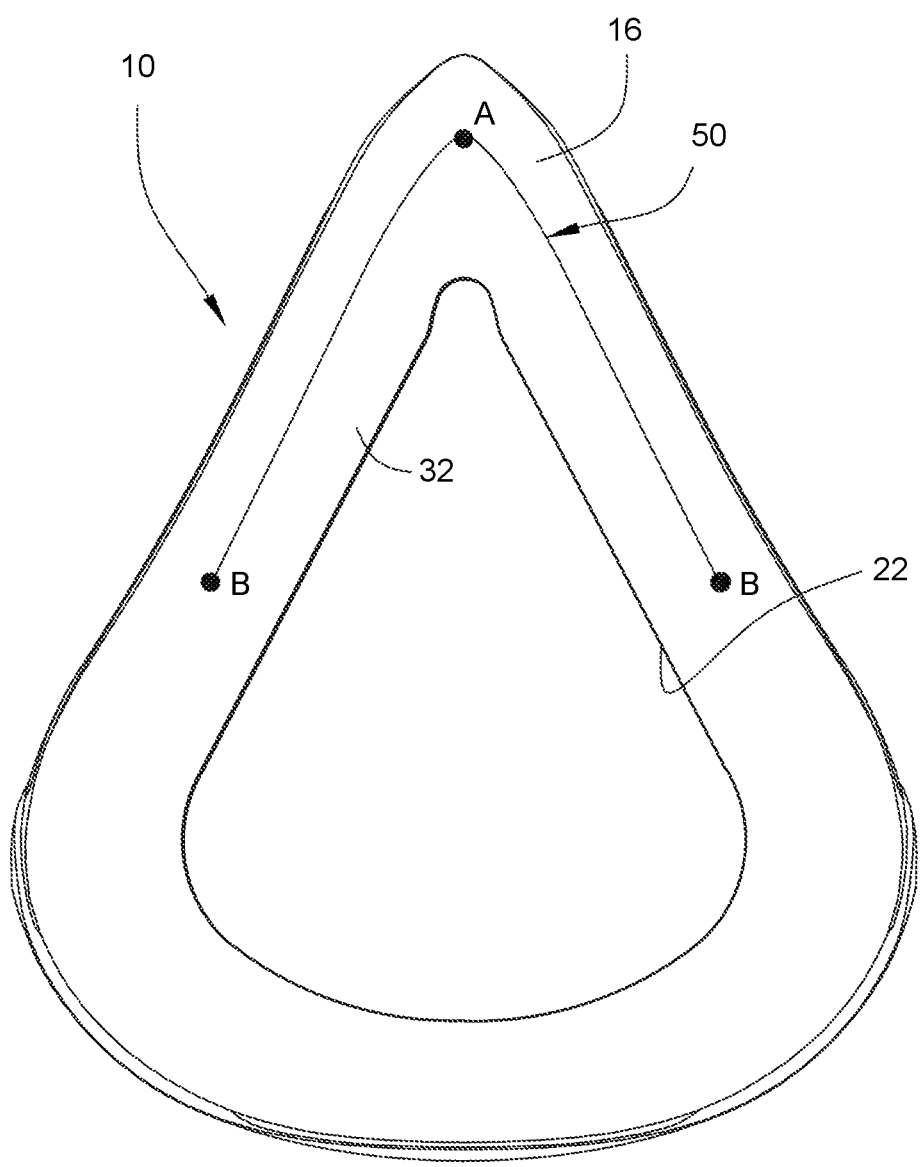
FIG. 38 is a front view of the cushion shown in FIGS. 1-9 illustrating a flat portion thereof.

As best shown in FIG. 38, the nasal bridge region 16 has a substantially flat portion 50, e.g., on the apex of the membrane curvature, in elevation view that may deform to provide a more comfortable fit for a wide range of patients, e.g., from flatter nasal bridges to sharper nasal bridges.

Specifically, one aspect of the invention is to provide a membrane 32 in the nasal bridge region 16 that will accommodate "flat faces", e.g., those patient's with a low nasal bridge. In order to achieve this, the cushion 10 has an upper point A which is higher than or level with points B (see FIG. 38). This height in the nasal bridge region 16 is combined with a rolled edge that keeps the surface area of the membrane 36 substantially flat against the patient's nasal bridge. Keeping the surface area of the membrane 36 substantially flat against the patient's nasal bridge prevents leaks at the edge of the membrane.

The rolled edge also allows movement to accommodate higher nasal bridges. This arrangement is achieved without "stretching" the membrane which can lead to discomfort and patient sores. For example, the displacement of the cushion 10 at the nasal bridge region 16 may be greater than about 40 mm, e.g., 41 mm. In contrast, the UltraMirage® cushion 700 provides displacement of about 20 mm in the nasal bridge region. At these displacements, the membrane becomes quite taut, i.e., the point on the force vs. displacement graph where the force begins to rise sharply for a small displacement (see FIG. 38B).

The displacement values of the cushion in the nasal bridge region for some prior art cushions are as follows:
 ResMed™ Activa® Nasal Cushion—16 mm
 Respironics Comfort Full Face Cushion—26 mm
 ResMed Bubble Nasal Mask Cushion—43 mm
 Healthdyne Soft Series Nasal Mask Cushion—17 mm The above displacement values are by no means an accurate representation of what nose depth the cushion will cover. Rather, these displacement values are only an indication of the flexibility and/or range of the membrane. Thus, the cushion 10 provides an arrangement that is much more flexible and/or rangy than the UltraMirage® cushion 700, for example.

Figure 38B:
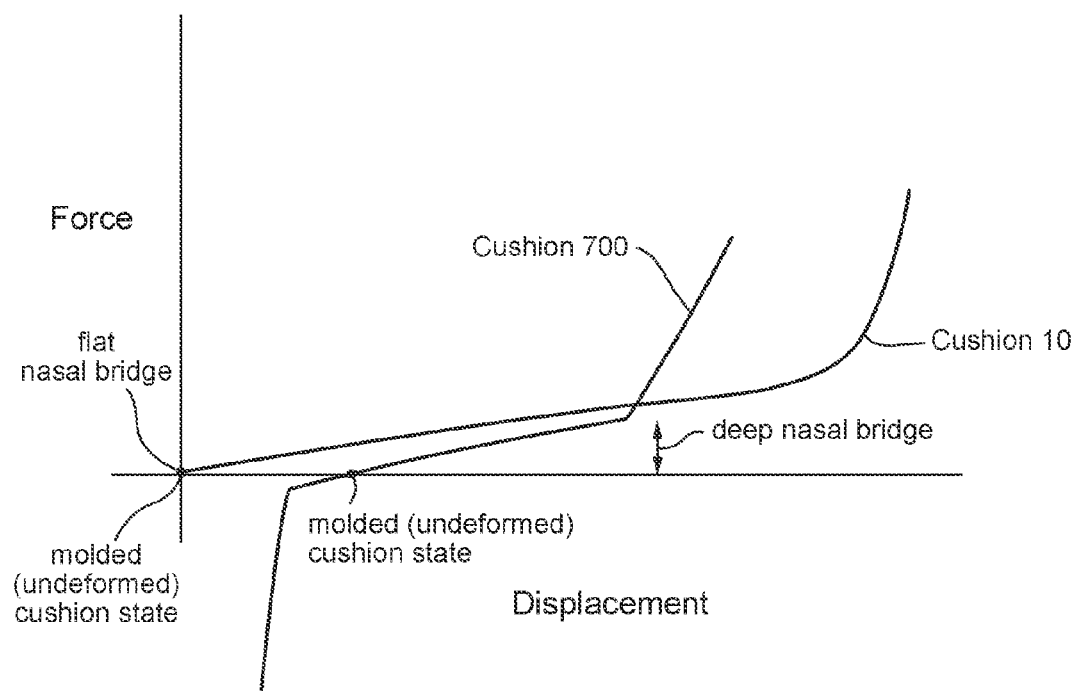
FIG. 38B is a graph illustrating the general relationship between Force and Displacement in a nasal bridge region for embodiments of the cushion shown in FIGS. 1-9 and a known cushion commercially sold under the name of UltraMirage® Full Face mask by ResMed Ltd.

The force vs. displacement graph of membrane 32 in the nasal bridge region 16 has a large displacement for relatively low forces. For example, as shown in FIG. 38B, the displacement provided by the cushion 10 in the nasal bridge region 16 is larger than that provided by the UltraMirage® cushion 700. This allows the cushion 10 to accommodate relatively deep nasal bridges in use. Also, the molded (undeformed) cushion state of the UltraMirage® cushion 700 (i.e., no force applied) does not comfortably accommodate a relatively flat or shallow nasal bridge. In an embodiment, the membrane of the cushion 700 blows out to meet patient's faces with shallow nasal bridges. Thus, the cushion 10 also accommodates a wider range of nasal bridge shapes than the UltraMirage® cushion 700.

Figure 35:
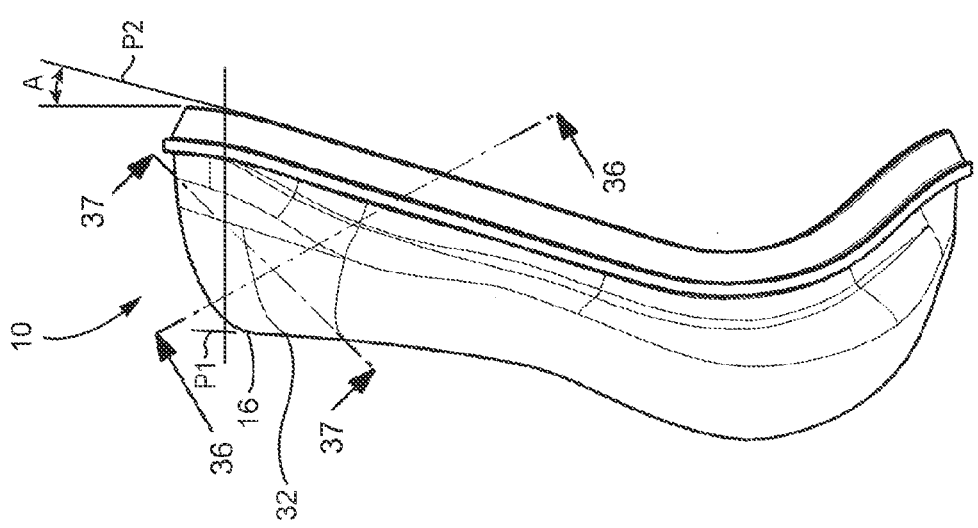
FIG. 35 is a side view of the cushion shown in FIGS. 1-9.
Figure 52:
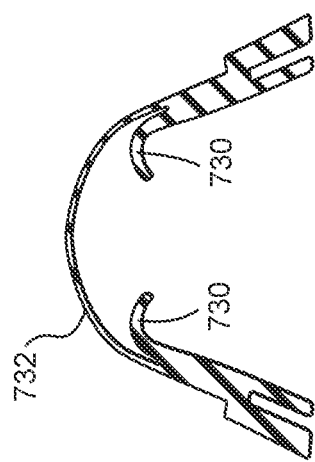
Figure 51:
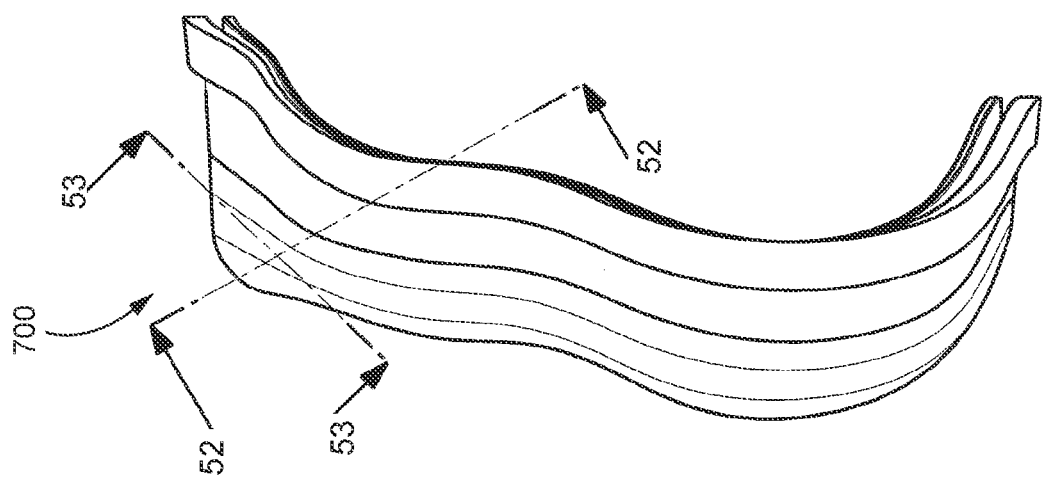
Figure 54:
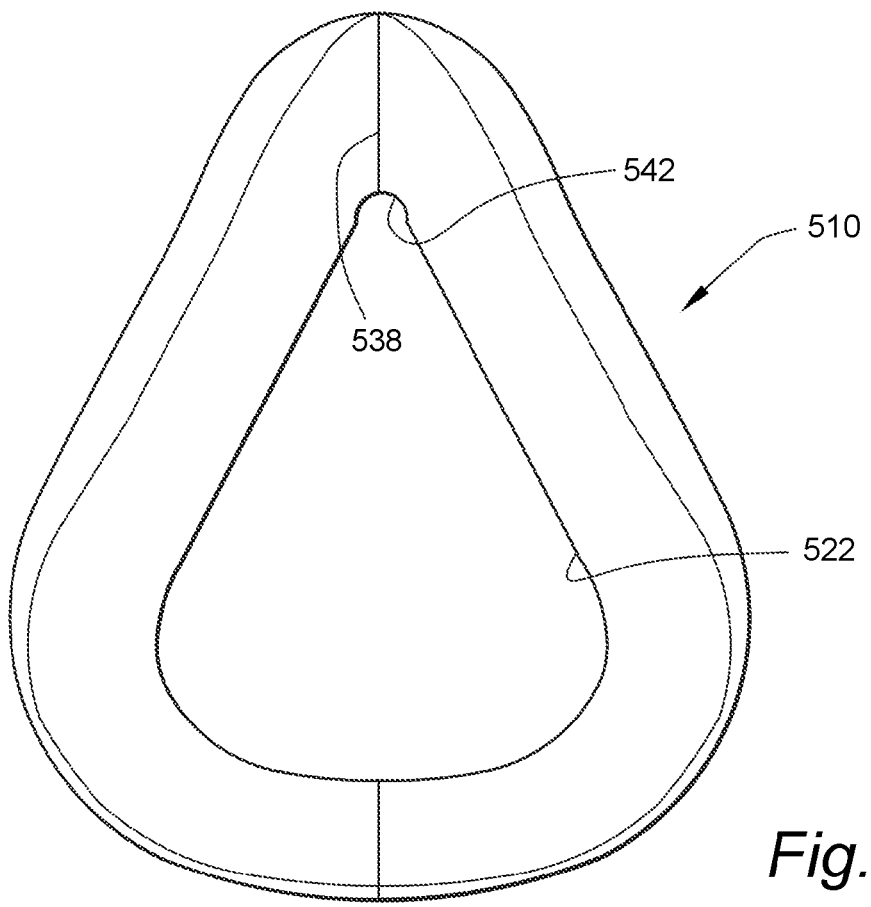
FIGS. 54-58 illustrate a cushion for a patient interface according to another embodiment of the present invention and showing exemplary dimensions of an embodiment.
Figure 55:
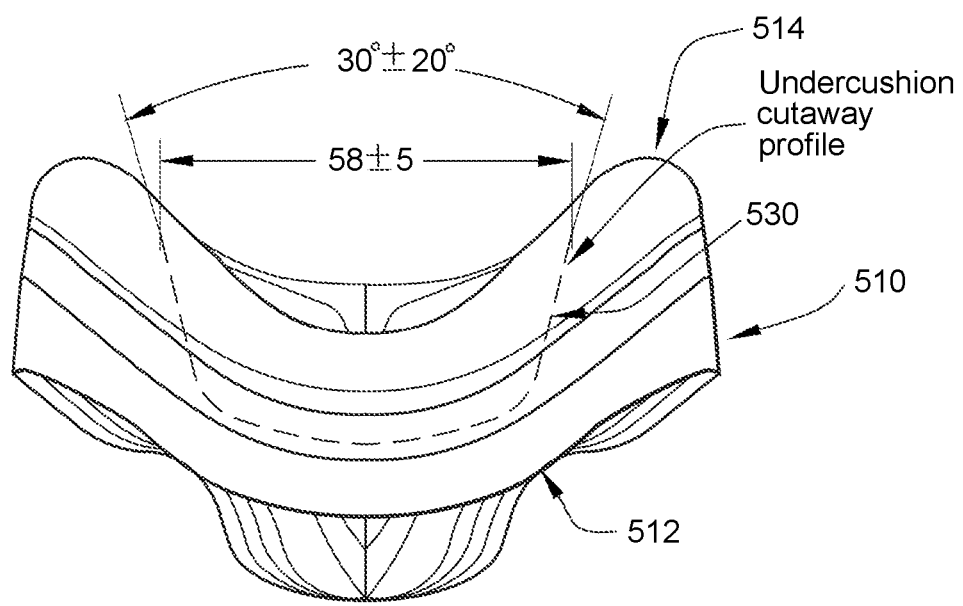
Figure 56:
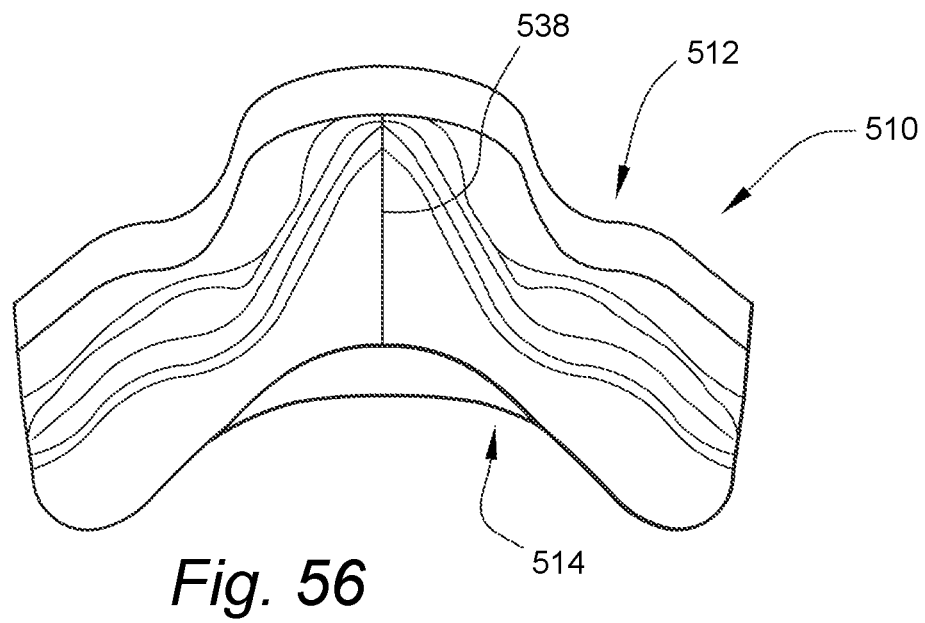
Figure 57:
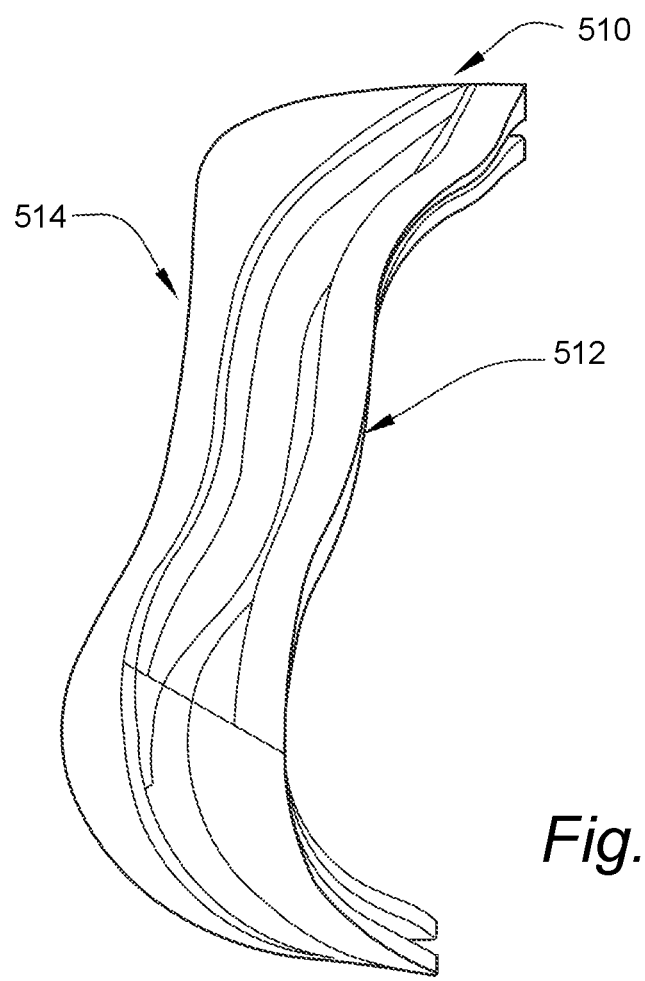
Figure 58:
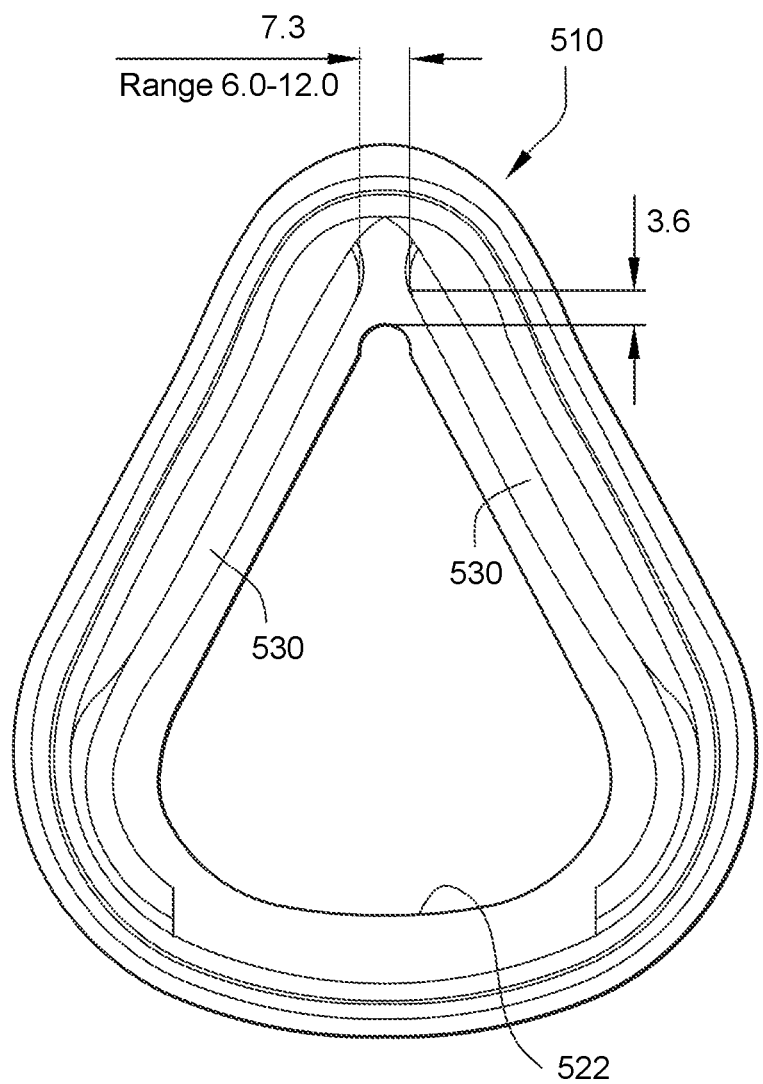
Figure 59:
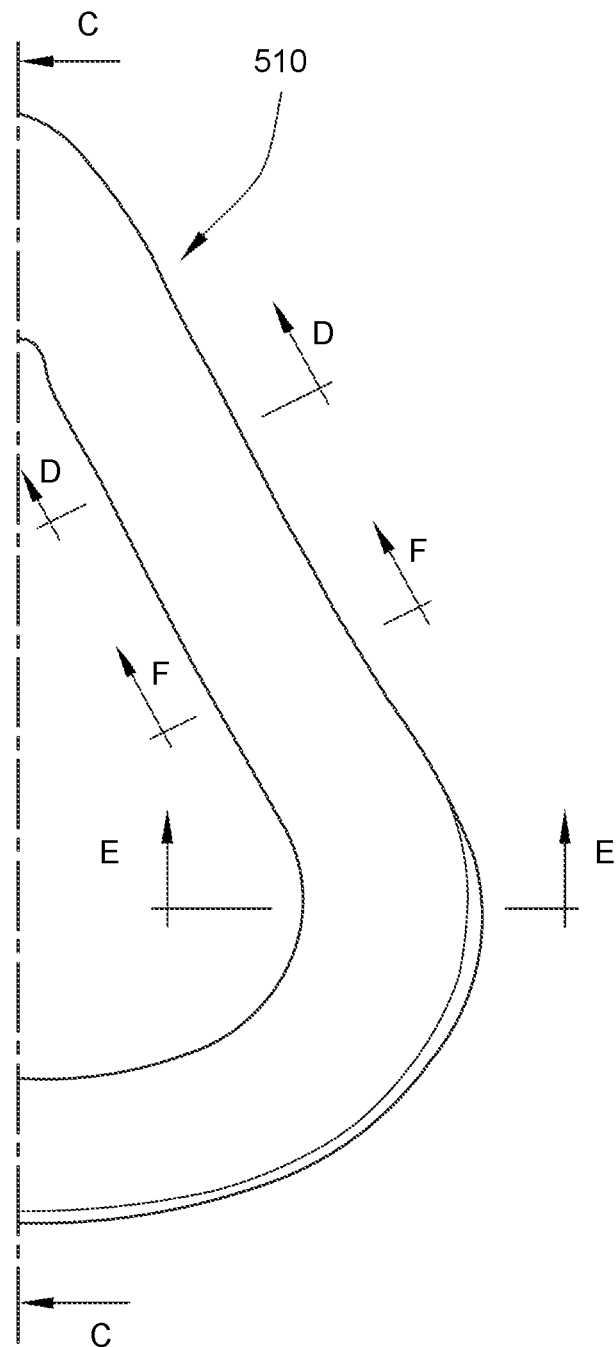

Further, as shown in FIG. 36, the profile of the membrane is more sharply peaked as compared to a flat profile or a saddle shape (e.g., compare with UltraMirage® cushion 700 in FIG. 52). Also, as shown in FIG. 35, flat portion in the nasal bridge region 16 extends along a relatively flat plane P1, and this plane P1 is angled at an angle A with respect to the plane P2 that defines the frame connection.

Thus, the shape (e.g., peak), the rolled edge, and the height, in the nasal bridge region 16 provide large displacement at relatively low forces. This arrangement accommodates a wider range of patients, e.g., from those with a low nasal bridge to those with a high nasal bridge, while maintaining a seal against the patient's face with little force on the membrane.

Figures 94A, 94B:
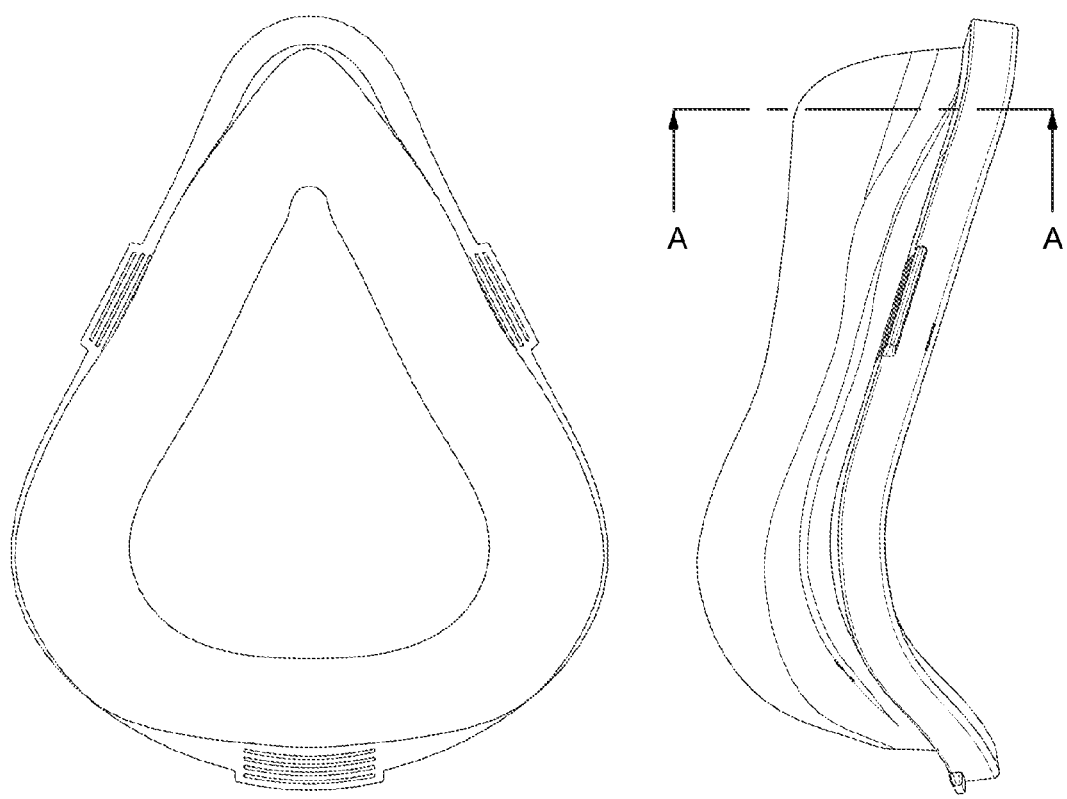
FIGS. 94A-94C are a set of views depicting a horizontal cross-section through the nasal bridge region of the cushion of FIG. 35.
Figure 94C:
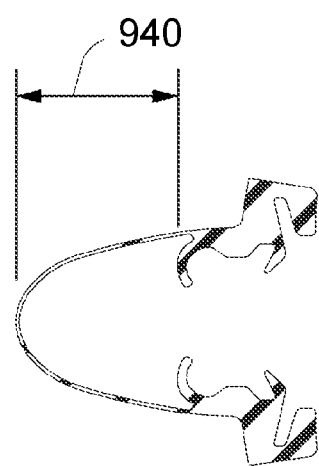
Figure 95A:
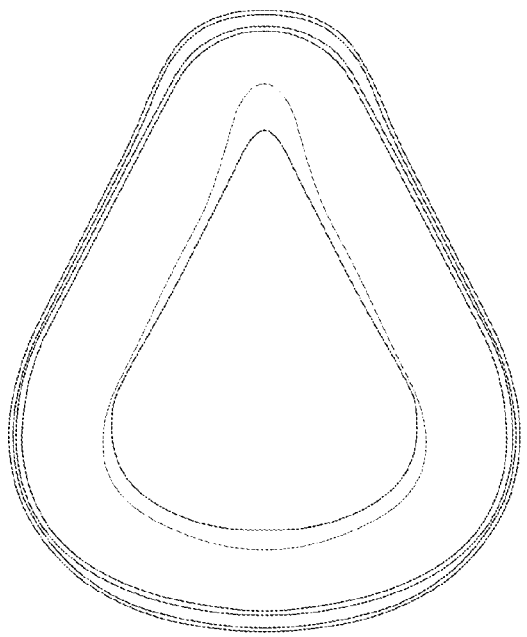
FIGS. 95A-95C are a set of views depicting a horizontal cross-section through the nasal bridge region of the prior art cushion of FIG. 51.
Figure 95B:
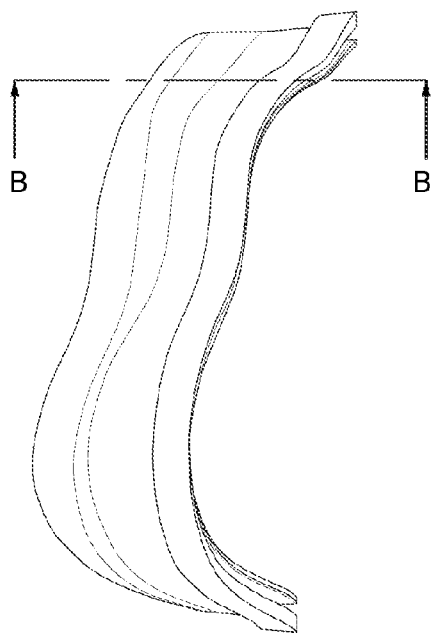
Figure 95C:
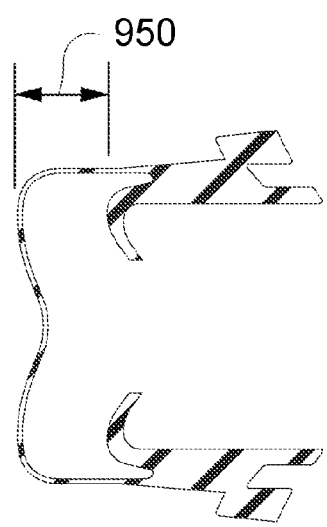

It is noted that the cushion height may vary around the cushion perimeter to vary flexibility or cushion displacement in different regions of the cushion. A reference dimension 940 for measurement of the cushion height (which may also be referred to as the membrane height)—i.e. the height between the apex of the membrane to where it meets the underlying cushion—is shown in FIG. 94C. A reference dimension 950 for measurement of the cushion height of the prior art cushion is shown in FIG. 95C.

Aperture in Membrane

As shown in FIGS. 39-40B, the inner edge of the membrane 32 defines the aperture 22 that receives the patient's nose and mouth. As illustrated, the aperture 22 has a generally triangular shape. Also, the apex of the aperture 22 has a rounded notch 42, e.g., keyhole. The notch 42 improves the seal with nasal bridge regions of various sizes and shapes, particularly patients with sharp noses. The notch 42 has a radius of curvature in the range of 1.5-6.0 mm, preferably about 3.0 mm. This rounded keyhole shape has a length, e.g., the keyhole shape extends outwards from an interior portion of the cushion, of at least 3.0 mm, as shown in FIG. 40A.

Rolling Action of Nasal Bridge Region of Cushion in Use

Figure 41:
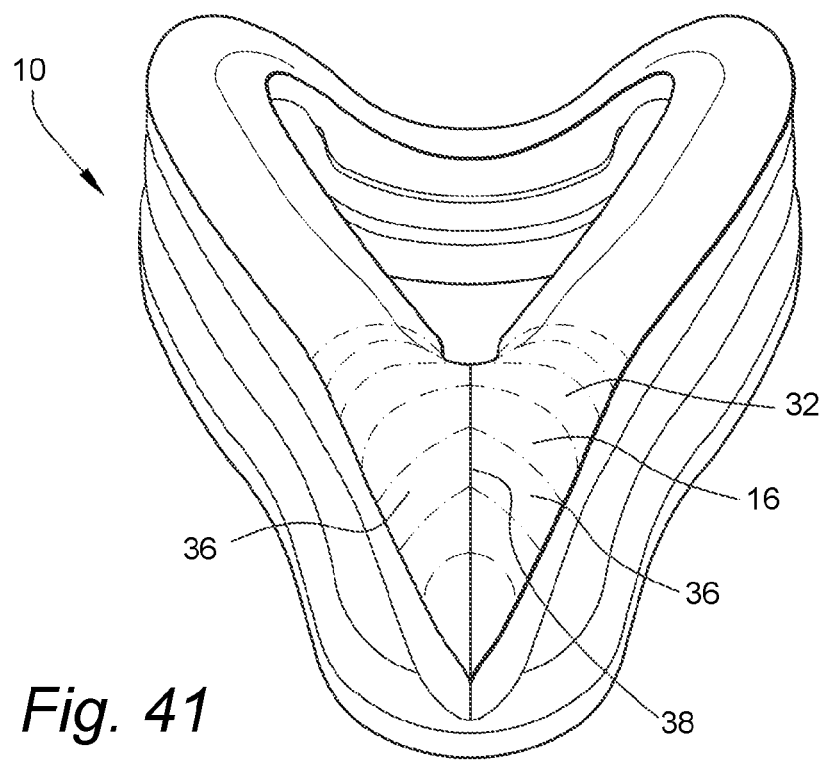
FIGS. 41-45 are perspective views of an embodiment of the cushion shown in FIGS. 1-9 illustrating the rolling action of the nasal bridge region in use.
Figure 42:
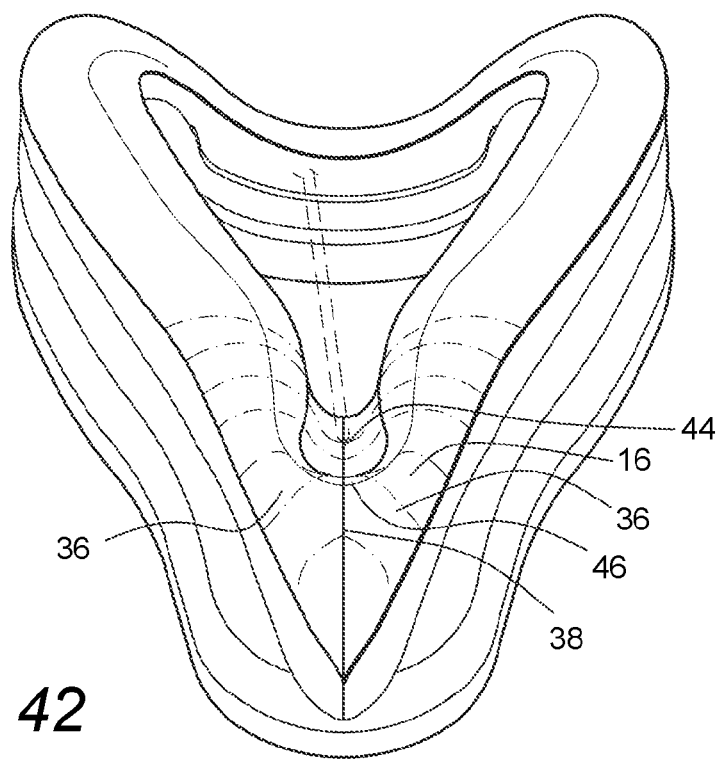
Figure 43:
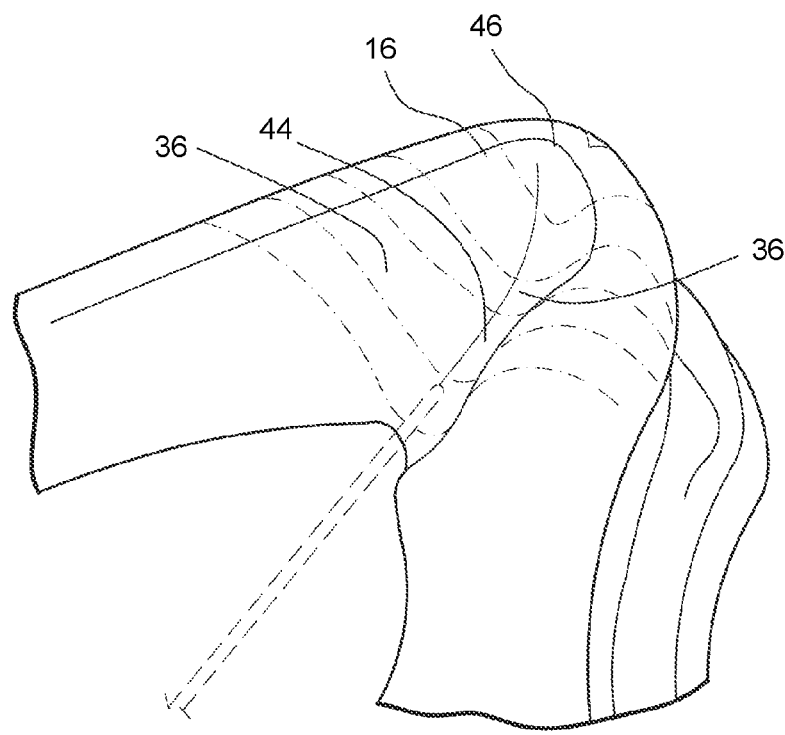
Figure 44:
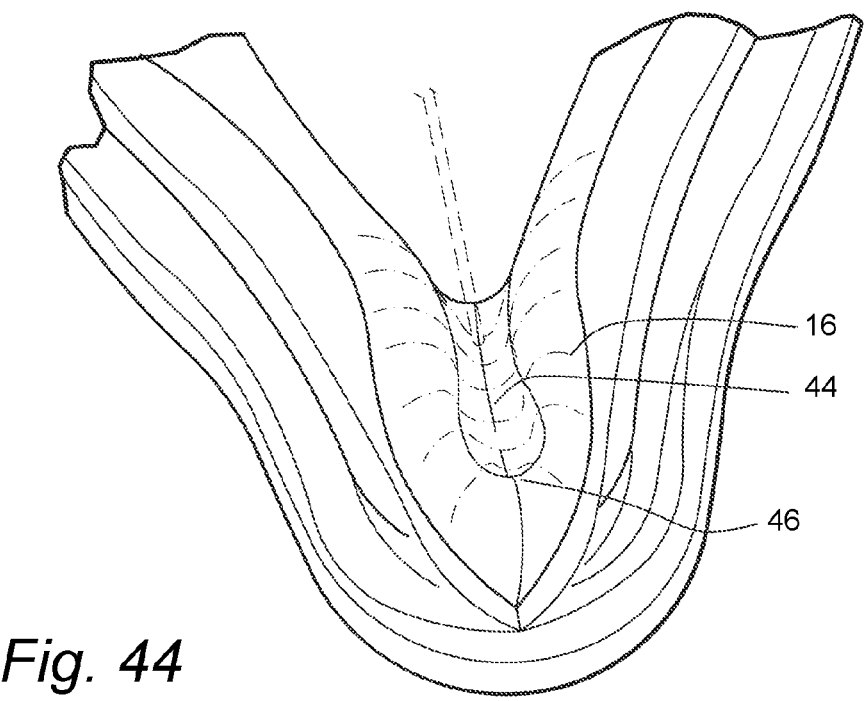
Figure 45:
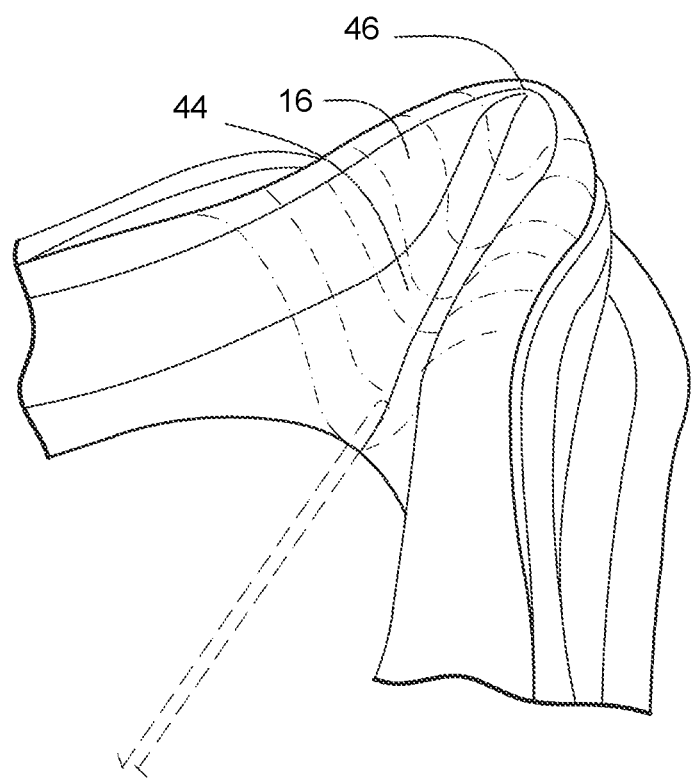
Figure 47:
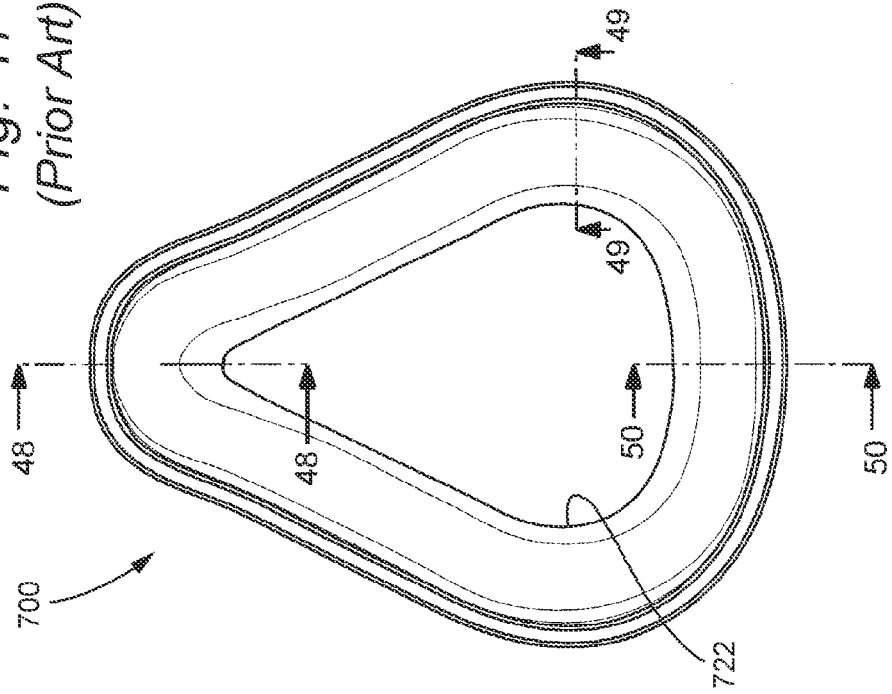
FIGS. 46-53 illustrate a known cushion commercially sold under the name of UltraMirage® Full Face by ResMed Ltd.
Figure 46:
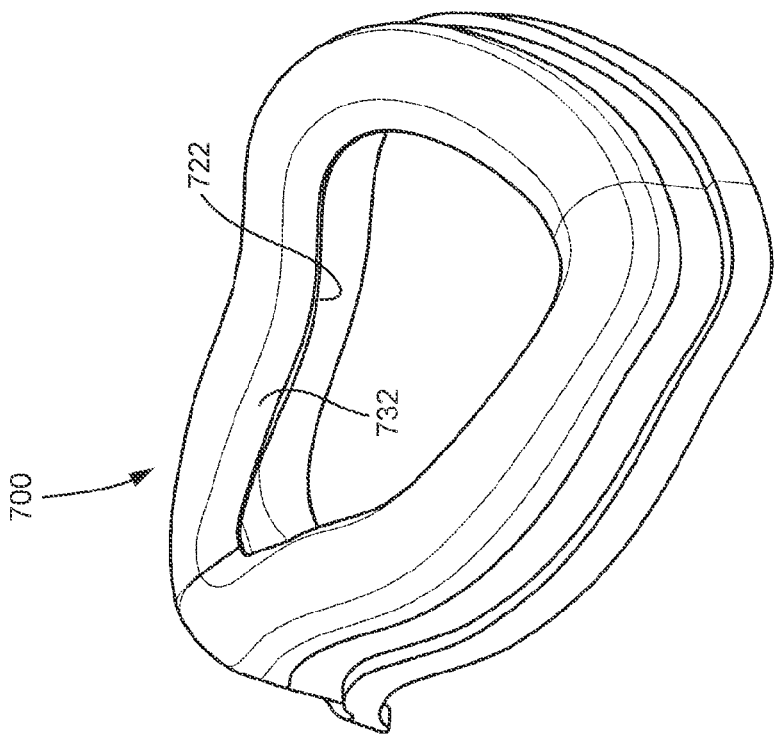

FIGS. 41-45 include hand-marked lines applied to the outer surface of the nasal bridge region 16 of the cushion 10 to illustrate the rolling action of the nasal bridge region 16 of the membrane 32 upon engagement with the patient's nose. As described above, the membrane 32 in the nasal bridge region 16 includes sloping sides 36 that meet to form an elongated crest 38 as shown in FIG. 41. As the patient's nasal bridge (simulated using a small rod) is engaged with the nasal bridge region 16 of the membrane 32 (see FIG. 42), the membrane 32 creates a steeply inverted section 44 wherein the sloping sides 36 invert their position as the membrane 32 moves between the underlying cushions 30 provided in the side of nose regions 17. As the membrane 32 comes more into contact with the patient's nasal bridge, the leading edge 46 of the inverted section "rolls" towards the top of the cushion 10 as the membrane 32 conforms to the patient's face as shown in FIG. 43. This structure is advantageous since it allows the cushion 10 to accommodate patients having a wide range of nasal profiles, including those with relatively low and relatively high root depth at the nose. FIGS. 44 and 45 show the nasal bridge region 16 of the membrane 32 in its completely inverted position. The creation of the steeply inverted section 44 upon engagement with the patient's nose provides a better seal and reduces the risk of creasing and/or folding and associated discomfort and leaks. That is, this configuration encourages rolling instead of creasing which can be detrimental to patient comfort and seal.

Alternative Embodiments

FIGS. 54-71 illustrate another embodiment of a cushion 510. In each of the figures, portions of the cushion 510 that are substantially similar to the cushion 10 are indicated with similar reference numerals.

Figure 64:
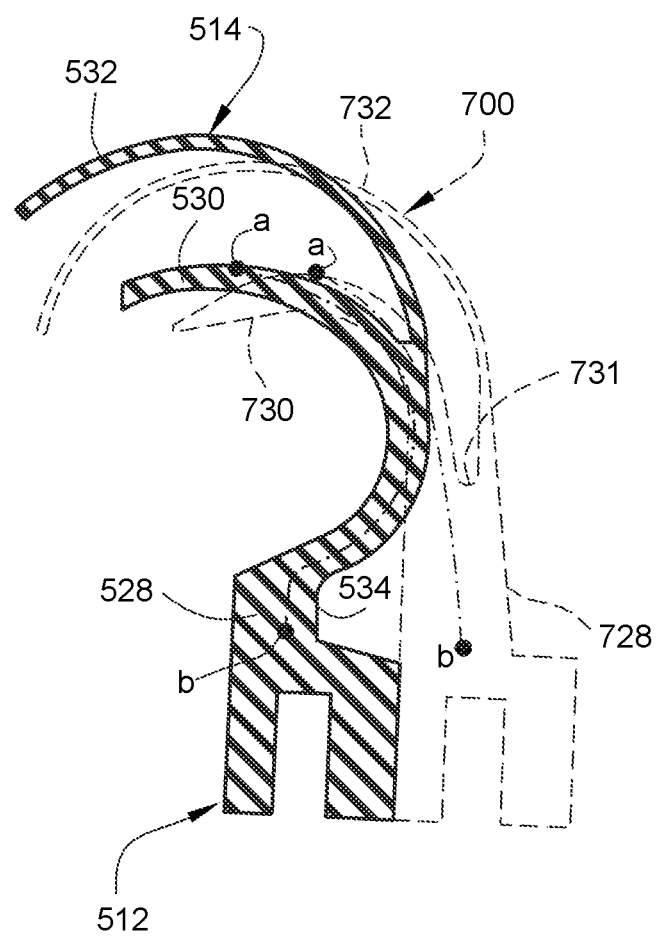
FIG. 64 is a cross-sectional view of a portion of the cushion shown in FIGS. 54-58 (in solid lines) overlaid with a cross-section of a known cushion commercially sold under the name of UltraMirage® Full Face by ResMed Ltd. (only relevant portions of the UltraMirage® cushion may be shown in dashed lines, i.e., there may be other different portions not shown)

FIG. 64 illustrates the base wall 528, underlying cushion 530, and membrane 532 of the cushion 510 (in solid lines) in relation to the base wall 728, underlying cushion 730, and membrane 732 of the UltraMirage® Full Face cushion 700 (in dashed lines). As illustrated, the cushion 510 has a different cross-sectional profile than the UltraMirage® Full Face cushion 700.

For example, the membrane 532 is connected to the underlying cushion 530 at a position that is further inwardly and upwardly with respect to the membrane connection of the UltraMirage® cushion 700. This arrangement substantially removes the vertically extending groove 731 provided in the UltraMirage® cushion 700. Also, this arrangement narrows the width of the membrane 532, e.g., in the range of 0-5, preferably about 2.5 mm, with respect to the corresponding portion of the UltraMirage® cushion 700. As a result of this and the inward movement of the non-face contacting portion 512, this narrows the total width of the cushion 510 by about 5 mm, e.g., about 2.5 mm per base, which provides a less obtrusive cushion and saves material. Also, the narrower membrane 532 provides less free length for the cushion 510 to bulge outwardly in use, thus helping to minimize or eliminate leakage. Further, the base wall 528 and the frame connection 529 are internally offset with respect to the most external cushion point, e.g., external surface of underlying cushion. FIG. 64 also shows the longer length a to b in the cushion 510 when compared to the UltraMirage® cushion 700.

Figure 65:
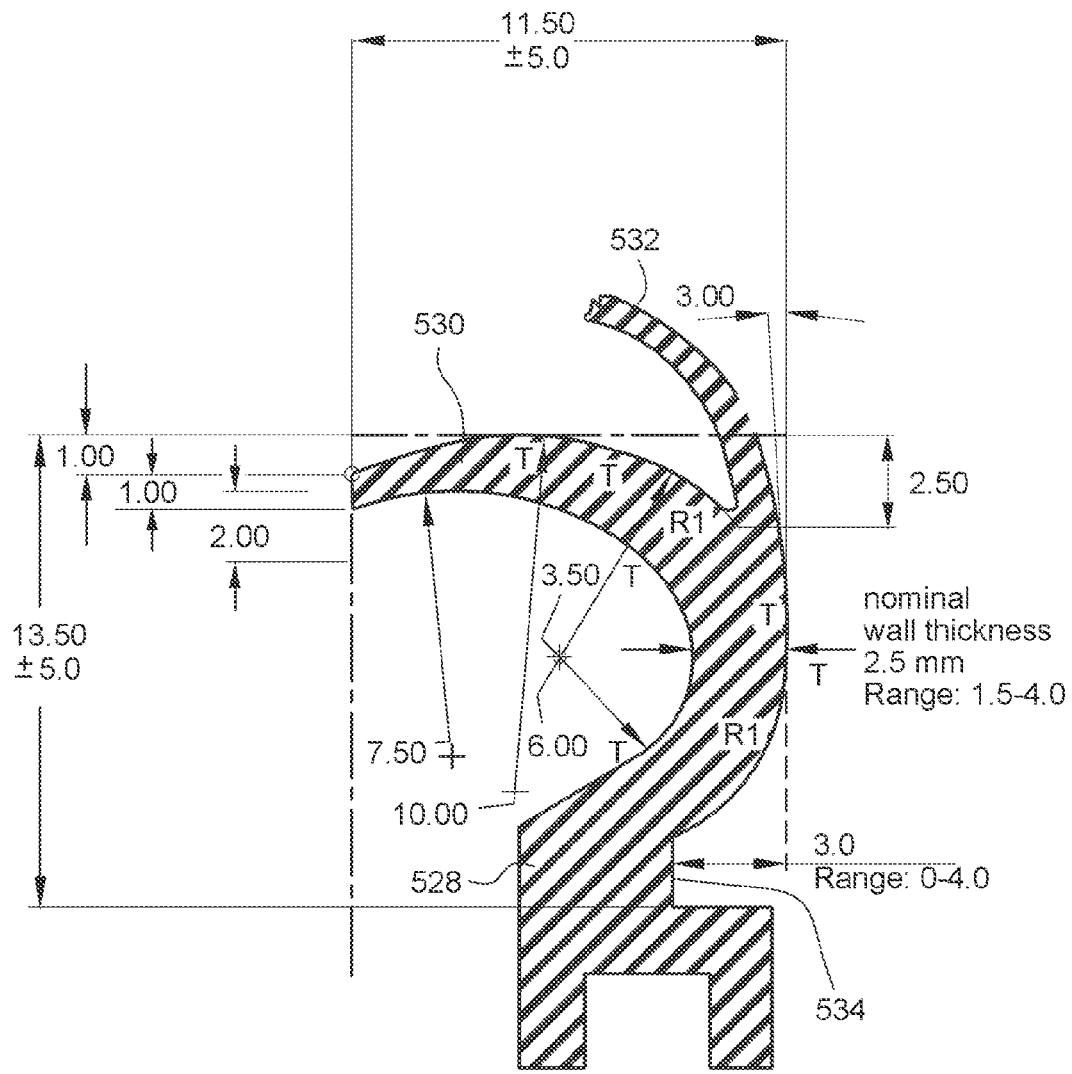
FIG. 65 is a cross-sectional view of a portion of the cushion shown in FIGS. 54-58 showing exemplary dimensions of an embodiment according to the present invention.
Figures 66, 67:
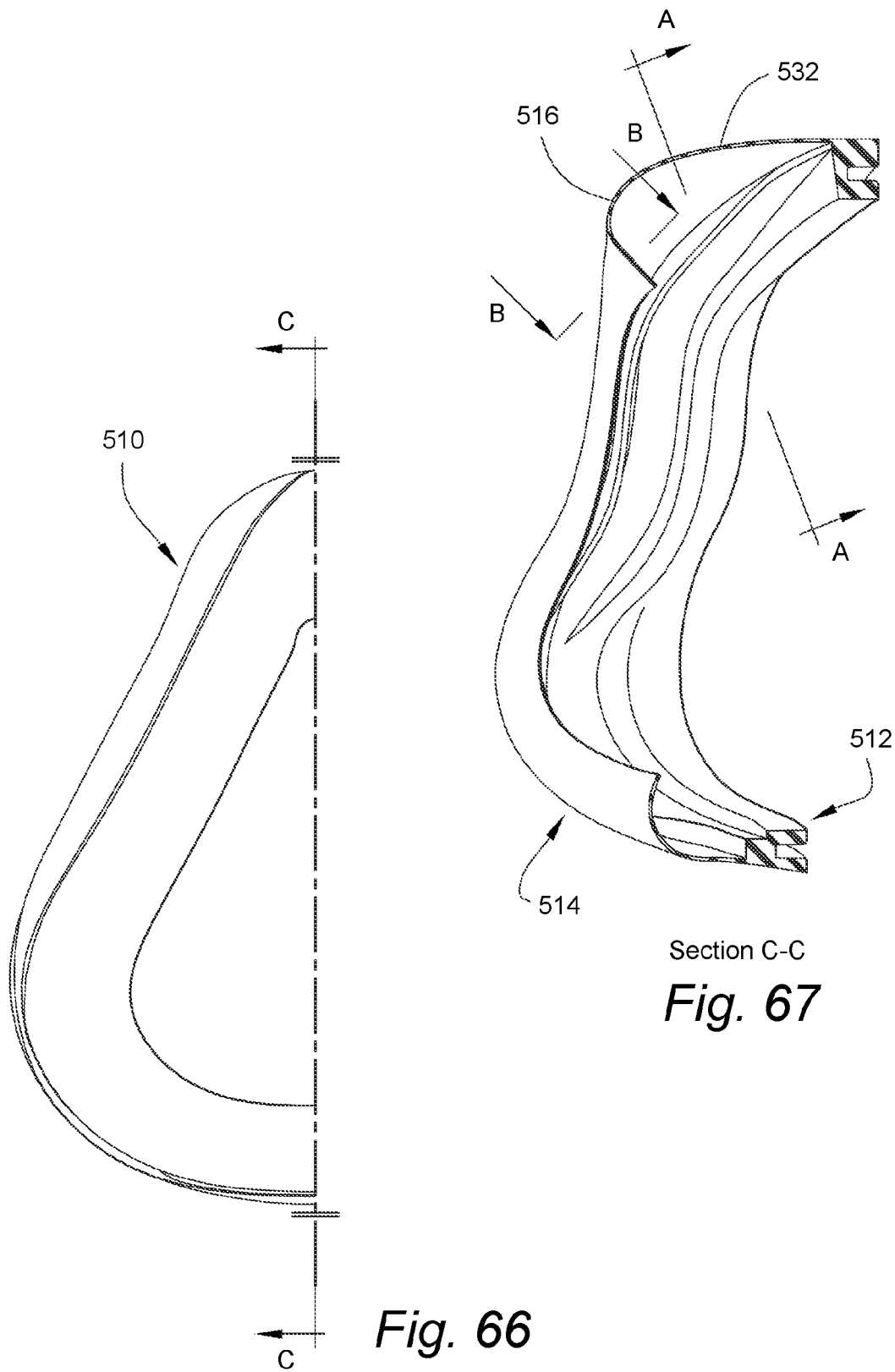
FIGS. 66-69 are cross-sectional views through the cushion shown in FIG. 54, and showing exemplary dimensions of an embodiment according to the present invention.

FIG. 65 illustrates further structural details and dimensions in one embodiment of the base wall 528, underlying cushion 530, and membrane 532 of the cushion 510. For example, the depth of the space 534 is in the range of 0-4.0 mm, preferably about 3.0 mm.

FIG. 68 illustrates the elongated ridge 535 in the nasal bridge region 516. Each of the sloping sides 536 is angled from the crest centerline in the range of 30-60°, preferably about 47°. The crest 538 has a radius of curvature in the range of 1.0-5.0 mm, preferably about 2.5 mm. As shown in FIG. 69, the forward end 540 of the elongated ridge 535 has a radius of curvature in the range of 1.5-7.0 mm, preferably about 4.0 mm.

Figure 70:
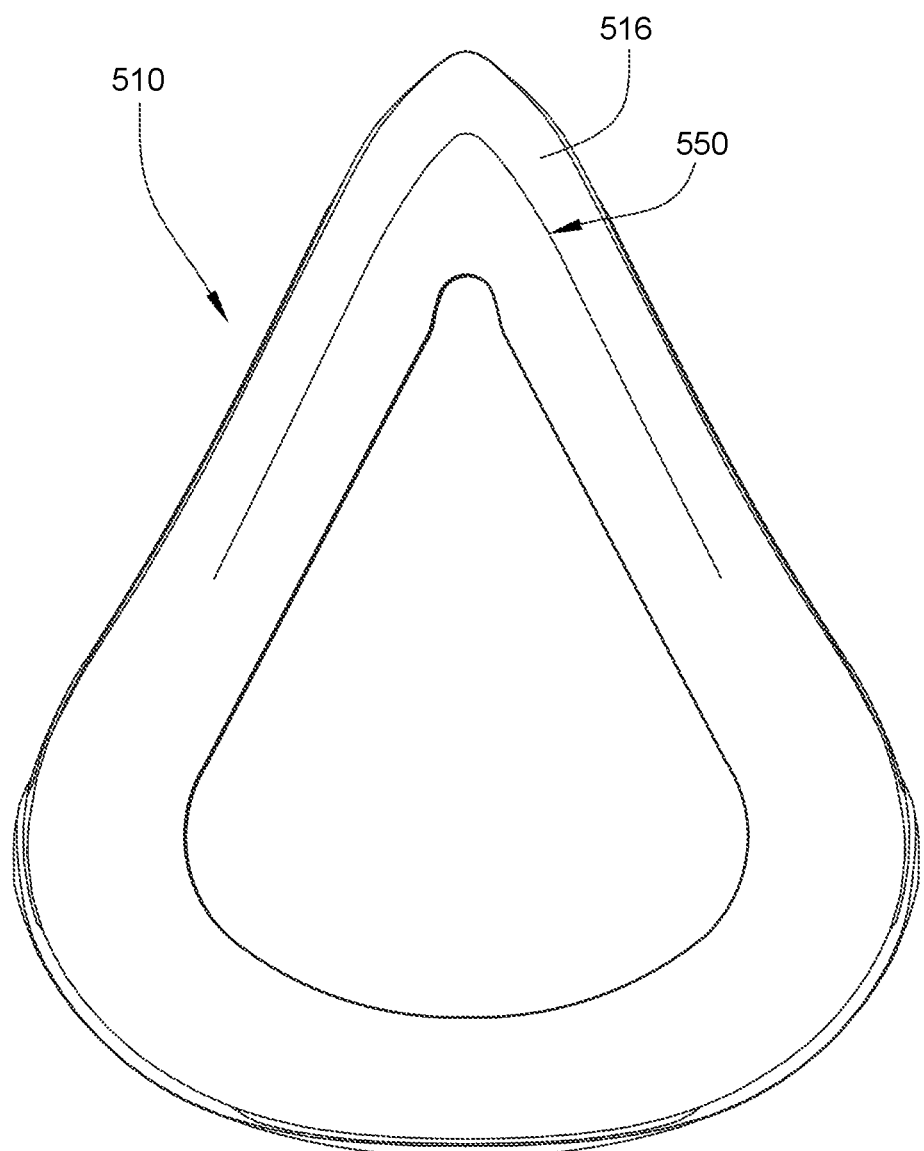
FIGS. 70-71 are plan and cross-sectional views, respectively, of the cushion shown in FIG. 54, and showing exemplary dimensions of an embodiment according to the present invention.
Figure 71:
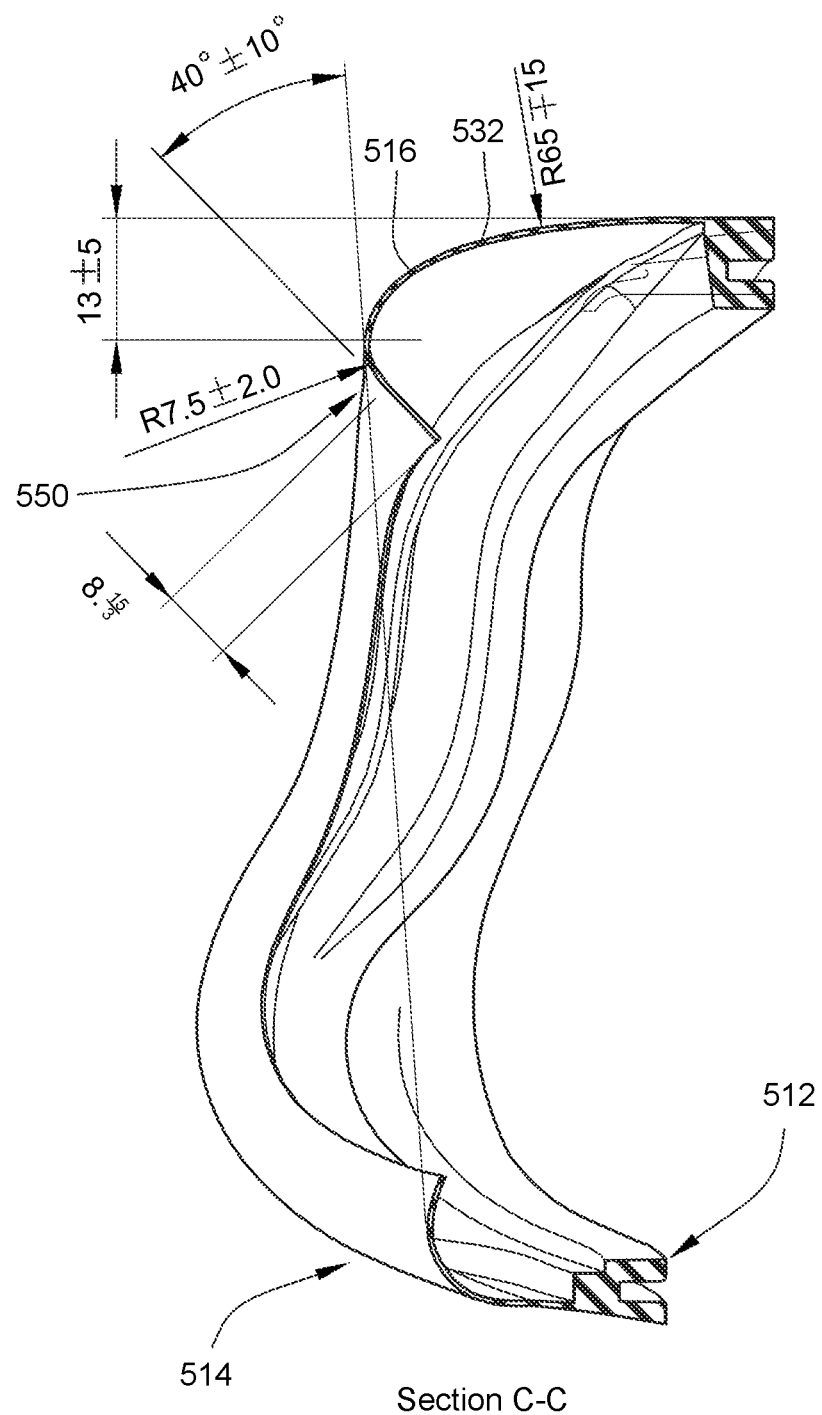
Figure 73:
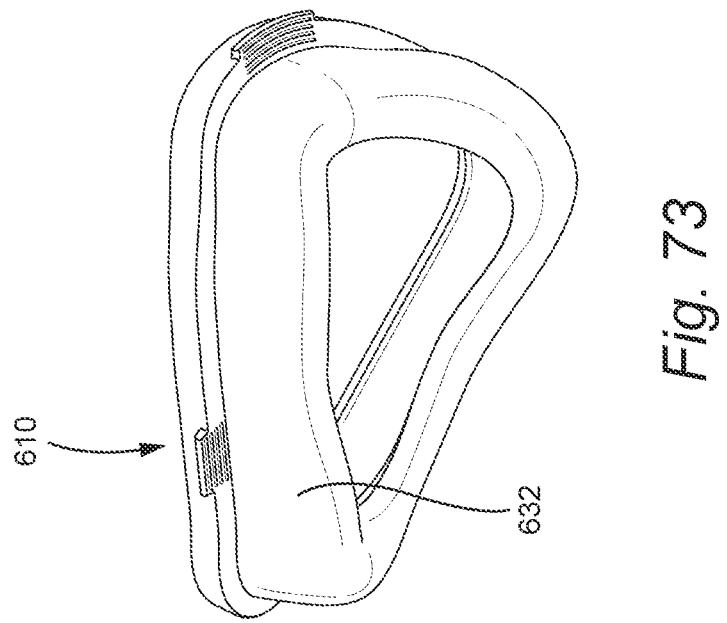
Figure 72:
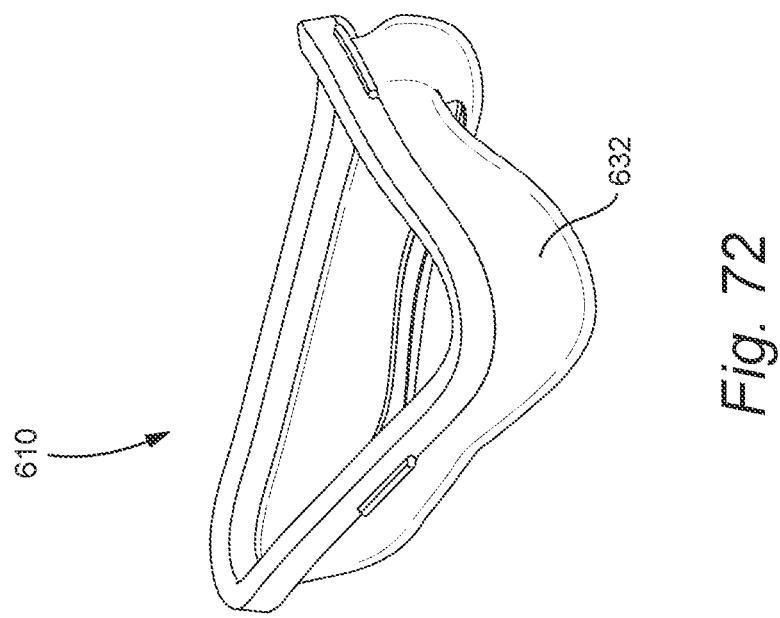

FIGS. 70 and 71 illustrate the flat portion 550 in the nasal bridge region 516 of the cushion 510. Also, as shown in FIG. 71, the membrane 532 in the nasal bridge region 516 has a first portion with a radius of curvature in the range of 50-80 mm, preferably about 65 mm, and a second portion with a radius of curvature in the range of 5.5-9.5 mm, preferably about 7.5 mm. In the illustrated embodiment, the membrane 532 is angled with respect to a face contacting plane of the cushion in the range of 30-50°, preferably about 40°.

Figure 76:
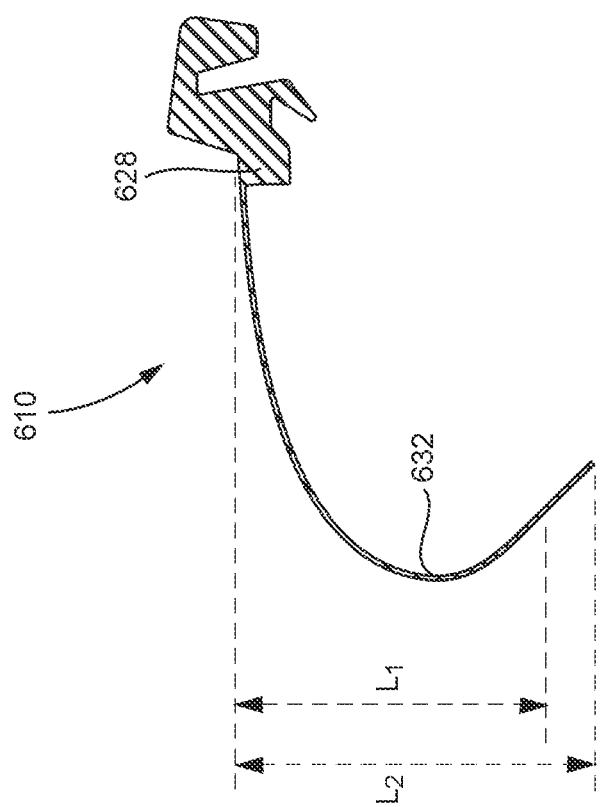
Figure 79:
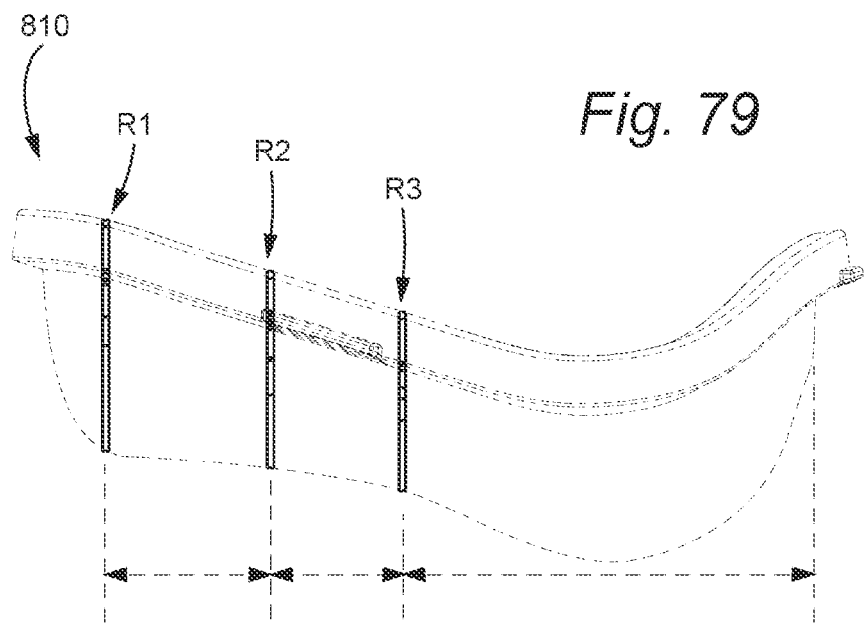
Figure 80:
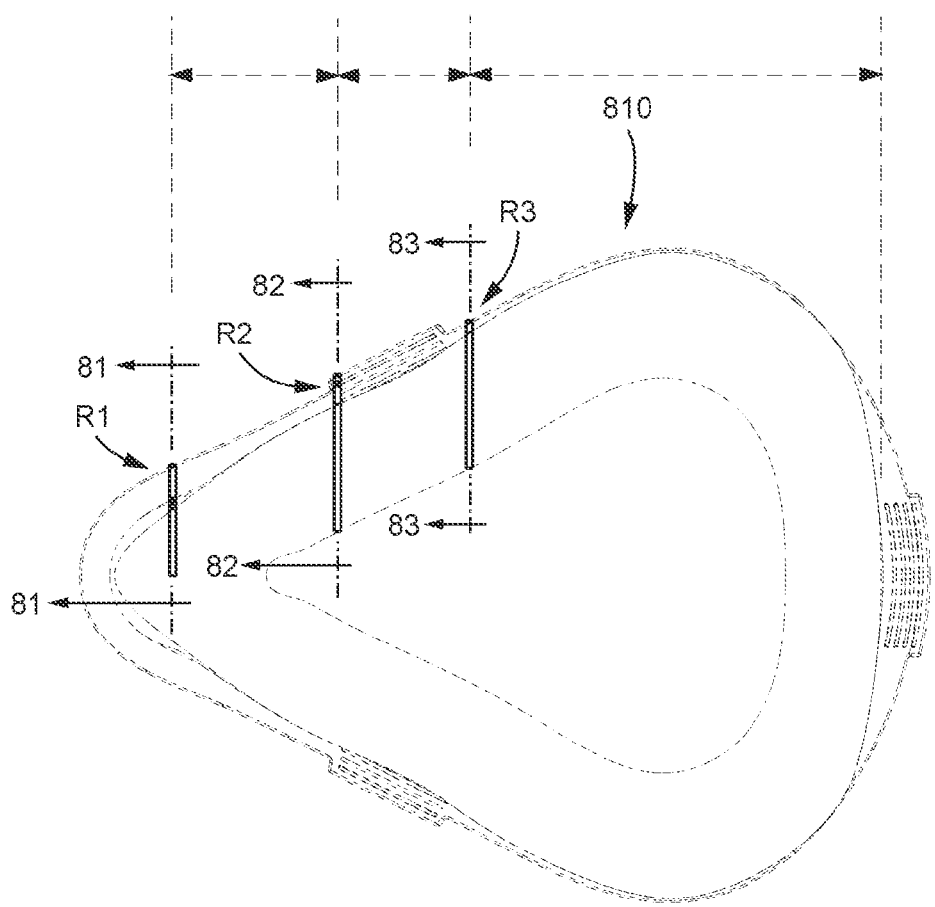
Figure 85:
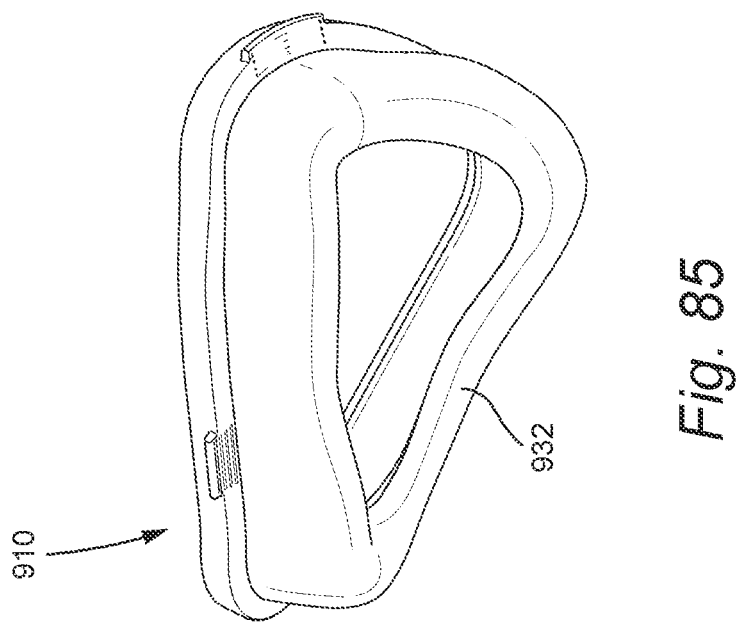
FIGS. 84-90 illustrate a cushion for a patient interface according to another embodiment of the present invention.
Figure 84:
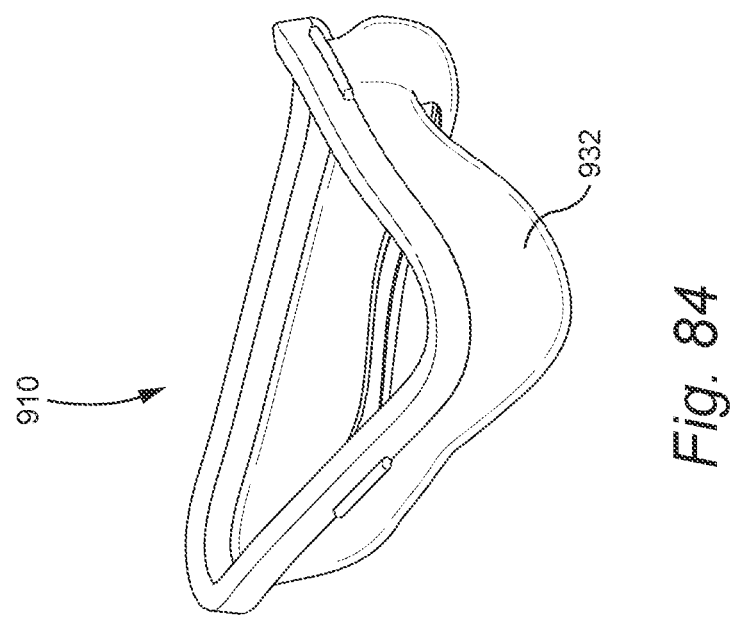
Figure 88:
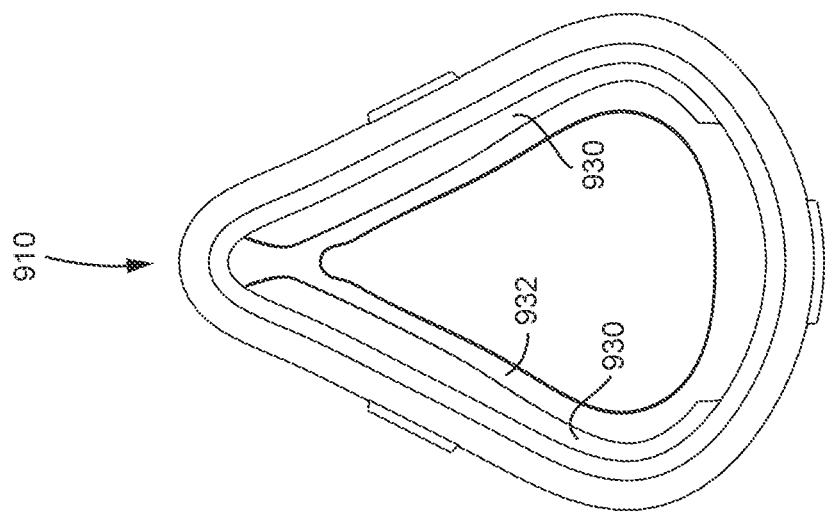
Figure 87:
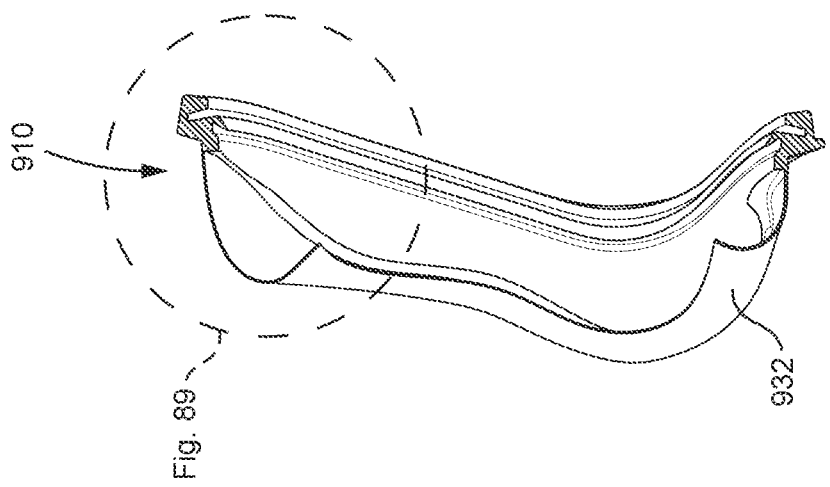
Figure 86:
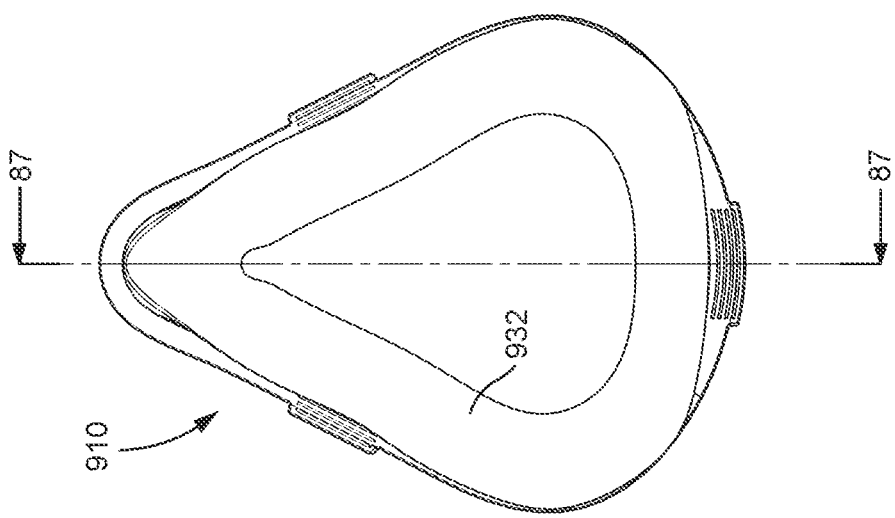

FIGS. 72-76 illustrate another embodiment of a cushion 610. As best shown in FIG. 76, the cushion includes at least a base wall 628 and a membrane 632. As illustrated, the length of the membrane 632 (e.g., membrane cross-sectional length) in a nasal bridge region may change. For example, the membrane length may be selected to have a shorter length $L_1$ or a longer length $L_2$ in the nasal bridge region.

As shown in FIGS. 74 and 75, the membrane length controls how far on the patient's nose the displaced cushion membrane will sit when fitted onto the patient's face (shown by the dotted line on the patient's facial profile). This arrangement prevents the potential (e.g., particularly for patients with a shallow nasal bridge depth) for any excess cushion membrane to sit too far down on the patient's nose, which may lead to facial discomfort and skin markings on the patient's nose.

FIGS. 77-83 illustrate another embodiment of a cushion 810. The cushion 810 includes a base wall 828, an underlying support cushion 830, and a membrane 832. As described above, the underlying cushion 830 is preferably provided on lateral sides of the cushion 810 only.

The base wall 828 may be internally offset with respect to the most external cushion point, e.g., external surface of membrane or underlying cushion. This arrangement provides a spring characteristic which may be varied around the cushion perimeter to vary the cushion flexibility (lateral and/or vertical) around the cushion perimeter, e.g., the cushion stiffness can be varied at each cushion region to suit the sealing requirements in each region which may vary due to the underlying facial structure of the patient. That is, the level if bias (e.g., from "hard" to "soft") along the sides of the cushion may be changed.

For example, FIGS. 77-83 illustrate cross-sections through three different regions R1, R2, R3 in the cushion 810. As shown in FIG. 81, the base wall 828, the underlying cushion 830, and the membrane 832 cooperate to define a relatively straight external surface 880. This provides a minimal spring component in the region R1, e.g., hard or stiff characteristics.

As shown in FIG. 82, the base wall 828, the underlying cushion 830, and the membrane 832 cooperate to define an external surface 882 that transitions from a relatively straight configuration to a curved configuration. This provides a relatively small offset for a more flexible spring component than the region R1.

As shown in FIG. 83, the base wall 828, the underlying cushion 830, and the membrane 832 cooperate to define an external surface 884 that curves outwards from the base wall 828. This provides a relatively large offset for an optimal spring component in the region R3, e.g., soft or flexible characteristics.

Thus, the cushion 810 may be designed to provide varying flexibilities around its perimeter which allows the cushion 810 to conform to a variety of facial shapes.

FIGS. 84-90 illustrate another embodiment of a cushion 910. The cushion 910 includes a base wall 928, an underlying support cushion 930, and a membrane 932. As illustrated, the underlying cushion 930 is preferably provided on lateral sides of the cushion 910 only, e.g., no underlying cushion at nasal bridge and chin regions (see FIG. 88).

Figure 89:
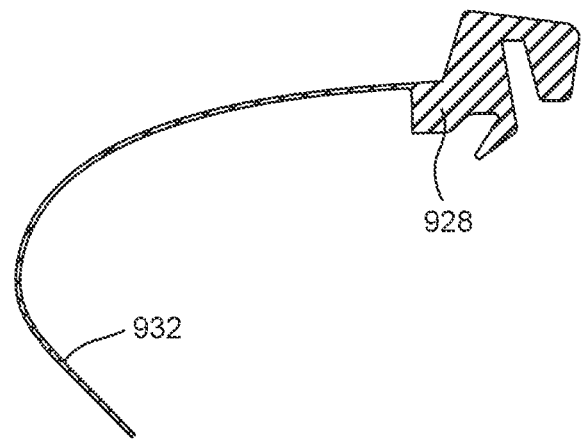
Figure 90:
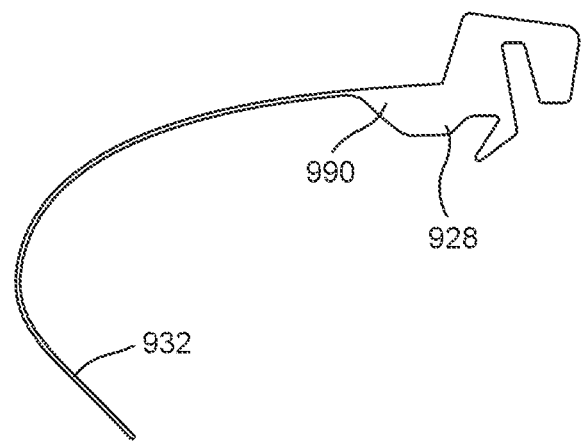

As shown in FIG. 90, the base wall 928 includes a tapered portion 990 when compared to FIG. 89, which tapers towards the membrane 932. This arrangement may improve moldability.

Figure 91:
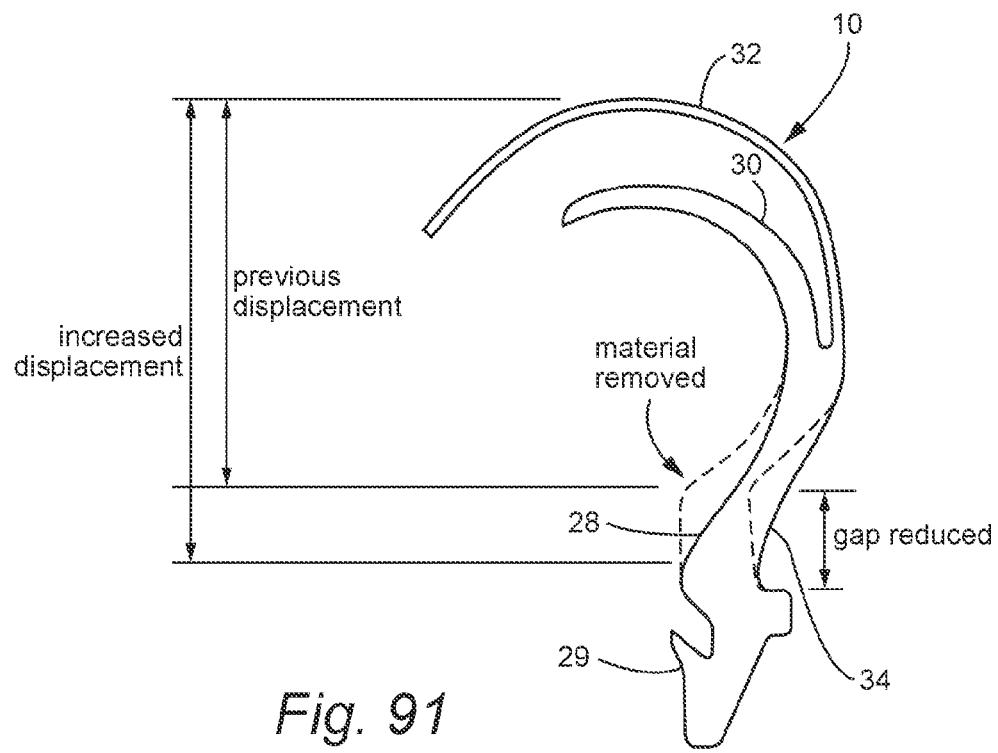
FIG. 91 illustrates an alternative cushion cross-section to that shown in FIG. 34A.

FIG. 91 illustrates an alternative arrangement to the cushion 10 of FIG. 34A (arrangement of FIG. 34A shown in dashed lines). As illustrated, material has been removed from the side wall 28 and the space or gap 34 has been reduced with respect to the arrangement of FIG. 34A. This arrangement of FIG. 91 increases displacement with respect to the previous displacement of FIG. 34A. The increased displacement is achieved by the changed geometry in the side wall 28. It is noted that the gap 34 may be variable or constant around the cushion perimeter.

Figure 92:
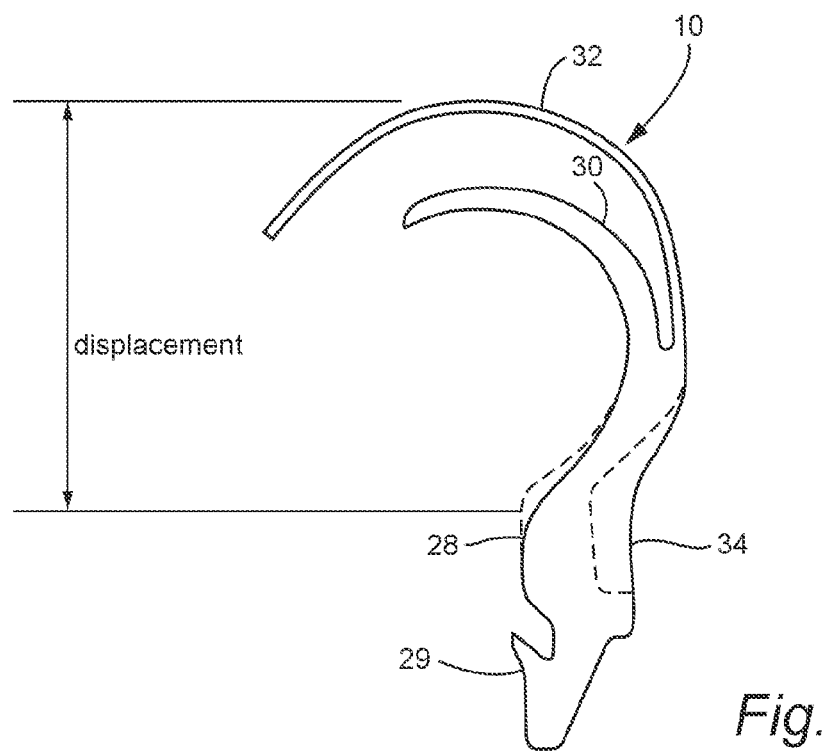
FIG. 92 illustrates another alternative cushion cross-section to that shown in FIG. 34A.

FIG. 92 illustrates an alternative arrangement to the cushion 10 of FIG. 34A (arrangement of FIG. 34A shown in dashed lines). As illustrated, some material has been removed from the side wall 28 and the space or gap 34 has been reduced with respect to the arrangement of FIG. 34A. This arrangement of FIG. 92 increases displacement with respect to the previous displacement of FIG. 34A. The increased displacement is achieved by the changed geometry in the side wall 28. This arrangement may require the cross-section of the base wall 28 to be thickened to add stiffness around the cushion perimeter or locally. Stiffening may be achieved by local ribs where required.

Figure 93:
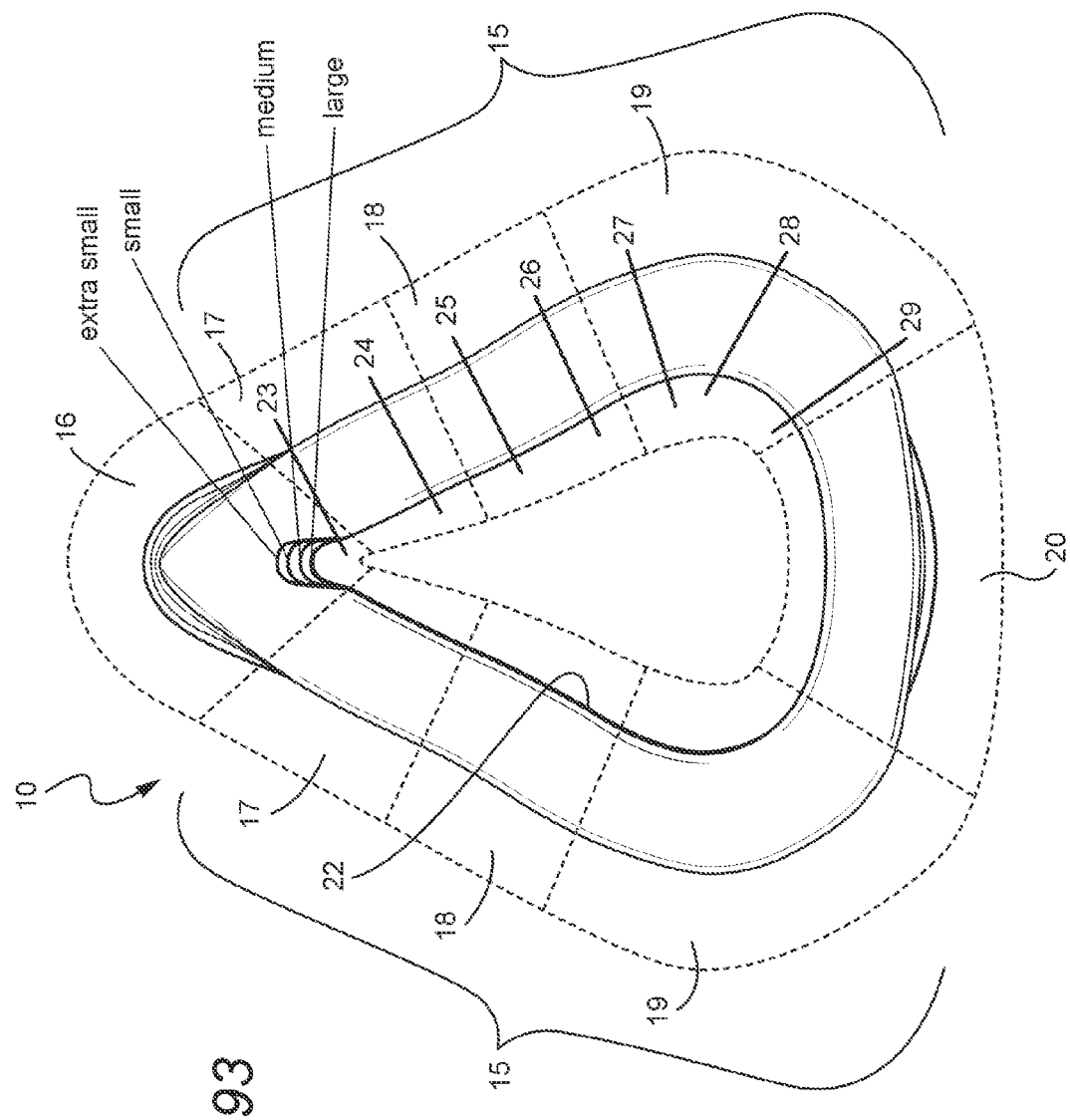
FIG. 93 illustrates an alternative cushion arrangement to that shown in FIG. 15.

FIG. 93 illustrates an alternative arrangement to the cushion 10 shown in FIG. 15. As illustrated, the keyhole-shaped cutout (for receiving the patient's nasal bridge region) may be larger as the mask size reduces. For example, the cutout is larger for an extra small size mask than a large size mask.

It is noted that the cross-section design of the cushion at specific areas of the patient's face (e.g., FIGS. 23-29) may be in the specific area or any area around the cushion perimeter. That is, the cross-section design should not be limited to the specified area. Also, the cross-section shown in FIGS. 91 and 92 may be employed at any point around the cushion perimeter.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask assembly for delivering breathable gas to a patient, the assembly comprising:
    a co-molded frame and cushion structure including:
        a frame; and
        a full-face cushion co-molded to the frame and including a nasal bridge region, a pair of side of nose regions, a pair of upper cheek regions, a pair of lower cheek regions and a chin region, the cushion defining, at least in part, a breathing cavity, the cushion comprising:
            a face-contacting membrane including a nasal bridge region, a pair of side of nose regions, a pair of upper cheek regions, a pair of lower cheek regions and a chin region forming a continuous sealing structure to form a continuous seal on nasal bridge, side of nose, upper cheek, lower cheek and chin regions of the patient's face, the face-contacting membrane having an inner edge that defines a triangular-shaped aperture to receive the patient's nose and mouth; and
            a support structure to support the face-contacting membrane, the support structure including:
                a base wall; and
                an underlying cushion connected to the base wall, the underlying cushion, in a cross-sectional view, extending from the base wall and toward the breathing cavity to provide support for the face-contacting membrane, the underlying cushion including a pair of side of nose regions, a pair of upper cheek regions and a pair of lower cheek regions, such that the underlying cushion and the face-contacting membrane form at least a double-walled construction at least in the pair of side of nose regions, the pair of upper cheek regions and the pair of lower cheek regions of the cushion, said at least double-walled construction being configured such that the underlying cushion is positioned to restrain movement of the face-contacting membrane,
    wherein, in a cross-sectional view, a widest point of the cushion is an external surface of the underlying cushion or face-contacting membrane, and the base wall is internally offset, with respect to the widest point of the cushion,
    wherein the cushion has only a single-walled construction formed by the face-contacting membrane in a majority of the chin region of the cushion so as to allow the face-contacting membrane to readily flex in the chin region of the cushion.

2. The assembly according to claim 1, wherein the underlying cushion includes a nasal bridge region such that the underlying cushion is continuous at least along the pair of upper cheek regions, the pair of side of nose regions and the nasal bridge region of the underlying cushion.

3. The assembly according to claim 2, wherein a first cross-sectional configuration of the base wall and the underlying cushion in the nasal bridge region of the cushion is different than a second cross-sectional configuration of the base wall and the underlying cushion in the pair of lower cheek regions of the cushion.

4. The assembly according to claim 3, wherein the base wall includes a frame connection, the frame connection having an engaging portion onto which a portion of the frame is positioned, the engaging portion and the portion of the frame forming a part of the co-molded frame and cushion structure.

5. The assembly according to claim 3, wherein the first and second cross-sectional configurations of the base wall and the underlying cushion in the nasal bridge region and the pair of lower cheek regions of the cushion vary by varying an underlying cushion offset relative to the base wall.

6. The assembly according to claim 5, wherein:
the underlying cushion is movable when the cushion is worn and a force by the frame is exerted on the cushion,
the underlying cushion being movable from an initial position towards a space exterior of the cushion when the frame force is exerted on the cushion, and
the underlying cushion is configured to resiliently move back into the initial position when the frame force is no longer exerted on the cushion, and
wherein the cushion is configured to exert a spring force when the frame force is exerted on the cushion such that the underlying cushion resiliently moves back into the initial position when the frame force is no longer exerted on the cushion.

7. The assembly according to claim 6, wherein the first and second cross-sectional configurations of the base wall and the underlying cushion vary so as to provide a spring constant in the nasal bridge region of the cushion that is different than a spring constant in the pair of lower cheek regions of the cushion,
wherein the face-contacting membrane extends from the underlying cushion and terminates at the inner edge of the face-contacting membrane.

8. The assembly according to claim 7, wherein the face-contacting membrane in the nasal bridge region of the cushion has a height that is greater than a height of the face-contacting membrane in the pair of side of nose regions of the cushion.

9. The assembly according to claim 1, wherein the face-contacting membrane in the nasal bridge region of the cushion has a height that is greater than a height of the face-contacting membrane in the pair of side of nose regions of the cushion.

10. A mask assembly for delivering breathable gas to a patient, the assembly comprising:
a co-molded frame and cushion structure including:
a frame; and
a full-face cushion co-molded to the figure and including a nasal bridge region, a pair of side of nose regions, a pair of upper cheek regions, a pair of lower cheek regions and a chin region, the cushion defining, at least in part, a breathing cavity, the cushion comprising;
a face-contacting membrane including a nasal bridge region, a pair of side of nose regions, a pair of upper cheek regions, a pair of lower cheek regions and a chin region forming a continuous sealing structure to form a continuous seal on nasal bridge, side of nose, upper cheek, lower cheek and chin regions of the patient's face, the face-contacting membrane having an inner edge that defines a triangular-shaped aperture to receive the patient's nose and mouth; and
a support structure to support the face-contacting membrane, the support structure including:
a base wall; and
an underlying cushion connected to the base wall, the underlying cushion, in a cross-sectional view, extending from the base wall and toward the breathing cavity to provide support for the face-contacting membrane, the underlying cushion including a pair of side of nose regions, a pair of upper cheek regions and a pair of lower cheek regions, such that the underlying cushion and the face-contacting membrane form at least a double-walled construction at least in the pair of side nose regions, the pair of upper cheek regions and the pair of lower cheek regions of the cushion, said at least double-walled construction being configured such that the underlying cushion is positioned to restrain movement of the face-contacting membrane,
wherein, in a cross-sectional view, a widest point of the cushion is an external surface of the underlying cushion or face-contacting membrane, and the base wall is internally offset, with respect to the widest point of the cushion,
wherein:
the underlying cushion includes an inwardly curved portion that extends into and curves inwardly toward the breathing cavity in a spaced-relationship with respect to the face-contacting membrane,
the face-contacting membrane, from front view, covers the inwardly curved portion of the underlying cushion,
the inwardly curved portion of the underlying cushion terminates at a free end of the underlying cushion, the free end of the underlying cushion being disposed within the breathing cavity, and
the inwardly curved portion of the underlying cushion extends along the side of nose, upper cheek and lower cheek regions of the underlying cushion and terminates such that the inwardly curved portion of the underlying cushion is absent in a majority of the chin region of the cushion.

11. The assembly according to claim 10, wherein the inwardly curved portion of the underlying cushion terminates proximate a transition between the chin region and a respective lower cheek region of the cushion.

12. The assembly according to claim 11, wherein the underlying cushion terminates in each lower cheek region of the cushion.

13. The assembly according to claim 11, wherein the underlying cushion terminates in the chin region of the cushion.

14. The assembly according to claim 10, wherein a first cross-sectional configuration of the base wall and the underlying cushion in the nasal bridge region of the cushion and a second cross-sectional configuration of the base wall and the underlying cushion in the pair of lower cheek regions of the cushion vary from one another by varying an underlying cushion offset relative to the base wall.

15. The assembly according to claim 14, wherein:
the underlying cushion is movable when the cushion is worn and a force is exerted on the cushion,
the underlying cushion is movable from an initial position towards a space exterior of the cushion when the force is applied, and
the underlying cushion is configured to resiliently move back into the initial position when the force is no longer exerted on the cushion, and
wherein the cushion is configured to exert a spring force when the force is exerted on the cushion such that the underlying cushion resiliently moves back into the initial position when the force is no longer exerted on the cushion.

16. A mask assembly for delivering breathable gas to a patient, the assembly comprising:
a co-molded frame and cushion structure including:
a frame; and
a full-face cushion co-molded to the frame and including a nasal bridge region, a pair of side of nose regions, a pair of upper cheek regions, a pair of lower cheek regions and a chin region, the cushion defining, at least in part, a breathing cavity, the cushion comprising:
a continuous face-contacting membrane having an inner edge defining an aperture adapted to receive a patient's nose and mouth, said face-contacting membrane having a nasal bridge region, a pair of side of nose regions, a pair of upper cheek regions, a pair of lower cheek regions and a chin region which together form a continuous sealing structure; and
a support structure for the face-contacting membrane, comprising:
a continuous side wall having, in a cross-sectional view, a top portion and a bottom portion; and
a pair of underlying cushions joined in the nasal bridge region of the cushion and extending from the top portion of the side wall, each of said underlying cushions terminating at a free end to provide support for the face-contacting membrane in the nasal bridge region, side of nose regions, upper cheek regions and lower cheek regions of the cushion, the pair of underlying cushions extending, in a cross-sectional view, away from the side wall and toward the breathing cavity such that at least the free ends of the pair of underlying cushions are disposed within the breathing cavity,
wherein the face-contacting membrane extends, in a cross-sectional view, from the top portion of the side wall to the inner edge of the face-contacting membrane in a spaced-relationship with the pair of underlying cushions to, from front view, cover the pair of underlying cushions,
wherein, in a cross-sectional view, a widest point of the cushion is an external surface of the support structure or face-contacting membrane, and the bottom portion of the side wall is continuously and inwardly offset with respect to the external surface,
wherein the height difference between an apex of the face-contacting membrane and an apex of the pair of underlying cushions is greatest in the nasal bridge region of the cushion, and
wherein the pair of underlying cushions is absent in a majority of the chin regions of the cushion such that a portion of the face-contacting membrane is unrestrained by the pair of underlying cushions in at least a portion of the chin region so as to allow the face-contacting membrane to flex toward the breathing cavity in the at least a portion of the chin region.

17. The assembly according to claim 16, wherein the face-contacting membrane and the pair of underlying cushions form at least a double-walled construction at least in the side of nose regions, upper cheek regions and lower cheek regions of the cushion such that the pair of underlying cushions is positioned to restrain movement of the face-contacting membrane, and
wherein the cushion has only a single-walled construction in the at least a portion of the chin region of the cushion.

18. The assembly according to claim 17, wherein a first cross-sectional configuration of the side wall and the pair of underlying cushions in the nasal bridge region of the cushion and a second cross-sectional configuration of the side wall and the pair of underlying cushions in the lower cheek regions of the cushion vary by varying an underlying cushion offset.

19. The assembly according to claim 18, wherein the side wall includes a frame connection, the frame connection having an engaging portion onto which a portion of the frame is positioned, the engaging portion and the portion of the frame forming a part of the co-molded frame and cushion structure.

20. The assembly according to claim 18, wherein:
the side wall extends laterally beyond a first exterior portion of the cushion,
the side wall is movable with respect to the first exterior surface of the cushion when the cushion is worn and a force by the frame is exerted on the cushion, and
the side wall is movable from an initial position towards a space exterior of the cushion when the frame force is exerted on the cushion, and
the side wall is configured to resiliently move back into the initial position when the frame force is no longer exerted on the cushion.

21. The assembly according to claim 20, wherein the cushion is configured to exert a spring force when the frame force is exerted on the cushion such that the side wall resiliently moves back into the initial position when the frame force is no longer exerted on the cushion.

22. The assembly according to claim 21, wherein at least a portion of the side wall includes a spring configuration that, at least in part, defines displacement of the cushion with respect to the frame force exerted on the cushion, and
wherein the first and second cross-sectional configurations of the side wall and the pair of underlying cushions vary so as to provide a spring constant in the nasal bridge region of the cushion that is different than a spring constant in the lower cheek regions of the cushion.

23. The assembly according to claim 16, wherein the face-contacting membrane, in the nasal bridge region, includes a contoured portion that curves inwardly and terminates at the inner edge of the face-contacting membrane, the contoured portion being configured to follow a contour or curvature of the patient's nasal bridge region.

24. The assembly according to claim 23, wherein at least a portion of the side wall includes a spring configuration that, at least in part, defines displacement of the cushion with respect to the frame force exerted on the cushion, and
wherein a first cross-sectional configuration of the side wall and the pair of underlying cushions in the nasal bridge region of the cushion and a second cross-sectional configuration of the side wall and the pair of underlying cushions in the lower cheek regions of the cushion vary from one another so as to provide a spring constant in the nasal bridge region of the cushion that is different than a spring constant in the lower cheek regions of the cushion.

25. The assembly according to claim 16, wherein:
the side wall extends laterally beyond a first exterior portion of the cushion,
the side wall is movable with respect to the first exterior portion of the cushion when the cushion is worn and a force by the frame is exerted on the cushion, and
the side wall is movable from an initial position towards a space exterior of the cushion when the frame force is exerted on the cushion, and
the side wall is configured to resiliently move back into the initial position when the frame force is no longer exerted on the cushion.

26. The assembly according to claim 25, wherein the cushion is configured to exert a spring force when the frame force is exerted on the cushion such that the side wall resiliently moves back into its initial position when the frame force is no longer exerted on the cushion.

27. The assembly according to claim 26, wherein the face-contacting membrane and the pair of underlying cushions form at least a double-walled construction at least in the nasal bridge region, side of nose regions and upper cheek regions of the cushion such that the pair of underlying cushions is positioned to restrain movement of the face-contacting membrane.

28. The assembly according to claim 27, wherein the face-contacting membrane, in the nasal bridge region, has a substantially flat portion in elevation view.

29. The assembly according to claim 16, wherein each of said underlying cushions is continuous along a respective upper cheek region and a respective lower cheek region of the cushion, and each of said underlying cushions terminates proximate a transition between the chin region and the respective lower cheek region of the cushion.

30. The assembly according to claim 29, wherein the cushion has only a single-walled construction formed by the face-contacting membrane in at least a portion of the chin region so as to allow the face-contacting membrane to readily flex in the at least a portion of the chin region without restraint due to the pair of underlying cushions.

\* \* \* \* \*